US012735408B2

(12) United States Patent
Din Belle et al.

(10) Patent No.: US 12,735,408 B2
(45) Date of Patent: Sep. 15, 2026

(54) 2,3-DIHYDRO-4H-BENZO[B][1,4]OXAZIN-4-YL)(5-(PHENYL)-PYRIDIN-3-YL) METHANONE DERIVATIVES AND SIMILAR COMPOUNDS AS CYP11A1 INHIBITORS FOR THE TREATMENT OF PROSTATE CANCER

(71) Applicant: ORION CORPORATION, Espoo (FI)

(72) Inventors: David Din Belle, Espoo (FI); Pekka Pietikäinen, Espoo (FI); Petteri Rummakko, Espoo (FI); Gerd Wohlfahrt, Baunschweig (DE)

(73) Assignee: ORION CORPORATION, Espoo (FI)

( * ) Notice: Subject to any disclaimer, the term of this patent is extended or adjusted under 35 U.S.C. 154(b) by 474 days.

(21) Appl. No.: 18/255,218

(22) PCT Filed: Nov. 30, 2021

(86) PCT No.: PCT/FI2021/050828
§ 371 (c)(1),
(2) Date: May 31, 2023

(87) PCT Pub. No.: WO2022/117920
PCT Pub. Date: Jun. 9, 2022

(65) Prior Publication Data

US 2024/0124431 A1 Apr. 18, 2024

(30) Foreign Application Priority Data

Dec. 1, 2020 (FI) ..................................... 20206226

(51) Int. Cl.

| | |
|---|---|
| ***C07D 413/06*** | (2006.01) |
| ***A61K 45/06*** | (2006.01) |
| ***C07D 401/06*** | (2006.01) |
| ***C07D 401/12*** | (2006.01) |
| ***C07D 401/14*** | (2006.01) |
| ***C07D 405/14*** | (2006.01) |
| ***C07D 413/12*** | (2006.01) |
| ***C07D 413/14*** | (2006.01) |
| ***C07D 471/04*** | (2006.01) |

(52) U.S. Cl.
CPC ............ *C07D 413/06* (2013.01); *A61K 45/06* (2013.01); *C07D 401/06* (2013.01); *C07D 401/12* (2013.01); *C07D 401/14* (2013.01); *C07D 405/14* (2013.01); *C07D 413/12* (2013.01); *C07D 413/14* (2013.01); *C07D 471/04* (2013.01)

(58) Field of Classification Search
CPC .. C07D 413/06; C07D 401/06; C07D 401/12; C07D 401/14; C07D 405/14; C07D 413/12; C07D 413/14; C07D 471/04; A61K 45/06
See application file for complete search history.

(56) References Cited

FOREIGN PATENT DOCUMENTS

| | | |
|---|---|---|
| EA | 035757 B1 | 8/2020 |
| RU | 2695524 C2 | 7/2019 |
| WO | WO 2013037779 A1 | 3/2013 |
| WO | WO 2014191338 | 12/2014 |
| WO | WO 2018/115591 A1 | 6/2018 |

OTHER PUBLICATIONS

CAS Reg. No. 2405169-81-3 (Jan. 12, 2020) (Year: 2020).*
2405169-81-3 (Jan. 12, 2020) (Year: 2020).*
Karimaa et al. Mol. Cancer Ther 2022; 21: 1765-1776) (Year: 2022).*
Bastin et al., 2000, "Salt Selection and Optimization Procedures for Pharmaceutical New Chemical Entities," Organic Process Research and Development, 4:427-435.
Belikov, 2007, "MEDpress-inform", Pharmaceutical Chemistry Textbook 4th Edition pp. 27-29.
Cai et al., 2011, "Intratumoral de novo steroid synthesis activates androgen receptor in castration-resistant prostate cancer and is upregulated by treatment with CYP17A1 inhibitors," Cancer Research 71(20):6503-6513.
Chou, 2010, "Drug Combination Studies and Their Synergy Quantification Using the Chou-Talalay Method," Cancer Res, 70(2):440-446.
Dyson et al., 1964, Chemistry of Synthetic Medicinal Substances, M: World, pp. 12-19, 1964.
Gavrilov, 2010, "Pharmaceutical technology,". Manufacture of Medicinal Products Textbook, p. 20.

(Continued)

*Primary Examiner* — Brandon J Fetterolf
(74) *Attorney, Agent, or Firm* — Jones Day

(57) ABSTRACT

The present invention relates to compounds of formula (I), (I)

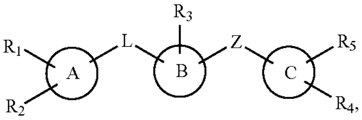

wherein A is a 3-10 membered carbocyclyl or a 4-12 membered heterocyclyl containing 1-4 heteroatoms selected from O, N, or S; B is any of the following groups (1), (2), or (3); C is any of the following groups (1'), (2'), (3'), or (4'); $G_1$ is $CH_2$, NH, or O; $G_2$ and $G_3$ are, independently, CH or N; Z is —C(O)—, —$SO_2$—, —$C_{1-3}$ alkyl-, or —$CH_2$—C(O)—; L is a bond, —$C_{1-7}$ alkyl-, or —$C_{1-7}$ alkenyl-. The compounds of formula (I) are cytochrome P450 monooxygenase 11A1 (CYP11A1) inhibitors. The compounds are useful as medicaments in the treatment of steroid receptor, for example, androgen receptor or estrogen receptor, dependent diseases and conditions, such as cancer including prostate cancer and estrogen cancer.

27 Claims, No Drawings

(56) References Cited

OTHER PUBLICATIONS

Kearns et al., 2003, "Developmental Pharmacology—Drug Disposition, Action, and Therapy in Infants and Children," N Engl J Med 349:1157-1167.
Kharkevich, 2010, "Pharmacology" M: GEOTAR-Media, 10th Ed Textbook pp. 72-82.
Kholodov et al., 1985, Clinical Pharmacokinetics, Moscow, Medicine, pp. 83-98, 134-138, 160, 378-380.
Mashkovsky, 2002, Medicines 14th Edition, vol. 1, p. 11.
Oksala et al., 2017, "ODM-208, a novel CYP11A1-inhibitor as a therapeutic approach for the treatment of castration-resistant prostate cancer," Annals of Oncology 28(5): Abstract/Poster 28P.
Sergeev, 1975, "Brief course in molecular pharmacology" p. 10.
CAS Registry No. 2462832-39-7, retrieved from STN Database [online] Chemical Abstracts Services, Sep. 1, 2025 (1 page).
CAS Registry No. 2460061-75-8, retrieved from STN Database [online] Chemical Abstracts Services, Sep. 1, 2025 (1 page).
CAS Registry No. 2432880-22-1, retrieved from STN Database [online] Chemical Abstracts Services, Sep. 1, 2025 (1 page).
International Search Report of International Application No. PCT/FI2021/050828, mailed Feb. 23, 2022 (2 pages).
Murineddu Gabriele et al., "Novel N-aryl nicotinamide derivatives: Taking stock on 3,6-diazabicyclo[3.1.1]heptanes as ligands for neuronal acetylcholine receptors," *Eur J Med Chem.*, vol. 180, 2019, pp. 51-61.
Belikov, 2007, "MEDpress-inform", Pharmaceutical Chemistry Textbook 4th Edition, p. 11 (4 pages).

* cited by examiner

2,3-DIHYDRO-4H-BENZO[B][1,4]OXAZIN-4-YL)(5-(PHENYL)-PYRIDIN-3-YL)METHANONE DERIVATIVES AND SIMILAR COMPOUNDS AS CYP11A1 INHIBITORS FOR THE TREATMENT OF PROSTATE CANCER

This is a National Stage Application under 35 U.S.C. § 371 of International Patent Application No. PCT/FI2021/050828, filed Nov. 30, 2021, which claims the benefit of priority of Finnish Patent Application No. 20206226, filed Dec. 1, 2020, both of which are incorporated herein by reference.

TECHNICAL FIELD

The present invention relates to therapeutically active compounds useful in the treatment of a steroid receptor, such as androgen receptor (AR) or estrogen receptor (ER), dependent conditions and diseases, and to pharmaceutical compositions containing such compounds.

BACKGROUND OF THE INVENTION

Treatments for steroid receptor dependent diseases such as androgen receptor (AR) dependent cancers and estrogen receptor (ER) dependent cancers have been investigated extensively. Prostate cancer, for example, is worldwide one of the most common cancers in men. Even though the 5-year survival rate of patients with localized prostate cancer is high, the prognosis for those patients, who develop castration-resistant prostate cancer (CRPC) within that 5-year follow-up period, is poor.

The androgen receptor (AR) signalling axis is critical in all stages of prostate cancer. In the CRPC stage (castration resistant prostate cancer), disease is characterized by high AR expression, AR amplification and persistent activation of the AR signalling axis by residual tissue/tumor androgens and by other steroid hormones and intermediates of steroid biosynthesis. Thus, treatment of advanced prostate cancer involves androgen deprivation therapy (ADT) such as hormonal manipulation using gonadotropin-releasing hormone (GnRH) agonists/antagonists or surgical castration, AR antagonists or CYP17A1 inhibitors (such as abiraterone acetate in combination with prednisone).

Although therapies can initially lead to disease regression, eventually majority of the patients develop a disease that is refractory to currently available therapies. Increased progesterone levels in patients treated with abiraterone acetate has been hypothesized to be one of the resistance mechanisms. Several nonclinical and clinical studies have indicated upregulation of enzymes that catalyse steroid biosynthesis at the late stage of CRPC. Very recently it has been published that 11(3-OH androstenedione can be metabolized into 11-ketotestosterone (11-K-T) and 11-ketodehydrotestosterone (11-K-DHT) which can bind and activate AR as efficiently as testosterone and dihydrotestosterone. It has been shown that these steroids are found in high levels in plasma and tissue in prostate cancer patients, suggesting their role as AR agonists in CRPC. Furthermore, it has been addressed that prostate cancer resistance to CYP17A1 inhibition may still remain steroid dependent and responsive to therapies that can further suppress de novo intratumoral steroid synthesis upstream of CYP17A1, such as by CYP11A1 inhibition therapy (Cai, C. et al, Cancer Res., 71(20), 6503-6513, 2011).

Cytochrome P450 monooxygenase 11A1 (CYP11A1), also called cholesterol side chain cleavage enzyme, is a mitochondrial monooxygenase which catalyses the conversion of cholesterol to pregnenolone, the precursor of all steroid hormones. By inhibiting CYP11A1, the key enzyme of steroid biosynthesis upstream of CYP17A1, the total block of the whole steroid biosynthesis can be achieved. CYP11A1 inhibitors may therefore have a great potential for treating steroid hormone dependent cancers, including prostate cancer, even in advanced stages of the disease, and especially in those patients who appear to be hormone refractory. It has been shown that a compound having CYP11A1 inhibitory effect significantly inhibited tumor growth in vivo in a murine CRPC xenograft model (Oksala, R. et al, Annals of Oncology, (2017) 28 (suppl. 5): Abstract/Poster 28P). CYP11A1 inhibitors have been described earlier in WO 2018/115591.

SUMMARY OF THE INVENTION

It has been found that compounds of formula (I) are potent CYP11A1 inhibitors. The compounds of the invention are therefore particularly useful as medicaments in the treatment of steroid hormone dependent conditions and diseases where CYP11A1 inhibition is desired. Such conditions and diseases include, but are not limited to, endocrine cancers and diseases, such as prostate cancer and breast cancer. In particular, the compounds of the invention are useful in the treatment of AR dependent conditions and diseases including prostate cancer.

The present invention relates to a compound of formula (I) or a pharmaceutically acceptable salt thereof.

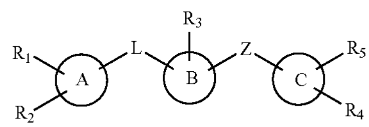

(I)

wherein

B is any of the following groups

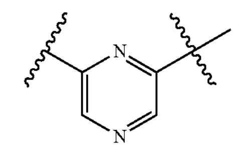

(1)

,

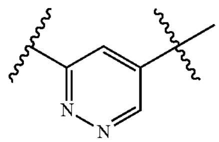

(2)

or

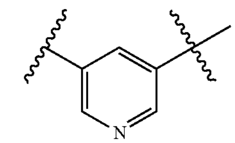

(3)

;

wherein when B is group (1) or (2) then

A is a 3-10 membered carbocyclic ring or a 4-12 membered heterocyclic ring containing 1-4 heteroatoms selected from O, N or S;

C is any of the following groups (1′)

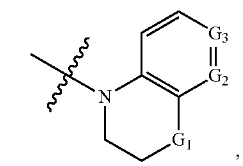

, (2′)

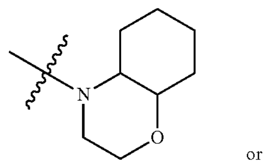

or (3′)

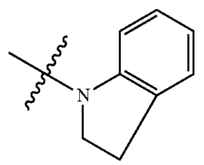

;

$G_1$ is $CH_2$, NH or O;

$G_2$ and $G_3$ are, independently, is CH or N;

Z is —C(O)—, —$SO_2$—, —$C_{1-3}$ alkyl- or —$CH_2$—C(O)—;

L is a bond, —$C_{1-7}$alkyl- or —$C_{1-7}$alkenyl-;

$R_1$ is hydrogen, $C_{1-7}$ alkyl, $C_{1-7}$ alkoxy, halogen, hydroxy, nitro, halogen $C_{1-7}$ alkyl, hydroxy $C_{1-7}$ alkyl, —O-halogen $C_{1-7}$ alkyl or —X—$NR_6R_7$;

$R_2$ is hydrogen, hydroxy, $C_{1-7}$ alkyl or halogen;

$R_3$ is hydrogen, $C_{1-7}$ alkyl or amino;

$R_4$ is hydrogen, $C_{1-7}$ alkyl, $C_{1-7}$ alkoxy, halogen, hydroxy, hydroxy $C_{1-7}$ alkyl, halogen $C_{1-7}$ alkyl or —C(O)—O—$C_{1-7}$ alkyl;

$R_5$ is hydrogen, halogen, $C_{1-7}$ alkoxy or $C_{1-7}$ alkyl;

X is a bond or $C_{1-7}$ alkyl;

$R_6$ and $R_7$ are, independently, hydrogen or $C_{1-7}$ alkyl;

wherein when B is group (3) then

A is any one of the following groups (1″)

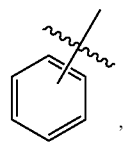

, (2″)

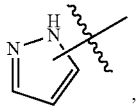

, (3″)

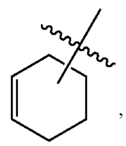

,

-continued (4″)

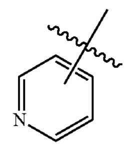

, (5″)

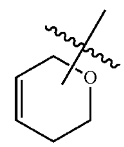

, (6″)

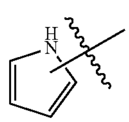

, (7″)

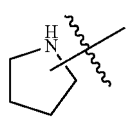

, (8″)

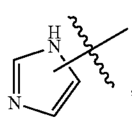

, (9″)

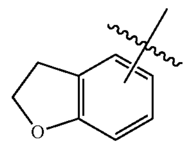

, (10″)

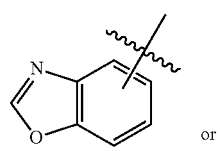

or (11″)

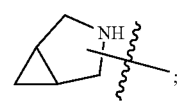

;

provided that when C is ring (3') then A is not ring (2") or ring (7"); C is any of the following groups (1′)

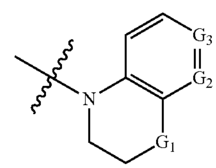

, (2′)

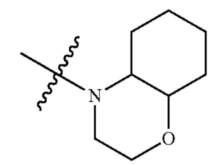

,

-continued (3')

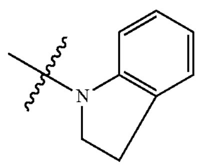

or (4')

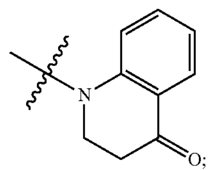

$G_1$ is $CH_2$, NH or O;

$G_2$ and $G_3$ are, independently, is CH or N;

Z is —C(O)—, —$SO_2$—, —$C_{1-3}$ alkyl- or —$CH_2$—C(O)—;

L is a bond, —$C_{1-7}$ alkyl- or —$C_{1-7}$ alkenyl-;

$R_1$ is hydrogen, $C_{1-7}$ alkyl, $C_{1-7}$ alkoxy, halogen, hydroxy, halogen $C_{1-7}$ alkyl, hydroxy $C_{1-7}$ alkyl, —O-halogen $C_{1-7}$ alkyl, —X—$NR_6R_7$, $R_2$ is hydrogen, hydroxy, $C_{1-7}$ alkyl or halogen;

$R_3$ is hydrogen, $C_{1-7}$ alkyl or amino;

$R_4$ is hydrogen, $C_{1-7}$ alkyl, $C_{1-7}$ alkoxy, halogen, hydroxy $C_{1-7}$ alkyl, halogen $C_{1-7}$ alkyl or —C(O)—O—$C_{1-7}$ alkyl;

$R_5$ is hydrogen, halogen, $C_{1-7}$ alkoxy or $C_{1-7}$ alkyl;

X is a bond or $C_{1-7}$ alkyl;

$R_6$ and $R_7$ are, independently, hydrogen or $C_{1-7}$ alkyl;

with the proviso that compound of formula (I) is not (7-Methoxy-2,3-dihydro-4H-benzo[b][1,4]oxazin-4-yl)(6-(pyrrolidin-1-yl)-pyrazin-2-v)methanone;

(8-Fluoro-3,4-dihydro-3-hydroxymethyl-1(2H)-quinolinyl)(6-(1-pyrrolidinyl)-2-pyrazinyl)methanone;

(3,4-Dihydro-3-methoxy-1(2H)-quinolinyl)(6-phenyl-4-pyridazinyl)methanone;

(6-Fluoro-3,4-dihydro-4-methyl-1(2H)-quinoxalinyl)(5-phenyl-3-pyridinyl)-methanone;

(3,4-Dihydro-1(2H)-quinolinyl)(5-phenyl-3-pyridinyl)methanone;

(5-(2,3-Dihydro-5-benzofuranyl)-3-pyridinyl)(3,4-dihydro-1(2H)-quinolinyl)-methanone;

(5-(2,3-Dihydro-5-benzofuranyl)-3-pyridinyl)(7-fluoro-2,3-dihydro-4H-1,4-benzoxazin-4-yl)methanone;

(6,8-Difluoro-3,4-dihydro-1(2H)-quinolinyl)(5-(4-(dimethylamino)phenyl)-3-pyridinyl)methanone;

(3,4-Dihydro-1(2H)-quinolinyl)(5-(1-pyrrolidinyl)-3-pyridinyl)methanone;

(5-(2,3-Dihydro-5-benzofuranyl)-3-pyridinyl)(octahydro-4H-1,4-benzoxazin-4-yl)methanone;

(5-(4-Methoxyphenyl)-3-pyridinyl)(octahydro-4H-1,4-benzoxazin-4-yl)-methanone; or (2,3-Dihydro-1H-indol-1-yl)(5-phenyl-3-pyridinyl)methanone.

According to one embodiment, the invention provides a method for the treatment of a steroid receptor dependent condition or disease comprising administering to a subject in need thereof a therapeutically effective amount of a compound of formula (I) or a pharmaceutically acceptable salt thereof (I)

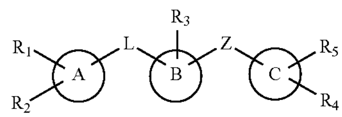

wherein

A is a 3-10 membered carbocyclic ring or a 4-12 membered heterocyclic ring containing 1-4 heteroatoms selected from O, N or S;

B is any of the following groups (1)

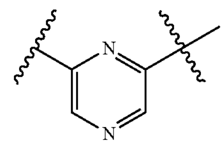

, (2)

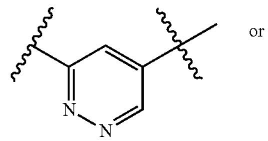

or (3)

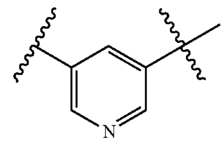

;

C is any of the following groups (1')

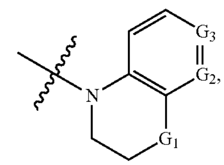

(2')

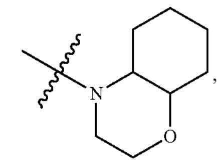

, (3')

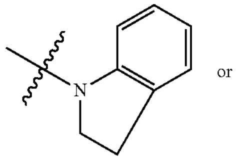

or (4')

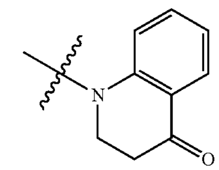

$G_1$ is $CH_2$, NH or O;

$G_2$ and $G_3$ are, independently, is CH or N;
Z is —C(O)—, —$SO_2$—, —$C_{1-3}$ alkyl- or —$CH_2$—C(O)—;
L is a bond, —$C_{1-7}$ alkyl- or —$C_{1-7}$ alkenyl-;
$R_1$ is hydrogen, $C_{1-7}$ alkyl, $C_{1-7}$ alkoxy, halogen, hydroxy, nitro, halogen $C_{1-7}$ alkyl,
hydroxy $C_{1-7}$ alkyl, —O-halogen $C_{1-7}$ alkyl or —X—$NR_6R_7$;
$R_2$ is hydrogen, hydroxy, $C_{1-7}$ alkyl or halogen;
$R_3$ is hydrogen, $C_{1-7}$ alkyl or amino;
$R_4$ is hydrogen, $C_{1-7}$ alkyl, $C_{1-7}$ alkoxy, halogen, hydroxy, hydroxy $C_{1-7}$ alkyl,
halogen $C_{1-7}$ alkyl or —C(O)—O—$C_{1-7}$ alkyl;
$R_5$ is hydrogen, halogen, $C_{1-7}$ alkoxy or $C_{1-7}$ alkyl;
X is a bond or $C_{1-7}$ alkyl;
$R_6$ and $R_7$ are, independently, hydrogen or $C_{1-7}$ alkyl.

According to one embodiment, the steroid receptor dependent conditions or diseases include, but are not limited to, endocrine cancers and diseases, such as prostate cancer, particularly castration resistant prostate cancer (CRPC), and breast cancer.

According to one embodiment, the invention provides a pharmaceutical composition comprising a compound of formula (I) together with a pharmaceutically acceptable carrier.

DETAILED DESCRIPTION OF THE INVENTION

The present application provides novel compounds of formula (I) or pharmaceutically acceptable salts thereof which are useful as CYP11A1 inhibitors.

One of the embodiments of the present invention provides a compound of formula (I) or a pharmaceutically acceptable salt thereof (I)

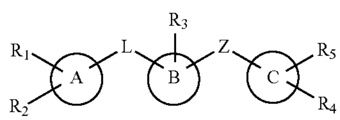

wherein
B is any of the following groups (1)

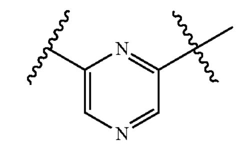

, (2)

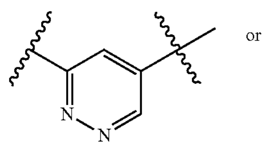

or (3)

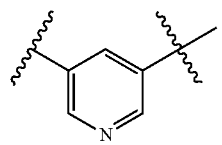

;

wherein when B is group (1) or (2) then
A is a 3-10 membered carbocyclic ring or a 4-12 membered heterocyclic ring containing 1-4 heteroatoms selected from O, N or S;
C is any of the following groups (1′)

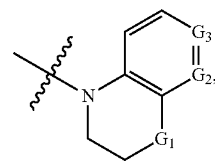

(2′)

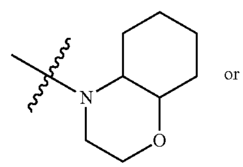

or (3′)

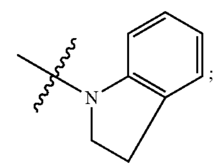

;

$G_1$ is $CH_2$, NH or O;
$G_2$ and $G_3$ are, independently, is CH or N;
Z is —C(O)—, —$SO_2$—, —$C_{1-3}$ alkyl- or —$CH_2$—C(O)—;
L is a bond, —$C_{1-7}$alkyl- or —$C_{1-7}$alkenyl-;
$R_1$ is hydrogen, $C_{1-7}$ alkyl, $C_{1-7}$ alkoxy, halogen, hydroxy, nitro, halogen $C_{1-7}$ alkyl,
hydroxy $C_{1-7}$ alkyl, —O-halogen $C_{1-7}$ alkyl or —X—$NR_6R_7$;
$R_2$ is hydrogen, hydroxy, $C_{1-7}$ alkyl or halogen;
$R_3$ is hydrogen, $C_{1-7}$ alkyl or amino;
$R_4$ is hydrogen, $C_{1-7}$ alkyl, $C_{1-7}$ alkoxy, halogen, hydroxy, hydroxy $C_{1-7}$ alkyl,
halogen $C_{1-7}$ alkyl or —C(O)—O—$C_{1-7}$ alkyl;
$R_5$ is hydrogen, halogen, $C_{1-7}$ alkoxy or $C_{1-7}$ alkyl;
X is a bond or $C_{1-7}$ alkyl;
$R_6$ and $R_7$ are, independently, hydrogen or $C_{1-7}$ alkyl;
wherein when B is group (3) then
A is any one of the following groups (1″)

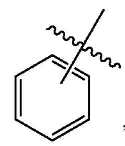

, (2″)

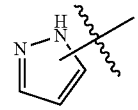

, (3″)

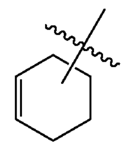

,

-continued (4″)

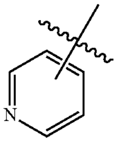

, (5″)

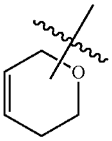

, (6″)

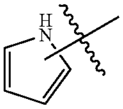

, (7″)

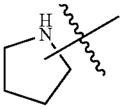

, (8″)

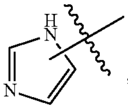

, (9″)

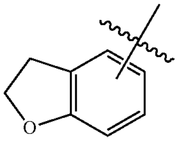

, (10″)

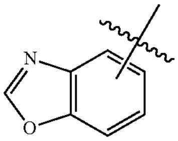

or (11″)

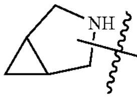

;

provided that when C is ring (3') then A is not ring (2") or ring (7");

C is any of the following groups (1′)

(2′)

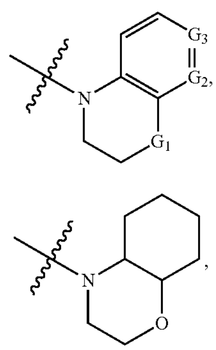

-continued (3′)

(4′)

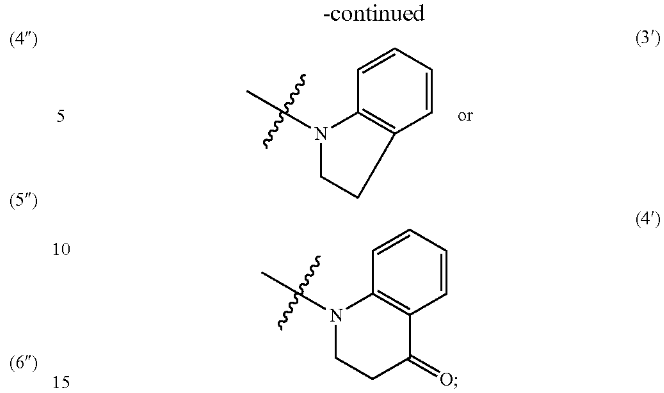

$G_1$ is $CH_2$, NH or O;

$G_2$ and $G_3$ are, independently, is CH or N;

Z is —C(O)—, —$SO_2$—, —$C_{1-3}$ alkyl- or —$CH_2$—C(O)—;

L is a bond, —$C_{1-7}$ alkyl- or —$C_{1-7}$ alkenyl-;

$R_1$ is hydrogen, $C_{1-7}$ alkyl, $C_{1-7}$ alkoxy, halogen, hydroxy, halogen $C_{1-7}$ alkyl, hydroxy $C_{1-7}$ alkyl, —O-halogen $C_{1-7}$ alkyl, —X—$NR_6R_7$, $R_2$ is hydrogen, hydroxy, $C_{1-7}$ alkyl or halogen;

$R_3$ is hydrogen, $C_{1-7}$ alkyl or amino;

$R_4$ is hydrogen, $C_{1-7}$ alkyl, $C_{1-7}$ alkoxy, halogen, hydroxy $C_{1-7}$ alkyl, halogen $C_{1-7}$ alkyl or —C(O)—O—$C_{1-7}$ alkyl;

$R_5$ is hydrogen, halogen, $C_{1-7}$ alkoxy or $C_{1-7}$ alkyl;

X is a bond or $C_{1-7}$ alkyl;

$R_6$ and $R_7$ are, independently, hydrogen or $C_{1-7}$ alkyl;

with the proviso that compound of formula (I) is not (7-Methoxy-2,3-dihydro-4H-benzo[b][1,4]oxazin-4-yl)(6-(pyrrolidin-1-yl)-pyrazin-2-yl)methanone;

(8-Fluoro-3,4-dihydro-3-hydroxymethyl-1(2H)-quinolinyl)(6-(1-pyrrolidinyl)-2-pyrazinyl)methanone;

(3,4-Dihydro-3-methoxy-1(2H)-quinolinyl)(6-phenyl-4-pyridazinyl)methanone;

(6-Fluoro-3,4-dihydro-4-methyl-1(2H)-quinoxalinyl)(5-phenyl-3-pyridinyl)-methanone;

(3,4-Dihydro-1(2H)-quinolinyl)(5-phenyl-3-pyridinyl)methanone;

(5-(2,3-Dihydro-5-benzofuranyl)-3-pyridinyl)(3,4-dihydro-1(2H)-quinolinyl)-methanone;

(5-(2,3-Dihydro-5-benzofuranyl)-3-pyridinyl)(7-fluoro-2,3-dihydro-4H-1,4-benzoxazin-4-yl)methanone;

(6,8-Difluoro-3,4-dihydro-1(2H)-quinolinyl)(5-(4-(dimethylamino)phenyl)-3-pyridinyl)methanone;

(3,4-Dihydro-1(2H)-quinolinyl)(5-(1-pyrrolidinyl)-3-pyridinyl)methanone;

(5-(2,3-Dihydro-5-benzofuranyl)-3-pyridinyl)(octahydro-4H-1,4-benzoxazin-4-yl)methanone;

(5-(4-Methoxyphenyl)-3-pyridinyl)(octahydro-4H-1,4-benzoxazin-4-yl)-methanone or (2,3-Dihydro-1H-indol-1-yl)(5-phenyl-3-pyridinyl)methanone.

It is to be understood that the left bond of Z is attached to the ring B of formula (I). The wavy line in group A denotes the site of attachment to L. The wavy line in group C denotes the site of attachment to Z. The left wavy line in group B denotes the site of attachment to L and the right wavy line in group B denotes the site of attachment to Z.

According to one embodiment, specifically provided is a compound according to formula (I) wherein B is group (1) or group (3), for example B is group (1), or as another example B is group (3).

According to yet one embodiment, specifically provided are compounds according to any of the above embodiments wherein Z is —C(O)—, —$SO_2$—, —$CH_2$— or —$CH_2$—C(O)—. According to another embodiment, specifically provided are compounds according to any of the above embodiments wherein Z is —C(O)—. According to yet one embodiment, specifically provided are compounds according to any of the above embodiments wherein L is a bond, —$C_{1-3}$ alkyl- or —$C_{1-3}$ alkenyl-. In a subgroup of the preceding embodiment L is a bond, —$CH_2$— or —$C(CH_2)$—. According to yet one embodiment, specifically provided are compounds according to any of the above embodiments wherein L is a bond. According to yet one embodiment, specifically provided are compounds according to any of the above embodiments wherein C is group (1') or (2'). According to yet one embodiment, specifically provided are compounds according to any of the above embodiments wherein C is group (1').

According to yet one embodiment, specifically provided are compounds according to any of the above embodiments wherein $G_1$ is $CH_2$ or O, for example $G_1$ is $CH_2$ or as another example $G_1$ is O. In one aspect, provided are compounds according to any of the above embodiments wherein $G_2$ is N and $G_3$ is CH, or wherein $G_2$ is CH and $G_3$ is N.

According to one embodiment, specifically provided are compounds according to any of the above embodiments wherein $R_1$ is hydrogen, $C_{1-7}$ alkyl, $C_{1-7}$ alkoxy, halogen, hydroxy $C_{1-7}$ alkyl or halogen $C_{1-7}$ alkyl. According to another embodiment, specifically provided are compounds according to any of the above embodiments wherein $R_z$ is hydrogen, hydroxy, $C_{1-7}$ alkyl or halogen. According to another embodiment, specifically provided are compounds according to any of the above embodiments wherein $R_3$ is hydrogen. According to another embodiment, specifically provided are compounds according to any of the above embodiments wherein $R_4$ is hydrogen, $C_{1-7}$ alkyl, halogen or —C(O)—O—$C_{1-7}$ alkyl.

According to one embodiment, specifically provided is a compound according to any of the above embodiments of formula (I) wherein when B is group (3) then A is any one of the following groups:

(1″)

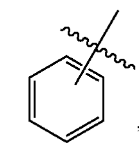

, (2a)

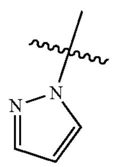

, (2b)

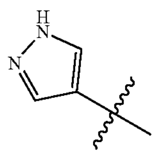

,

-continued (3a)

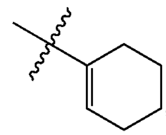

, (4a)

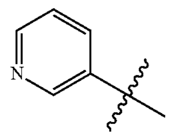

, (4b)

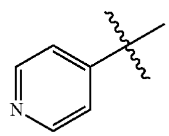

, (5″)

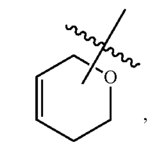

, (6a)

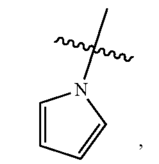

, (7a)

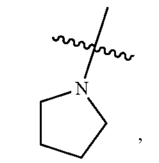

, (8a)

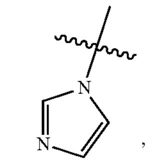

, (9a)

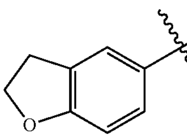

, (9b)

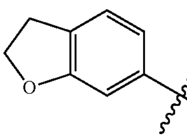

, (10a)

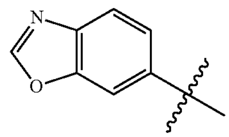

or

-continued (11a)

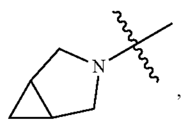

$R_1$ and $R_2$ being attached to the above A-rings, and the wavy line denoting the site of attachment to L.

According to one embodiment, specifically provided is a compound according to any of the above embodiments of formula (I) wherein when B is group (1) or (2) then A is any one of the following groups:

(1″)

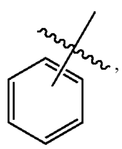

(2″)

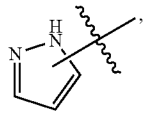

(3″)

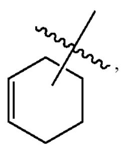

(4″)

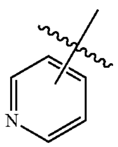

(5″)

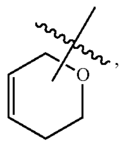

(6″)

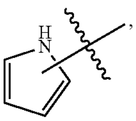

(7″)

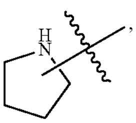

(8″)

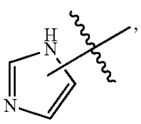

-continued (9″)

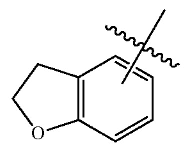

(10″)

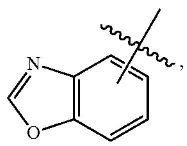

(11″)

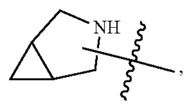

(12″)

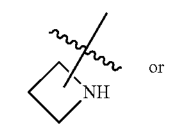

or (13″)

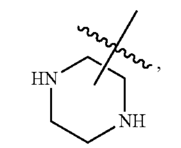

$R_1$ and $R_2$ being attached to the above A-rings, and the wavy line denoting the site of attachment to L.

In a subclass of the above embodiment are compounds wherein A is any one of the following groups:

(1″)

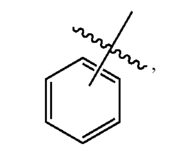

(2a)

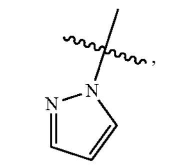

(2b)

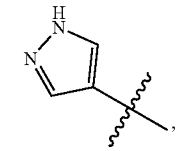

(3a)

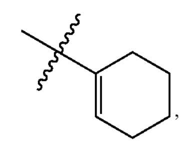

-continued (4a)

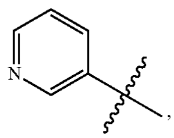

(4b)

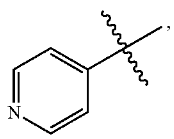

(5″)

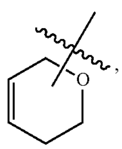

(6a)

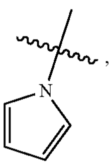

(7a)

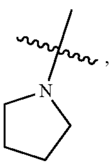

(8a)

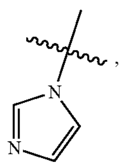

(9a)

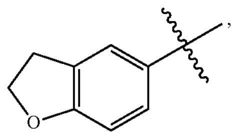

(9b)

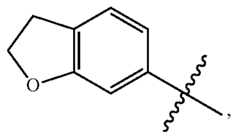

(10a)

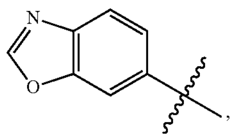

(11a)

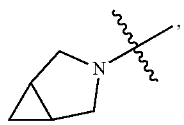

-continued (12a)

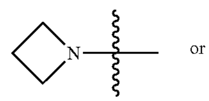

or (13a)

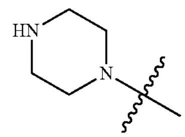

$R_1$ and $R_2$ being attached to the above A-rings, and the wavy line denoting the site of attachment to L.

According to one embodiment, specifically provided is a compound according to any of the above embodiments of formula (I) wherein A is group (1"), (2"), (3"), (6"), (8"), (9") or (10").

According to one embodiment, specifically provided is a compound according to any of the above embodiments of formula (I) wherein A is group (1"), (2a), (2b), (3a), (6a), (8a), (9b) or (10a).

According to one embodiment, the compound of the present invention is represented by formula (IA) or a pharmaceutically acceptable salt thereof (IA)

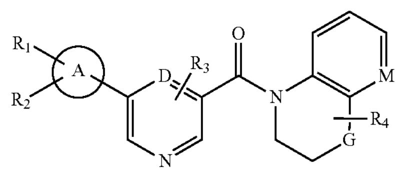

wherein

D is N or CH;

G is $CH_2$, NH or O;

M is CH or N;

$R_1$ is hydrogen, $C_{1-7}$ alkyl, $C_{1-7}$ alkoxy or halogen;

$R_2$ is hydrogen or halogen;

$R_3$ is hydrogen or $C_{1-7}$ alkyl;

$R_4$ is hydrogen, $C_{1-7}$ alkyl, halogen or —C(O)—O—$C_{1-7}$ alkyl;

A is any one of the following groups:

(1″)

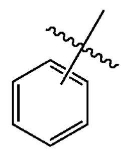

(2a)

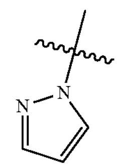

-continued (2b)

(3a)

(6a)

(8a)

(9b)

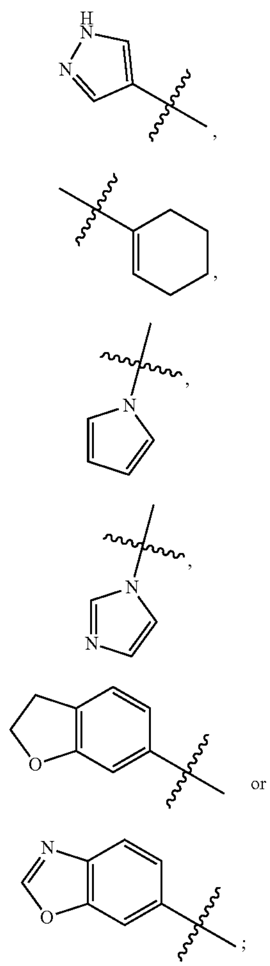

or (10a)

with the proviso that compound of formula (I) is not (3,4-Dihydro-1(2H)-quinolinyl)(5-phenyl-3-pyridinyl) methanone;

(5-(2,3-Dihydro-5-benzofuranyl)-3-pyridinyl)(3,4-dihydro-1(2H)-quinolinyl)-methanone or (5-(2,3-Dihydro-5-benzofuranyl)-3-pyridinyl)(7-fluoro-2,3-dihydro-4H-1,4-benzoxazin-4-yl)methanone.

In a subclass of the above embodiment are compounds of formula (IA), wherein $R_1$ is hydrogen, methyl, methoxy or halogen; $R_3$ is hydrogen or methyl; $R_4$ is hydrogen, methyl or halogen; and A is group (1"), (2a), (3a), (9b) or (10a).

According to still one embodiment, the present invention provides a method for the treatment of a steroid receptor dependent conditions and diseases, comprising administering to a subject in need thereof a therapeutically effective amount of a compound of formula (I) as defined in any of the above embodiments.

According to one embodiment, the steroid receptor dependent disease or condition is androgen receptor or estrogen receptor dependent disease or condition including endocrine cancers and diseases, for example prostate cancer or breast cancer, particularly castration-resistant prostate cancer (CRPC). According to one embodiment of the invention, the CRPC to be treated is refractory to CYP17A1 inhibitor treatment. According to another embodiment, the androgen receptor dependent disease or condition is endocrine cancer which is dependent upon CYP11A1 activation.

The compounds of the invention can be prepared by a variety of synthetic routes analogously to the methods known in the literature using suitable starting materials. The compounds according to formula (I) can be prepared e.g. analogously or according to the following reaction Schemes. Some compounds included in the formula (I) can be obtained by converting the functional groups of the other compounds of formula (I) obtained in accordance with the following Schemes, by well known reaction steps such as oxidation, reduction, hydrolysis, acylation, alkylation, amidation, amination, sulfonation and others. It should be noted that any appropriate leaving groups, e.g. N-protecting groups, such as a t-butoxycarbonyl (t-BOC) group or a phenylsulfonyl group, can be used in well known manner during the syntheses in order to improve the selectivity of the reaction steps.

Compounds of formula (I) wherein L is a bond can be prepared according to Scheme 1, wherein wherein X is a halogen, preferably chloro or bromo, and A, B, C, Z, $R_1$, $R_2$, $R_3$, $R_4$ and $R_5$ are as defined above. In the method of Scheme 1, the compound of formula [1] is coupled with a boronic acid derivative of formula [2] in a suitable solvent, such as a mixture of ethanol, toluene and water, in the presence of a base such as sodium carbonate and a catalyst such as bis(triphenylphosphine)palladium (II) dichloride at elevated temperature to produce a compound of formula [Ta]. Instead of boronic acid derivative [2] a corresponding boronic ester such as boronic acid pinacol ester can also be used.

SCHEME 1.

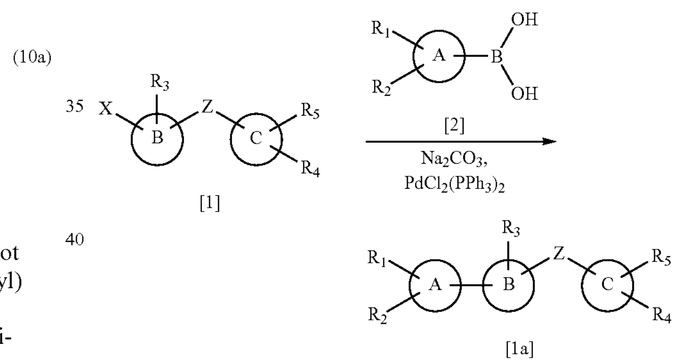

Compounds of formula (I) wherein Z is —C(O)— can also be prepared according to Scheme 2, wherein A, B, C, L, $R_1$, $R_2$, $R_3$, $R_4$ and $R_5$ are as defined above (for clarity, the ring nitrogen atom of compound [4] is depicted in Scheme 2) and $R_6$ is methyl or ethyl. In the method of Scheme 2, the compound of formula [3] is coupled with a compound of formula [4] in a suitable solvent such as toluene in the presence of trimethylaluminum and a base such as triethylamine (TEA) to produce a compound of formula [Ib].

SCHEME 2.

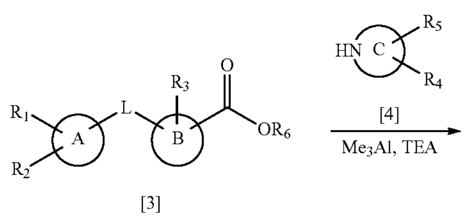

-continued

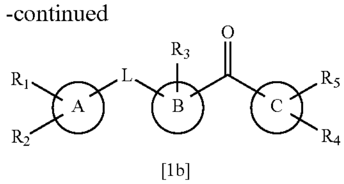

[1b]

Alternatively, compounds of formula (I) wherein Z is —C(O)— can be prepared according to Scheme 3, wherein A, B, C, L, $R_1$, $R_2$, $R_3$, $R_4$ and $R_5$ are as defined above (for clarity, the ring nitrogen atom of compound [4] is depicted in Scheme 3). In the method of Scheme 3, the compound of formula [5] is coupled with a compound of formula [4] in a suitable solvent such as DMF in the presence of a base such as triethylamine (TEA) and optionally a coupling reagent such as propylphosphonic anhydride ($T_3P$) to produce a compound of formula [Ib].

SCHEME 3.

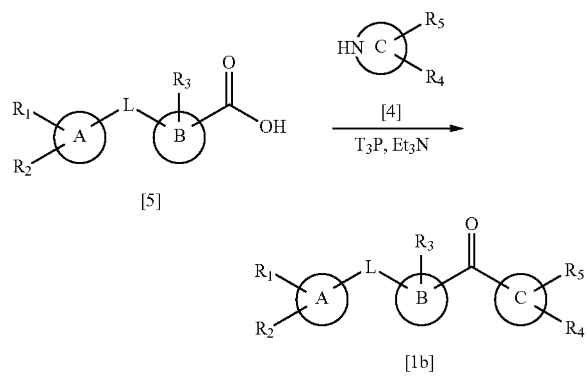

[5]

[1b]

Alternatively, compounds of formula (I) wherein Z is —C(O)— can be prepared according to Scheme 4, wherein A, B, C, L, $R_1$, $R_2$, $R_3$, $R_4$ and $R_5$ are as defined above (for clarity, the ring nitrogen atom of compound [4] is depicted in Scheme 4). In the method of Scheme 4, the compound of formula [6] is coupled with a compound of formula [4] in a suitable solvent such as DCM in the presence of a base such as triethylamine (TEA) to produce a compound of formula [Ib].

SCHEME 4.

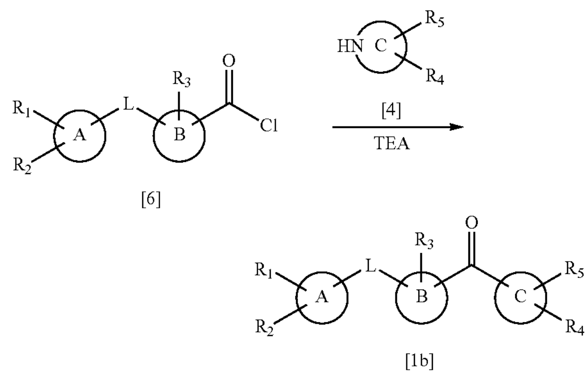

[6]

[1b]

Compounds of formula (I) wherein L is a bond and A contains a —NH group (for example A is pyrrolidine, imidazole or pyrazole) can also be prepared according to Scheme 5, wherein X is a halogen, preferably chloro or bromo, and A, B, C, Z, $R_1$, $R_2$, $R_3$, $R_4$ and $R_5$ are as defined above (for clarity, the ring nitrogen atom of compound [7] is depicted in Scheme 5). In the method of Scheme 5, the compound of formula [1] can be coupled with a compound of formula [7] in a suitable solvent such as dry toluene or dry DMSO in the presence of a base such as sodium tert-butoxide (STB), DIPEA or potassium phosphate and optionally a catalyst such as tris(dibenzylideneacetone)di-palladium $Pd_2(dba)_3$ at elevated temperature to produce a compound of formula [Ia].

SCHEME 5.

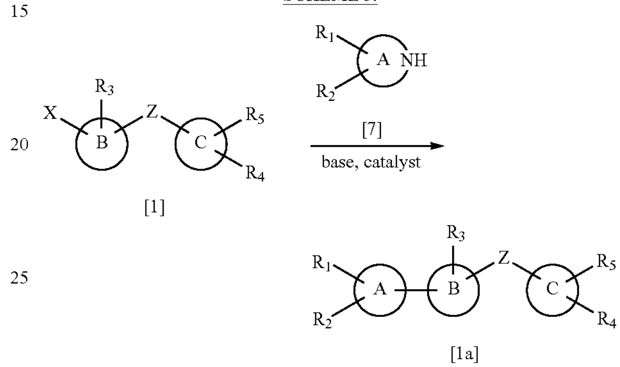

[1]

[1a]

Compounds of formula (I) wherein Z is —$CH_2$—C(O)— can also be prepared according to Scheme 6, wherein A, B, C, L, $R_1$, $R_2$, $R_3$, $R_4$ and $R_5$ are as defined above (for clarity, the ring nitrogen atom of compound [4] is depicted in Scheme 6). In the method of Scheme 6, the compound of formula [8] is coupled with a compound of formula [4] in a suitable solvent such as DMF in the presence of a base such as trimethylamine (TMA) and optionally a coupling reagent such as propylphosphonic anhydride ($T_3P$) and to produce a compound of formula [Ic].

SCHEME 6.

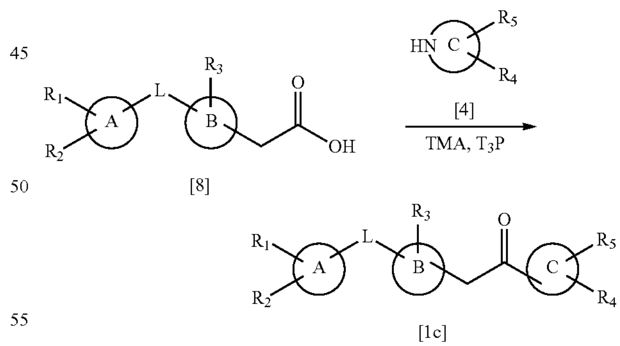

[8]

[1c]

Compounds of formula (I) wherein Z is —$C_{1-3}$ alkyl- can also be prepared according to Scheme 7, wherein A, B, C, L, $R_1$, $R_2$, $R_3$, $R_4$ and $R_5$ are as defined above (for clarity, the ring nitrogen atom of compound [4] is depicted in Scheme 7). In the method of Scheme 7, the aldehyde compound of formula [9] is reacted with a compound of formula [4] in a suitable solvent such as 1,2-dichloroethane in the presence of acetic acid and a reducing agent such as sodium triacetoxy borohydride (STAB) to produce a compound of formula [Id].

SCHEME 7.

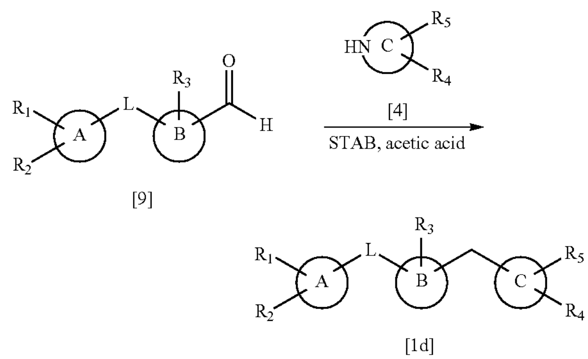

[9]

[1d]

Intermediate compounds can be prepared according to the methods disclosed in the literature or as disclosed in the present disclosure.

For example, intermediate compounds of formula [1a] can be prepared according to Scheme 8, wherein B, C, $R_3$, $R_4$ and $R_5$ are as defined above, and X and Y are halogen, preferably chloro or bromo (for clarity, the ring nitrogen atom of compound [4] is depicted in Scheme 8). In the method of Scheme 8, a compound of formula [10] is coupled with a compound of formula [4] in a suitable solvent such as DCM in the presence of a base such as TEA to produce a compound of formula [1a].

SCHEME 8.

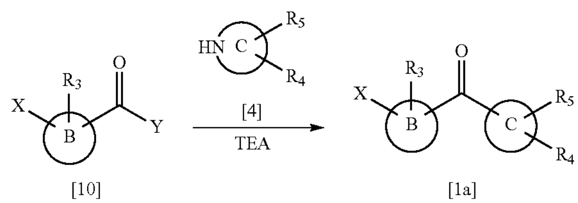

[10]

[1a]

Intermediate compounds of formula [3a] wherein A contains a —NH group (for example A is pyrrolidine, imidazole or pyrazole) can be prepared, for example, according to Scheme 9, wherein A, B, $R_1$, $R_3$, $R_2$ and $R_3$ are as defined above, and X is halogen, preferably chloro or bromo (for clarity, the ring nitrogen atom of compound [7] is depicted in Scheme 9). In the method of Scheme 9, a compound of formula [11] is coupled with a compound of formula [7] in a suitable solvent such as toluene-dioxane in the presence of a base such as potassium phosphate and a catalyst such as the mixture of tris(dibenzylideneacetone)dipalladium and 2-di-tert-butylphosphino-3,4,5,6-tetramethyl-2',4',6'-triisopropyl-1,1'-biphenyl to produce a compound of formula [3a].

SCHEME 9.

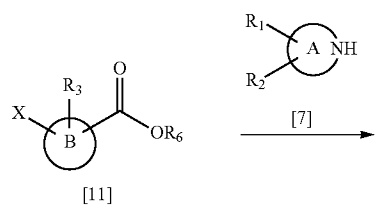

[11]

-continued

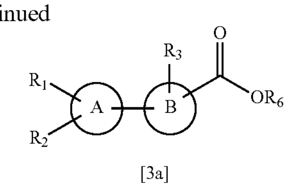

[3a]

Intermediate compounds of formula [5a] can be prepared, for example, according to Scheme 10, wherein A, B, $R_1$, $R_2$ and $R_3$ are as defined above, X is halogen, preferably chloro or bromo, and $R_6$ is methyl or ethyl. In the method of Scheme 10, a compound of formula [11] is coupled with a compound of formula [2] in a suitable solvent such as acetonitrile/ethanol/water in the presence of a base such as sodium carbonate and a catalyst such as $PdCl_2(PPh_3)_2$ at elevated temperature to produce a compound of formula [3a].

SCHEME 10.

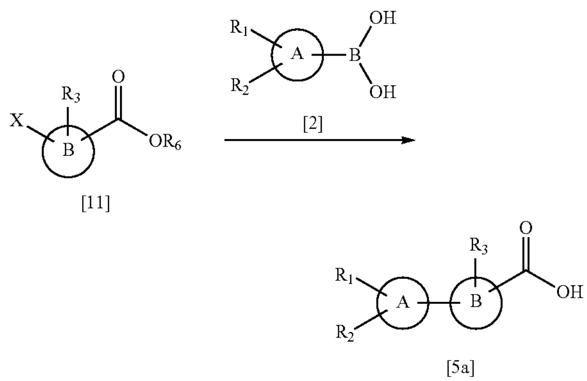

[11]

[5a]

Intermediate compounds of formula [8a] can be prepared, for example, according to Scheme 11, wherein A, B, $R_1$, $R_2$, $R_3$ are as defined above, and X is halogen, preferably chloro or bromo. In the method of Scheme 11, a compound of formula [12] is coupled with a compound of formula [2] in a suitable solvent such as DME-water in the presence of a base such as cesium carbonate and a catalyst such as added tetrakis(triphenylphosphine)palladium to produce a compound of formula [8a].

SCHEME 11.

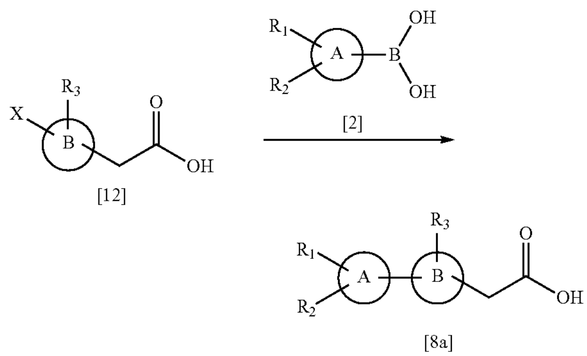

[12]

[8a]

Alternatively, the compounds of formula (I) can be prepared as disclosed in the specific Examples of the present disclosure.

Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "subject", as employed herein, refers to humans and animals.

The term "steroid receptor" refers to receptor which binds to and is activated by a steroid hormone. Examples of steroid receptors include, but are not limited to, androgen, estrogen, glucocorticoid, and progesterone receptors.

The term "endocrine cancer" refers to partially or completely unregulated growth of one or more cellular components of the endocrine system, including, but not limited to, cancers of one or more of the adrenal glands.

The term "elevated temperature" refers to a temperature higher than room temperature, typically from about 30 to about 120° C., from example from about 40 to about 100° C. or from about 50 to about 80° C.

The term "halo" or "halogen", as employed herein as such or as part of another group, refers to chlorine, bromine, fluorine or iodine.

The term "$C_{1-7}$ alkyl", as employed herein as such or as part of another group, refers to a straight or branched chain saturated hydrocarbon group having 1, 2, 3, 4, 5, 6 or 7 carbon atom(s). Representative examples of $C_{1-7}$ alkyl include, but are not limited to, methyl, ethyl, n-propyl, iso-propyl, n-butyl, iso-butyl, sec-butyl, tert-butyl, n-pentyl, iso-pentyl and n-hexyl. One preferred embodiment of "$C_{1-7}$ alkyl" is $C_{1-3}$ alkyl. The term "$C_{1-3}$ alkyl" refers to a preferred embodiment of "$C_{1-7}$ alkyl" having 1, 2 or 3 carbon atoms.

The term "$C_{2-7}$ alkenyl", as employed herein as such or as part of another group, refers to an aliphatic hydrocarbon group having 2, 3, 4, 5, 6 or 7 carbon atoms and containing one or several double bonds. Representative examples include, but are not limited to, ethenyl, propenyl and cyclohexenyl.

The term "$C_{3-7}$ cycloalkyl", as employed herein as such or as part of another group, refers to a saturated cyclic hydrocarbon group containing 3, 4, 5, 6 or 7 carbon atoms. Representative examples of cycloalkyl include, but are not limited to, cyclo-propyl, cyclobutyl, cyclopentyl and cyclohexyl.

The term "hydroxy", as employed herein as such or as part of another group, refers to an —OH group.

The term "cyano", as employed herein as such or as part of another group, refers to a —CN group.

The term "carboxy", as employed herein as such or as part of another group, refers to —COOH group.

The term "carbonyl", as employed herein as such or as part of another group, refers to a carbon atom double-bonded to an oxygen atom (C═O).

The term "oxo", as employed herein as such or as part of another group, refers to oxygen atom linked to another atom by a double bond (═O).

The term "$C_{1-7}$ alkoxy", as employed herein as such or as part of another group, refers to $C_{1-7}$ alkyl, as defined herein, appended to the parent molecular moiety through an oxygen atom. Representative examples of $C_{1-7}$ alkoxy include, but are not limited to methoxy, ethoxy, propoxy, butoxy, isobutoxy, sec-butoxy and tert-butoxy.

The term "hydroxy $C_{1-7}$ alkyl", as employed herein, refers to at least one hydroxy group, as defined herein, appended to the parent molecular moiety through a $C_{1-7}$ alkyl group, as defined herein. Representative examples of hydroxy $C_{1-7}$ alkyl include, but are not limited to, hydroxymethyl, 2,2-dihydroxyethyl, 1-hydroxyethyl, 3-hydroxypropyl, 1-hydroxypropyl, 1-methyl-1-hydroxyethyl and 1-methyl-1-hydroxypropyl.

The term "halogen $C_{1-7}$ alkyl", as employed herein, refers to at least one halogen, as defined herein, appended to the parent molecular moiety through a $C_{1-7}$ alkyl group, as defined herein. Representative examples of halo $C_{1-7}$ alkyl include, but are not limited to, fluoromethyl, difluoromethyl, trifluoromethyl, 2-chloroethyl and 3-bromopropyl.

The term "cyano $C_{1-7}$ alkyl", as employed herein, refers to a cyano group, as defined herein, appended to the parent molecular moiety through a $C_{1-7}$ alkyl group, as defined herein. Representative examples of cyano $C_{1-7}$ alkyl include, but are not limited to, cyanomethyl, 1-cyanoethyl, 1-cyanopropyl and 2-cyanopropyl.

The term "halogen $C_{1-7}$ alkoxy", as employed herein, refers to at least one halogen, as defined herein, appended to the parent molecular moiety through a $C_{1-7}$ alkoxy group, as defined herein.

The term "phenyl $C_{1-7}$ alkyl", as employed herein, refers to at least one phenyl group appended to the parent molecular moiety through a $C_{1-7}$ alkyl group, as defined herein.

The term "$C_{1-7}$ alkyl carbonyl", as employed herein as such or as part of another group, refers to a $C_{1-7}$ alkyl group, as defined herein, appended to the parent molecular moiety through a carbonyl group, as defined herein.

The term "$C_{1-7}$ alkoxy $C_{1-7}$ alkyl", as employed herein as such or as part of another group, refers to at least one $C_{1-7}$ alkoxy group, as defined herein, appended to the parent molecular moiety through an $C_{1-7}$ alkyl group, as defined herein.

The term "4-12 membered heterocyclyl" as employed herein, refers to a saturated, partially saturated or aromatic ring with 4-12 ring atoms, of which 1-4 atoms are heteroatoms selected from a group consisting of N, O and S. One embodiment of a "4-12 membered heterocyclyl" is a "4-10 membered heterocyclyl" which refers to a saturated, partially saturated or aromatic ring with 4-10 ring atoms, of which 1-4 atoms are heteroatoms selected from a group consisting of N, O and S. Representative examples of a 4-12 membered heterocyclic ring include, but are not limited to, oxetanyl, azetidinyl, pyrazolyl, 1,2,4-triazol-1-yl, 1,2,3-triazol-1-yl, pyrimidinyl, pyridinyl, piperidinyl, tetrazolyl, piperazinyl, furanyl, morpholinyl, piperidinyl, pyrrolidinyl, thiazolyl, isoxazolyl, pyrazinyl tetrahydropyranyl, 1,2,4-oxadiazolyl, oxazolyl, imidazolyl, indolyl and 4,5-dihydroimidazolyl rings.

The term "3-10 membered carbocyclyl", as employed herein, refers to a saturated, partially saturated or aromatic ring with 3 to 10 ring atoms consisting of carbon atoms only. One embodiment of a "3-10 membered carbocyclyl" is a "3-6 membered carbocyclyl" which refers to a saturated, partially saturated or aromatic ring with 3 to 6 ring atoms consisting of carbon atoms only. Representative examples of a 3-membered carbocyclyl group include, but are not limited to, phenyl, cyclohexyl, cyclohexenyl, cyclopentyl, cyclopentenyl and cyclobutyl rings.

The term "substituted" as used herein in connection with various residues refers to, if not otherwise defined, to halogen substituents, such as fluorine, chlorine, bromine, iodine, or $C_{1-7}$ alkyl, $C_{3-7}$ cycloalkyl, hydroxy, amino, nitro, cyano, thiol $C_{1-7}$ alkyl, methylsulfonyl, $C_{1-7}$ alkoxy, halo $C_{1-7}$ alkyl, hydroxy $C_{1-7}$ alkyl or amino $C_{1-7}$ alkyl substituents. Preferred are halogen, $C_{1-7}$ alkyl, hydroxy, amino, halo $C_{1-7}$ alkyl, $C_{1-7}$ alkoxy and methylsulfonyl substituents. In one group of preferred substituents are 1-2 substituents selected from $C_{1-7}$ alkyl or halogen substituents, particularly $C_{1-3}$ alkyl or halogen substituents, particularly methyl, ethyl, chloro, fluoro or bromo substituents.

The "substituted" groups may contain 1 to 3, preferably 1 or 2, of the above mentioned substituents, if not otherwise defined.

Optically active enantiomers or diastereomers of compounds of formula (I) can be prepared e.g. by resolution of the racemic end product by known methods or by using suitable optically active starting materials. Similarly, racemic compounds of formula (I) can be prepared by using racemic starting materials. Resolution of racemic compounds of formula (I) or a racemic starting material thereof can be carried out, for example, by converting the racemic compound into its diastereromeric salt mixture by reaction with an optically active acid and subsequent separation of the diastereomers by crystallization. Representative examples of said optically active acids include, but are not limited to, D-tartaric acid and dibenzoyl-D-tartaric acid. Alternatively, preparative chiral chromatography may be used for resolution of the racemic mixture.

Pharmaceutically acceptable salts are well known in the field of pharmaceuticals. Non-limiting examples of suitable salts include metal salts, ammonium salts, salts with an organic base, salts with an inorganic acid, salts with organic acid, and salts with basic or acidic amino acid. Non-limiting examples of metal salts include alkali metal salts such as sodium salt and potassium salt; alkaline earth metal salts such as calcium salt, and magnesium salt. Non-limiting examples of salts with inorganic or organic acids include chlorides, bromides, sulfates, nitrates, phosphates, sulfonates, methane sulfonates, formates, tartrates, maleates, citrates, benzoates, salicylates, ascorbates, acetates, oxalates, fumarates, hemifumarates, and succinates. Pharmaceutically acceptable esters, when applicable, may be prepared by known methods using pharmaceutically acceptable acids that are conventional in the field of pharmaceuticals and that retain the pharmacological properties of the free form. Non-limiting examples of these esters include esters of aliphatic or aromatic alcohols, e.g. methyl, ethyl, propyl, isopropyl, butyl, isobutyl, sec-butyl, tert-butyl esters. Phosphate esters and carbonate esters, are also within the scope of the invention.

The definition of formula (I) above is inclusive of all the possible isotopes and isomers, such as stereoisomers, of the compounds, including geometric isomers, for example Z and E isomers (cis and trans isomers), and optical isomers, e.g. diastereomers and enantiomers, and prodrug esters, e.g. phosphate esters and carbonate esters.

It will be appreciated by those skilled in the art that the present compounds may contain at least one chiral center. Accordingly, the compounds may exist in optically active or racemic forms. It is to be understood that the formula (I) includes any racemic or optically active form, or mixtures thereof. In one embodiment, the compounds are the pure (R)-isomers. In another embodiment, the compounds are the pure (S)-isomers. In another embodiment, the compounds are a mixture of the (R) and the (S) isomers. In another embodiment, the compounds are a racemic mixture comprising an equal amount of the (R) and the (S) isomers. The compounds may contain two chiral centers. In such case, according to one embodiment, the compounds are a mixture of diasteromers. According to another embodiment, the compounds of the invention are a mixture of enantiomers. According to still another embodiment, the compounds are pure enantiomers. The individual isomers may be obtained using the corresponding isomeric forms of the starting material or they may be separated after the preparation of the end compound according to conventional separation methods. For the separation of optical isomers, e.g. enantiomers or diastereomers, from the mixture thereof the conventional resolution methods, e.g. fractional crystallisation, may be used.

The present compounds may also exist as tautomers or equilibrium mixtures thereof wherein a proton of a compound shifts from one atom to another. Examples of tautomerism include, but are not limited to, amido-imido, keto-enol, phenol-keto, oxime-nitroso, nitro-aci, imine-enamine, annular tautomerism of heterocyclic rings such as pyrazole ring, and the like. Tautomeric forms are intended to be encompassed by compounds of formula (I), even though only one tautomeric form may be depicted.

Examples of preferred compounds of one group of formula (I) include (2,3-Dihydro-4H-benzo[b][1,4]oxazin-4-yl)(5-(3-(trifluoromethoxy)phenyl)-pyridin-3-yl)methanone (Compound 1);

(7-Fluoro-2,3-dihydro-4H-benzo[b][1,4]oxazin-4-yl)(5-(4-fluorophenyl)pyridin-3-yl)methanone (Compound 2);

(2,3-Dihydro-4H-benzo[b][1,4]oxazin-4-yl)(4-methyl-5-phenylpyridin-3-yl)-methanone (Compound 3);

(3,4-Dihydroquinolin-1(2H)-yl)(4-methyl-5-phenylpyridin-3-yl)methanone (Compound 4);

(2,3-Dihydro-4H-benzo[b][1,4]oxazin-4-yl)(5-(4-fluorophenyl)-4-methylpyridin-3-yl)methanone (Compound 5);

(4-Amino-5-phenylpyridin-3-yl)(3,4-dihydroquinolin-1(2H)-yl)methanone (Compound 6);

(2,3-Dihydro-4H-benzo[b][1,4]oxazin-4-yl)(5-(4-fluorophenyl)pyridazin-3-yl)-methanone (Compound 7);

(6-(Benzo[d]oxazol-6-yl)pyrazin-2-yl)(2,3-dihydro-4H-benzo[b][1,4]oxazin-4-yl)methanone (Compound 8);

(2,3-Dihydro-4H-benzo[b][1,4]oxazin-4-yl)(6-(3-(trifluoromethoxy)phenyl)-pyrazin-2-yl)methanone (Compound 9);

(2,3-Dihydro-4H-benzo[b][1,4]oxazin-4-yl)(5-phenylpyridin-3-yl)methanone (Compound 10);

(5-(4-Chlorophenyl)pyridin-3-yl)(2,3-dihydro-4H-benzo[b][1,4]oxazin-4-yl)-methanone (Compound 11);

(6-(2,3-Dihydrobenzofuran-6-yl)pyrazin-2-yl)(3,4-dihydroquinolin-1(2H)-yl)-methanone (Compound 12);

(2,3-Dihydro-4H-benzo[b][1,4]oxazin-4-yl)(6-(2,3-dihydrobenzofuran-6-yl)pyrazin-2-yl)methanone (Compound 13);

(3,4-Dihydroquinolin-1(2H)-yl)(6-(4-methoxyphenyl)pyrazin-2-yl)methanone (Compound 14);

(3,4-Dihydroquinolin-1(2H)-yl)(6-phenylpyrazin-2-yl)methanone (Compound 15);

(3,4-Dihydroquinolin-1(2H)-yl)(5-(4-fluorophenyl)pyridin-3-yl)methanone (Compound 16);

(5-(4-Chlorophenyl)pyridin-3-yl)(2,3-dihydro-4H-benzo[b][1,4]oxazin-4-yl)-methanone (Compound 17);

(3,4-Dihydroquinolin-1(2H)-yl)(5-(4-methoxyphenyl)pyridin-3-yl)methanone (Compound 18);

(5-(3,4-Difluorophenyl)pyridin-3-yl)(2,3-dihydro-4H-benzo[b][1,4]oxazin-4-yl)-methanone (Compound 19);

(2,3-Dihydro-4H-benzo[b][1,4]oxazin-4-yl)(6-(4-fluorophenyl)pyrazin-2-yl)-methanone (Compound 20);

(6-(4-Fluorophenyl)pyrazin-2-yl)(4-methyl-3,4-dihydroquinoxalin-1(2H)-yl)-methanone (Compound 21);

(6-(4-Fluorophenyl)pyrazin-2-yl)(2-methyl-3,4-dihydroquinolin-1(2H)-yl)-methanone (Compound 22);

(2,3-Dihydro-4H-benzo[b][1,4]oxazin-4-yl)(5-(4-methoxyphenyl)pyridin-3-yl)-methanone (Compound 23);

(2,3-Dihydro-4H-benzo[b][1,4]oxazin-4-yl)(5-(4-fluorophenyl)pyridin-3-yl)-methanone (Compound 24);
(3,4-Dihydroquinolin-1(2H)-yl)(6-(3-methoxyphenyl)pyrazin-2-yl)methanone (Compound 25);
(6-(4-Fluorophenyl)pyrazin-2-yl)(3-methyl-2,3-dihydro-4H-benzo[b][1,4]oxazin-4-yl)methanone (Compound 26);
(2,3-Dihydro-4H-benzo[b][1,4]oxazin-4-yl)(5-(4-fluoro-3-hydroxyphenyl)-pyridin-3-yl)methanone (Compound 27);
(5-(2,4-Difluorophenyl)pyridin-3-yl)(2,3-dihydro-4H-benzo[b][1,4]oxazin-4-yl)-methanone (Compound 28);
(6-(2,3-Dihydrobenzofuran-6-yl)pyrazin-2-yl)(octahydro-4H-benzo[b][1,4]-oxazin-4-yl)methanone (Compound 29);
(3,4-Dihydroquinolin-1(2H)-yl)(6-(4-fluorophenyl)pyridazin-4-yl)methanone (Compound 30);
(5-(4-Fluorophenyl)pyridin-3-yl)(4-methyl-3,4-dihydroquinoxalin-1(2H)-yl)-methanone (Compound 31);
(2,3-Dihydro-4H-benzo[b][1,4]oxazin-4-yl)(5-(4-nitrophenyl)pyridin-3-yl)-methanone (Compound 32);
(5-(Cyclohex-1-en-1-yl)pyridin-3-yl)(2,3-dihydro-4H-benzo[b][1,4]oxazin-4-yl)methanone (Compound 33);
(3,4-Dihydro-1,5-naphthyridin-1(2H)-yl)(5-(4-methoxyphenyl)pyridin-3-yl)-methanone (Compound 34);
Ethyl 4-(6-(4-fluorophenyl)pyrazine-2-carbonyl)-3,4-dihydro-2H-benzo[b][1,4]-oxazine-2-carboxylate (Compound 35);
1-(5-Phenylnicotinoyl)-2,3-dihydroquinolin-4(1H)-one (Compound 36);
(3,4-Dihydro-1,5-naphthyridin-1(2H)-yl)(6-phenylpyrazin-2-yl)methanone (Compound 37);
(3,4-Dihydroquinolin-1(2H)-yl)(5-(3-methoxyphenyl)pyridin-3-yl)methanone (Compound 38);
(5-(1H-Pyrrol-1-yl)pyridin-3-yl)(3,4-dihydroquinolin-1(2H)-yl)methanone (Compound 39);
(2,3-Dihydro-4H-benzo[b][1,4]oxazin-4-yl)(6-(4-fluorophenyl)pyridazin-4-yl)-methanone (Compound 40);
(2,3-Dihydro-4H-benzo[b][1,4]oxazin-4-yl)(5-(2-fluorophenyl)pyridin-3-yl)-methanone (Compound 41);
(3,4-Dihydro-1,5-naphthyridin-1(2H)-yl)(5-(4-fluorophenyl)pyridin-3-yl)-methanone (Compound 42);
(2,3-Dihydro-4H-benzo[b][1,4]oxazin-4-yl)(6-(1-methyl-1H-pyrazol-4-yl)-pyrazin-2-yl)methanone (Compound 43);
(2,3-Dihydro-4H-benzo[b][1,4]oxazin-4-yl)(5-(4-(trifluoromethyl)phenyl)pyridin-3-yl)methanone (Compound 44);
(2,3-Dihydro-4H-benzo[b][1,4]oxazin-4-yl)(5-(4-fluoro-2-methoxyphenyl)-pyridin-3-yl)methanone (Compound 45);
4-((5-(4-Fluorophenyl)pyridin-3-yl)sulfonyl)-3,4-dihydro-2H-benzo[b][1,4]-oxazine (Compound 46);
1-((5-(4-Fluorophenyl)pyridin-3-yl)sulfonyl)-1,2,3,4-tetrahydroquinoline (Compound 47);
(2,3-Dihydro-4H-benzo[b][1,4]oxazin-4-yl)(5-(3-(trifluoromethyl)phenyl)pyridin-3-yl)methanone (Compound 48);
(2,3-Dihydro-4H-benzo[b][1,4]oxazin-4-yl)(6'-fluoro-[3,3'-bipyridin]-5-yl)-methanone (Compound 49);
(2,3-Dihydro-4H-benzo[b][1,4]oxazin-4-yl)(5-(3-methoxyphenyl)pyridin-3-yl)-methanone (Compound 50);
(3,4-Dihydroquinolin-1(2H)-yl)(5-(1-phenylvinyl)pyridin-3-yl)methanone (Compound 51);
(3,4-Dihydroquinolin-1(2H)-yl)(6-phenylpyridazin-4-yl)methanone (Compound 52);
(6-Methoxy-3,4-dihydroquinolin-1(2H)-yl)(5-phenylpyridin-3-yl)methanone (Compound 53);
(3,4-Dihydroquinolin-1(2H)-yl)(5-(4-(hydroxymethyl)phenyl)pyridin-3-yl)-methanone (Compound 54);
(5-(4-Fluorophenyl)pyridin-3-yl)(octahydro-4H-benzo[b][1,4]oxazin-4-yl)-methanone (Compound 55);
(5-(4-Fluorophenyl)pyridin-3-yl)((4aS,8aS)-octahydro-4H-benzo[b][1,4]oxazin-4-yl)methanone (Compound 56);
(5-(4-Fluorophenyl)pyridin-3-yl)((4aR,8aR)-octahydro-4H-benzo[b][1,4]oxazin-4-yl)methanone (Compound 57);
(2,3-Dihydro-4H-benzo[b][1,4]oxazin-4-yl)(5-(4-fluoro-3-nitrophenyl)pyridin-3-yl)methanone (Compound 58);
(5-Methoxy-3,4-dihydroquinolin-1(2H)-yl)(5-phenylpyridin-3-yl)methanone (Compound 59);
(5-(4-Fluorophenyl)pyridin-3-yl)(indolin-1-yl)methanone (Compound 60);
(3,4-Dihydro-1,5-naphthyridin-1(2H)-yl)(5-phenylpyridin-3-yl)methanone (Compound 61);
[3,4'-Bipyridin]-5-yl(3,4-dihydroquinolin-1(2H)-yl)methanone (Compound 62);
(2,3-Dihydro-4H-benzo[b][1,4]oxazin-4-yl)(6-(1-methyl-1H-pyrazol-5-yl)-pyrazin-2-yl)methanone (Compound 63);
(6-(4-Fluorophenyl)pyridazin-4-yl)(2-methyl-3,4-dihydroquinolin-1(2H)-yl)-methanone (Compound 64);
(2,3-Dihydro-4H-benzo[b][1,4]oxazin-4-yl)(5-(4-(hydroxymethyl)phenyl)pyridin-3-yl)methanone (Compound 65);
(5-(3,6-Dihydro-2H-pyran-4-yl)pyridin-3-yl)(2,3-dihydro-4H-benzo[b][1,4]-oxazin-4-yl)methanone (Compound 66);
Methyl 1-(5-phenylnicotinoyl)-1,2,3,4-tetrahydroquinoline-6-carboxylate (Compound 67);
(3,4-Dihydroquinolin-1(2H)-yl)(5-(4-((dimethylamino)methyl)phenyl)pyridin-3-yl)methanone (Compound 68);
(7-Methoxy-3,4-dihydroquinolin-1(2H)-yl)(5-phenylpyridin-3-yl)methanone (Compound 69);
[3,3'-Bipyridin]-5-yl(3,4-dihydroquinolin-1(2H)-yl)methanone (Compound 70);
(2,3-Dihydro-4H-benzo[b][1,4]oxazin-4-yl)(5-(p-tolyl)pyridin-3-yl)methanone (Compound 71);
(5-(2,3-Dihydrobenzofuran-6-yl)pyridin-3-yl)(octahydro-4H-benzo[b][1,4]-oxazin-4-yl)methanone (Compound 72);
(2,3-Dihydro-4H-benzo[b][1,4]oxazin-4-yl)(5-(1-methyl-1H-pyrazol-4-yl)-pyridin-3-yl)methanone (Compound 73);
(2,3-Dihydro-4H-benzo[b][1,4]oxazin-4-yl)(5-(pyrrolidin-1-yl)pyridin-3-yl)-methanone (Compound 74);
2,3-Dihydro-4H-benzo[b][1,4]oxazin-4-yl)(5-(6,6-dimethyl-3-azabicyclo[3.1.0]-hexan-3-yl)pyridin-3-yl)methanone (Compound 75);
(2,3-Dihydro-4H-benzo[b][1,4]oxazin-4-yl)(6-(pyrrolidin-1-yl)pyrazin-2-yl)-methanone (Compound 76);
(6-(3,3-Difluoroazetidin-1-yl)pyrazin-2-yl)(2,3-dihydro-4H-benzo[b][1,4]oxazin-4-yl)methanone (Compound 77);
(2,3-Dihydro-4H-benzo[b][1,4]oxazin-4-yl)(6-(4-methylpiperazin-1-yl)pyrazin-2-yl)methanone (Compound 78);
1-(3,4-Dihydroquinolin-1(2H)-yl)-2-(5-(4-fluorophenyl)pyridin-3-yl)ethan-1-one (Compound 79);
1-(2,3-Dihydro-4H-benzo[b][1,4]oxazin-4-yl)-2-(5-(4-methoxyphenyl)pyridin-3-yl)ethan-1-one (Compound 80);
4-((5-Phenylpyridin-3-yl)methyl)-3,4-dihydro-2H-benzo[b][1,4]oxazine (Compound 81);

(3,4-Dihydroquinolin-1(2H)-yl)(5-(4-methyl-1H-imidazol-1-yl)pyridin-3-yl)-methanone (Compound 82);

(3,4-Dihydroquinolin-1(2H)-yl)(6-(4-methyl-1H-imidazol-1-yl)pyrazin-2-yl)-methanone (Compound 83);

(3,4-Dihydroquinolin-1(2H)-yl)(6-(4-methyl-1H-pyrazol-1-yl)pyrazin-2-yl)-methanone (Compound 84);

(6-Benzylpyrazin-2-yl)(3,4-dihydroquinolin-1(2H)-yl) methanone (Compound 85);

1-(2,3-Dihydro-4H-benzo[b][1,4]oxazin-4-yl)-2-(5-(4-fluorophenyl)pyridin-3-yl)ethan-1-one (Compound 86);

(3,4-Dihydroquinolin-1(2H)-yl)(6-(3,5-dimethyl-1H-pyrazol-1-yl)pyrazin-2-yl)-methanone (Compound 87);

(3,4-Dihydroquinolin-1(2H)-yl)(5-(4-methyl-1H-pyrazol-1-yl)pyridin-3-yl)-methanone (Compound 88);

1-((5-(4-Fluorophenyl)pyridin-3-yl)methyl)-1,2,3,4-tetrahydroquinoline (Compound 89); or 1-((5-(4-Fluorophenyl)pyridin-3-yl)methyl)indoline (Compound 90);

and tautomers and pharmaceutically acceptable salts thereof.

Compounds of the invention may be administered to a patient in therapeutically effective amounts which range usually from about 0.5 to about 2000 mg, more typically form about 1 to about 500 mg, for example from about 2 to about 100 mg, daily depending on the age, sex, weight, ethnic group, condition of the patient, condition to be treated, administration route and the active ingredient used. The compounds of the invention can be formulated into dosage forms using the principles known in the art. The compound can be given to a patient as such or in combination with suitable pharmaceutical excipients in the form of tablets, granules, capsules, suppositories, emulsions, suspensions or solutions. Choosing suitable ingredients for the composition is a routine for those of ordinary skill in the art. Suitable carriers, solvents, gel-forming ingredients, dispersion forming ingredients, antioxidants, colours, sweeteners, wetting compounds and other ingredients normally used in this field of technology may also be used. The compositions containing the active compound can be given enterally or parenterally, the oral route being the preferred way. The contents of the active compound in the composition is from about 0.5 to 100%, typically from about 0.5 to about 20%, per weight of the total composition.

The compounds of the invention can be given to the subject as the sole active ingredient or in combination with one of more other active ingredients for treatment of a particular disease.

In the treatment of a steroid receptor dependent disease or condition, such as endocrine cancers and disorders including prostate cancer and breast cancer, a combination of therapeutic agents and/or other treatments (e.g., radiation therapy) is often advantageous. The second (or third) agent to be administered may have the same or different mechanism of action than the primary therapeutic agent.

Accordingly, a compound of the invention may be administered in combination with other anti-cancer treatments useful in the treatment of cancers such as prostate cancer or breast cancer. For example, a compound of the invention can be packaged together with instructions that the compound is to be used in combination with other anti-cancer agents and treatments for the treatment of cancer. The present invention further comprises combinations of a compound of the invention and one or more additional agents in kit form, for example, where they are packaged together or placed in separate packages to be sold together as a kit, or where they are packaged to be formulated together.

According to one embodiment of the invention, the therapeutically effective amount of a compound of formula (I) or a pharmaceutically acceptable salt thereof is co-administered with a glucocorticoid and/or a mineralocorticoid and, optionally, with one or more anti-cancer agents.

Examples of suitable glucocorticoids include, but are not limited to, hydrocortisone, prednisone, prednisolone, methylprednisolone and dexamethasone. Examples of suitable mineralocorticoids include, but are not limited to, fludrocortisone, deoxycorticosterone, 11-desoxycortisone and deoxycorticosterone acetate.

The optional other anti-cancer agents which can be administered in addition to a compound of formula (I) or a pharmaceutically acceptable salt thereof include, but are not limited to, non-steroidal androgen receptor antagonists (e.g. enzalutamide, apalutamide and darolutamide);

steroidogenesis inhibitors (e.g. CYP17A1 inhibitors such as abiraterone acetate and seviteronel);

chemotherapeutic agents (e.g. docetaxel and paclitaxel);

antiestrogens (e.g. tamoxifen and fulvestrant);

epigenetic modulators (e.g. BET inhibitors and HDAC inhibitors);

mTOR inhibitors (e.g. everolimus);

AKT inhibitors (e.g. AZ5363);

radiopharmaceuticals (e.g. alpharadin);

GnRH/LHRH analogues (such as leuprorelin);

PI3K inhibitors (e.g. idelalisib); and

CDK4/6 inhibitors (e.g. ribocyclib).

According to one embodiment of the invention, the therapeutically effective amount of a compound of formula (I) or a pharmaceutically acceptable salt thereof is administered to a subject in need thereof in addition to a therapeutically effective amount of one or more anti-cancer agents selected from the list consisting of non-steroidal androgen receptor antagonists (e.g. enzalutamide, apalutamide and darolutamide);

steroidogenesis inhibitors (e.g. CYP17A1 inhibitors such as abiraterone acetate and seviteronel);

chemotherapeutic agents (e.g. docetaxel and paclitaxel);

antiestrogens (e.g. tamoxifen and fulvestrant);

epigenetic modulators (e.g. BET inhibitors and HDAC inhibitors);

mTOR inhibitors (e.g. everolimus);

AKT inhibitors (e.g. AZ5363);

radiopharmaceuticals (e.g. alpharadin);

GnRH/LHRH analogues (such as leuprorelin);

PI3K inhibitors (e.g. idelalisib); and

CDK4/6 inhibitors (e.g. ribocyclib).

According to one embodiment of the invention, the therapeutically effective amount of a compound of formula (I) or a pharmaceutically acceptable salt thereof is administered to a subject in need thereof in addition to a therapeutically effective amount of a steroidogenesis inhibitor (e.g. a CYP17A1 inhibitor). Examples of suitable CYP17A1 inhibitors include, but are not limited to, abiraterone acetate and seviteronel.

According to another embodiment of the invention, the therapeutically effective amount of a compound of formula (I) or a pharmaceutically acceptable salt thereof is administered to a subject in need thereof in addition to a therapeutically effective amount of a non-steroidal androgen receptor antagonist. Examples of suitable non-steroidal androgen receptor (AR) antagonists include, but are not limited to, enzalutamide, apalutamide and darolutamide.

According to still another embodiment, the present invention provides a pharmaceutical combination comprising a compound of formula (I) or a pharmaceutically acceptable salt thereof and at least one additional active ingredient selected from the list consisting of

- a glucocorticoid,
- a mineralocorticoid,
- a steroidogenesis inhibitor (e.g. a CYP17A1 inhibitor),
- a non-steroidal androgen receptor antagonist,
- chemotherapeutic agents (e.g. docetaxel and paclitaxel),
- antiestrogens (e.g. tamoxifen and fulvestrant),
- epigenetic modulators (e.g. BET inhibitors and HDAC inhibitors),
- mTOR inhibitors (e.g. everolimus);
- AKT inhibitors (e.g. AZ5363);
- radiopharmaceuticals (e.g. alpharadin);
- GnRH/LHRH analogues (such as leuprorelin);
- PI3K inhibitors (e.g. idelalisib); and
- CDK4/6 inhibitors (e.g. ribocyclib)

for simultaneous, separate or sequential administration.

The above other therapeutic agents, when employed in combination with a compound of the invention can be used, for example, in those amounts indicated in the Physicians' Desk Reference (PDR) or as otherwise determined by one of ordinary skill in the art.

The compounds of the invention can be prepared by a variety of synthetic routes analogously to the methods known in the literature using suitable starting materials. The present invention will be explained in more detail by the following experiments and examples. The experiments and examples are meant only for illustrating purposes and do not limit the scope of the invention defined in claims.

EXAMPLES

Intermediate 1: 6-(2,3-Dihydrobenzofuran-5-yl) pyrazine-2-carboxylic acid

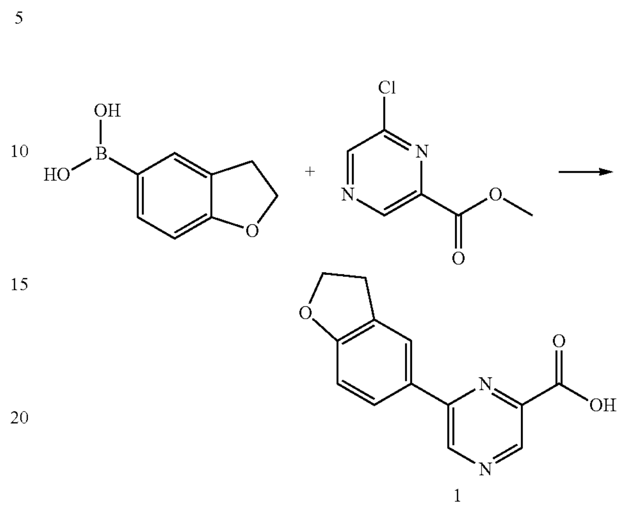

1

A mixture of methyl-6-chloro-2-pyrazinecarboxylate (0.5 g, 2.90 mmol), 2,3-dihydrobenzofuran-5-boronic acid (0.47 g, 2.90 mmol), $PdCl_2(PPh_3)_2$ (102.0 mg, 0.145 mmol) and sodium carbonate (0.30 g, 2.90 mmol) in acetonitrile/ethanol/water (2 ml/2 ml/2 ml) was degassed and heated at 100° C. in microwave oven for 1.5 h. After cooling to RT, the reaction mixture was diluted with EtOAc (10 ml) and filtered. The combined organic layer was washed with brine, dried with anhydrous $Na_2SO_4$ and concentrated in vacuo. The crude residue was purified by column chromatography to afford the title compound. LC-MS: m/z 243.1 $[M+H]^+$ The following intermediates were prepared according to the procedure described for Intermediate 1 from the starting materials indicated on the table.

| No. | Structure | LC-MS | Starting material |
|---|---|---|---|
| Int-2 | 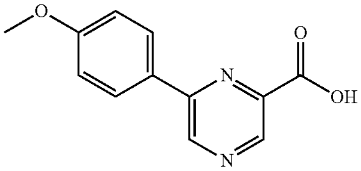 [SMILES: COc1ccc(-c2cncc(C(=O)O)n2)cc1] | m/z 231.0 $[M+H]^+$ | 4-Methoxyphenylboronic acid and Methyl-6-chloro-2-pyrazine-carboxylate |
| Int-3 | 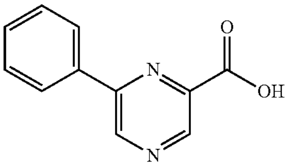 [SMILES: O=C(O)c1cncc(-c2ccccc2)n1] | m/z 201.1 $[M+H]^+$ | Methyl 6-phenylpyrazine-2-carboxylate |
| Int-4 | 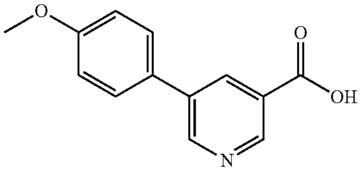 [SMILES: COc1ccc(-c2cncc(C(=O)O)c2)cc1] | m/z 229.1 $[M+H]^+$ | 4-Methoxyphenylboronic acid and 5-Bromopyridine-3-carboxylic acid |

-continued

| No. | Structure | LC-MS | Starting material |
|---|---|---|---|
| Int-5 | 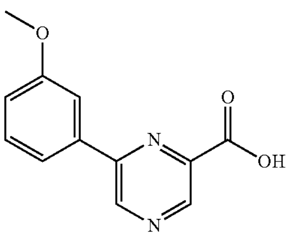 [SMILES: COc1cccc(-c2cncc(C(=O)O)n2)c1] | m/z 231.0 [M + H]$^+$ | 3-Methoxyphenylboronic acid and Methyl-6-chloro-2-pyrazine-carboxylate |
| Int-6 | 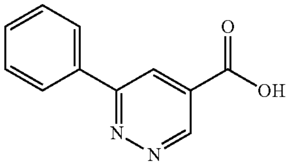 [SMILES: O=C(O)c1cnnc(-c2ccccc2)c1] | m/z 201.1 [M + H]$^+$ | 3-Chloropyridazine-5-carboxylic acid and (4,4,5,5-Tetramethyl-1,3,2-dioxa-borolan-2-yl)benzene |
| Int-7 | 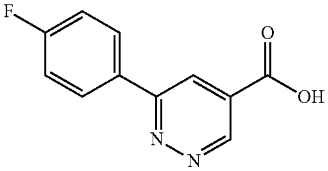 [SMILES: O=C(O)c1cnnc(-c2ccc(F)cc2)c1] | m/z 219.0 [M + H]$^+$ | 3-Chloropyridazine-5-carboxylic acid and 4-Fluorobenzeneboronc acid |
| Int-8 | 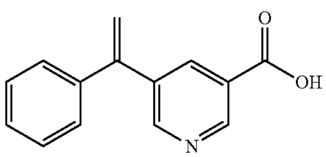 [SMILES: C=C(c1ccccc1)c1cncc(C(=O)O)c1] | m/z 226.4 [M + H]$^+$ | 1-Phenylvinylboronic acid pinacol ester and 5-Bromopyridine-3-carboxylic acid |
| Int-9 | 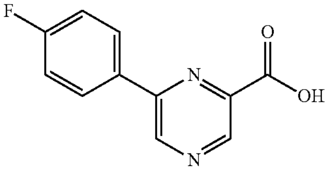 [SMILES: O=C(O)c1cncc(-c2ccc(F)cc2)n1] | m/z 219.0 [M + H]$^+$ | 6-Chloropyrazine-2-carboxylic acid and 4-Fluorobenzeneboronic acid |
| Int-10 | 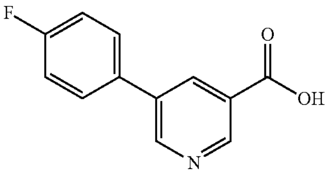 [SMILES: O=C(O)c1cncc(-c2ccc(F)cc2)c1] | m/z 218.0 [M + H]$^+$ | 5-Bromopyridine-3-carboxylic acid and 4-Fluorobenzeneboronic acid |

Intermediate 11: (5-Bromopyridin-3-yl)(3,4-dihydroquinolin-1(2H)-yl)methanone

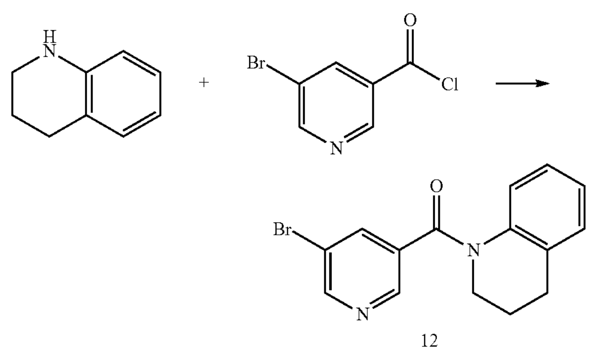

12

To a mixture of 5-bromopyridine-3-carbonylchloride (1.0 g, 4.54 mmol) and 1,2,3,4-tetrahydroquinoline (0.60 g, 4.54 mmol) in DCM (5 ml) at 0° C. was added TEA (1.80 ml, 13.61 mmol). The reaction mixture was stirred at RT for 5 h. Water (10 ml) was added and the product was extracted with DCM, washed with brine, dried with anhydrous $Na_2SO_4$ and concentrated in vacuo. The crude residue was purified by column chromatography to afford the title compound. LC-MS: m/z 317.4 [M+H]$^+$ The following intermediates were prepared according to the procedure described for Intermediate 12 from the starting materials indicated on the table.

| No. | Structure | LC-MS | Starting material |
|---|---|---|---|
| Int-12 | 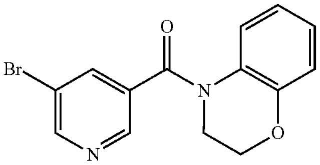 | m/z 321.0 [M + H]+ | 2,3-Dihydro-1,4-benzoxazine and 5-Bromopyridine-3-carbonylchloride |
| Int-13 | 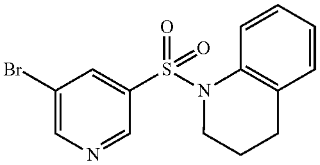 [SMILES: O=S(=O)(c1cncc(Br)c1)N1CCCc2ccccc21] | m/z 354.6 [M + H]+ | 5-Bromo-3-(chlorosulphonyl)pyridine and 1,2,3,4-Tetrahydroquinoline |
| Int-14 | 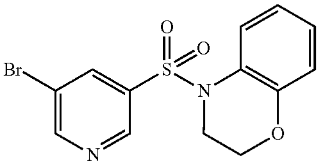 [SMILES: O=S(=O)(c1cncc(Br)c1)N1CCOc2ccccc21] | m/z 356.9 [M + H]+ | 5-Bromo-3-(chlorosulphonyl)pyridine and 2,3-Dihydro-1,4-benzoxazine |
| Int-15 | 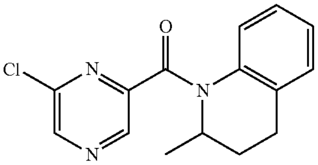 [SMILES: CC1CCc2ccccc2N1C(=O)c1cncc(Cl)n1] | m/z 288.0 [M + H]+ | 6-Chloropyrazine-2-carbonylchloride and 2-Methyl-1,2,3,4-tetrahydroquinoline |
| Int-16 | 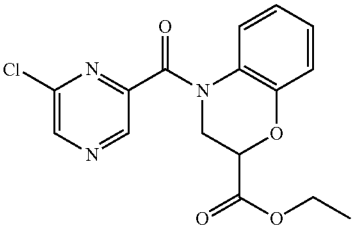 [SMILES: CCOC(=O)C1CN(C(=O)c2cncc(Cl)n2)c2ccccc2O1] | m/z 348.0 [M + H]+ | 6-Chloropyrazine-2-carbonylchloride and Ethylbenzomorpholine-2-carboxylate |
| Int-17 | 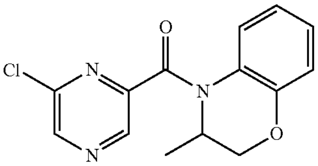 [SMILES: CC1COc2ccccc2N1C(=O)c1cncc(Cl)n1] | m/z 290.0 [M + H]+ | 6-Chloropyrazine-2-carbonyl chloride and 3-Methyl-3,4-dihydro-2H-benzo[b][1,4]oxazine |

Intermediate 18: (6-Chloropyrazin-2-yl)(2,3-dihydro-4H-benzo[b][1,4]oxazin-4-yl)methanone

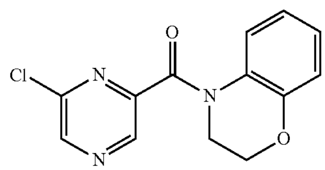 [SMILES: O=C(c1cncc(Cl)n1)N1CCOc2ccccc21]

To a mixture of 6-chloropyrazine-2-carboxylic acid (0.793 g, 5.0 mmol) in dry DCM (10 ml) was added few drops of DMF and oxalyl chloride (0.858 ml, 10.0 mmol). The mixture was stirred at RT for 2 h. Solvents were evaporated and fresh DCM (10 ml) was added. Mixture was cooled to 0-5° C. (ice cooling) and DIPEA (1.742 ml, 10.0 mmol) and 3,4-dihydro-2H-benzo[b][1,4]oxazine (0.676 g, 5.0 mmol) were added. The mixture was stirred at RT overnight. The mixture was diluted with DCM, washed with water and brine, dried and evaporated. Crude product was purified by flash chromatography to afford 0.92 g of the title compound. $^1$H NMR (400 MHz, $d_6$-DMSO): δ 8.95 (s, 2H), 7.5-8.5 (br, 1H), 7.00-7.17 (m, 1H), 6.94 (dd, 1H), 6.65-6.95 (br, 1H), 4.14-4.52 (m, 2H), 3.74-4.08 (m, 2H).

Intermediate 19: 2-(5-Bromopyridin-3-yl)-1-(3,4-dihydroquinolin-1(2H)-yl)-ethan-1-one

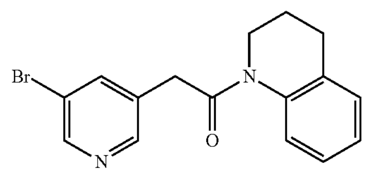 [SMILES: O=C(Cc1cncc(Br)c1)N1CCCc2ccccc21]

To an ice-cooled mixture of 5-bromo-3-pyridinecarboxylic acid (0.216 g, 1.00 mmol), 1,2,3,4-tetrahydroquinoline (0.147 g, 1.10 mmol) and trimethylamine (0.558 ml, 4.00 mmol) in dry DMF (5.5 ml) was added 1-propanephosphonic acid cyclic anhydride (50% in EtOAc, 0.795 ml, 1.35 mmol). The mixture was stirred overnight at RT. The mixture was diluted with EtOAc and water and phases were separated. Organic phase was washed with water and brine, dried and evaporated. Crude product was purified by flash chromatography to afford 0.27 g of the title compound. $^1$H NMR (400 MHz, $CDCl_3$): δ 8.53 (d, 1H), 8.23 (br s, 1H), 7.74 (br s, 1H), 6.98-7.26 (m, 4H), 3.83 (s, 2H), 3.81 (t, 2H), 2.52-2.70 (m, 2H), 1.94 (quint, 2H).

Intermediate 20: 2-(5-Bromopyridin-3-yl)-1-(2,3-dihydro-4H-benzo[b][1,4]-oxazin-4-yl)ethan-1-one

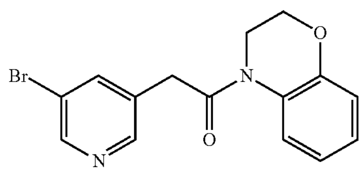 [SMILES: O=C(Cc1cncc(Br)c1)N1CCOc2ccccc21]

The compound was prepared according to the procedure described for Intermediate 19 starting from 5-bromo-3-pyridinecarboxylic acid and 3,4-dihydro-2H-benzo[b][1,4]oxazine. Yield: 0.24 g. $^1$H NMR (400 MHz, $CDCl_3$): δ 8.58 (d, 1H), 8.35 (br s, 1H), 7.78-7.85 (m, 1H), 6.99-7.22 (m, 2H), 6.89-6.98 (m, 2H), 4.24-4.32 (m, 2H), 3.83-4.05 (m, 4H).

Intermediate 21: 4-((5-Bromopyridin-3-yl)methyl)-3,4-dihydro-2H-benzo[b]-[1,4]oxazine

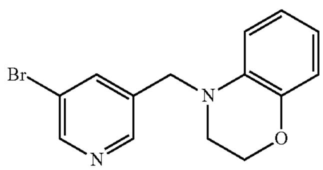 [SMILES: Brc1cncc(CN2CCOc3ccccc32)c1]

A mixture of 3,4-dihydro-2H-benzo[b][1,4]oxazine (0.170 g, 1.259 mmol), 3-bromo-5-(chloromethyl)pyridine (0.260 g, 1.259 mmol), cesium carbonate (0.821 g, 2.52 mmol) and potassium iodide (0.021 g, 0.126 mmol) in dry acetonitrile (5.0 ml) was stirred at 90° C. until the reaction was completed. Cooled mixture was diluted with EtOAc and filtered through a short plug of Celite. Filtrate was evaporated and crude product was purified by flash chromatography to afford 0.12 g of the title compound. $^1$H NMR (400 MHz, $d_6$-DMSO): δ 8.61 (d, 1H), 8.54 (d, 1H), 7.95-8.00 (m, 1H), 6.63-6.75 (m, 3H), 6.52-6.59 (m, 1H), 4.53 (s, 2H), 4.20-4.27 (m, 2H), 3.38-3.45 (m, 2H).

Intermediate 22: Ethyl 5-(4-methyl-1H-imidazol-1-yl)nicotinate

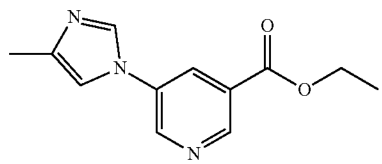 [SMILES: CCOC(=O)c1cncc(-n2cnc(C)c2)c1]

A mixture of tris(dibenzylideneacetone)dipalladium (7.33 mg, 0.008 mmol) and 2-di-tert-butylphosphino-3,4,5,6-tetramethyl-2',4',6'-triisopropyl-1,1'-biphenyl (8.65 mg, 0.018 mmol) in degassed toluene-dioxane (5:1, 1.0 ml) under nitrogen atmosphere was stirred at 120° C. for 10 min. Ethyl 5-bromonicotinate (0.23 g, 1.00 mmol), 4-methylimidazole (0.099 g, 1.20 mmol) and potassium phosphate (0.425 g, 2.00 mmol) were added and the mixture was stirred at 120° C. until reaction was completed. Cooled mixture was diluted with EtOAc and filtered through a short plug of Celite. Filtrate was dried and evaporated. Crude product was purified by flash chromatography to afford the pure compound. $^1$H NMR (400 MHz, $CDCl_3$): δ 9.18 (dd, 1H), 8.88 (dd, 1H), 8.28 (dd, 1H), 7.85 (d, 1H), 7.07-7.10 (m, 1H), 4.47 (q, 2H), 2.33 (d, 3H), 1.45 (t, 3H).

The following intermediates were prepared according to the procedure described for Intermediate 22 from the starting materials indicated on the table.

| No. | Structure | $^1$H NMR | Starting material |
|---|---|---|---|
| Int-23 | 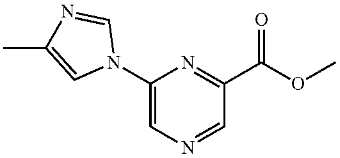 | $^1$H NMR (400 MHz, $d_6$ DMSO): δ 9.39 (d, 1H), 9.10 (d, 1H), 8.56 (d, 1H), 7.74-7.76 (m, 1H), 3.96 (s, 3H), 2.20 (d, 3H) | Methyl 6-chloro-pyrazine-2-carboxylate and 4-Methylimidazole |
| Int-24 | 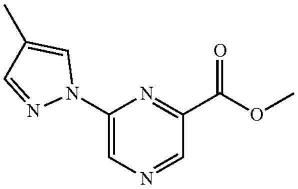 [SMILES: COC(=O)c1cncc(-n2cc(C)cn2)n1] | $^1$H NMR (400 MHz, $CDCl_3$): δ 9.47 (d, 1H), 9.11 (d, 1H), 8.38-8.40 (m, 1H), 7.63-7.64 (m, 1H), 4.05 (s, 1H), 2.16-2.19 (m, 3H) | Methyl 6-chloro-pyrazine-2-carboxylate and 4-Methylpyrazole |

Intermediate 25: Methyl 6-benzylpyrazine-2-carboxylate

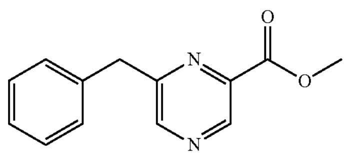 [SMILES: COC(=O)c1cncc(Cc2ccccc2)n1]

To a mixture of methyl 6-chloropyrazine-2-carboxylate (0.173 g, 1.00 mmol), potassium phosphate (0.637 g, 3.00 mmol), dicyclohexylphosphino-2,6-dimethoxy-biphenyl (0.041 g, 0.10 mmol) and palladium acetate (0.011 g, 0.05 mmol) in degassed THF (10 ml) under nitrogen atmosphere was added B-benzyl-9-borabicyclo[3.3.1]-nonane (0.5 M in THF, 2.5 ml, 5.0 mmol). The mixture was stirred at 65° C. until reaction was completed. Cooled mixture was diluted with DCM and filtered through a short plug of Celite. Filtrate was washed with aqueous 5% $Na_2CO_3$ solution, water and brine, dried and evaporated. Crude product was purified by flash chromatography to afford 0.16 g of the title compound. $^1$H NMR (400 MHz, $CDCl_3$): δ 9.14 (d, 1H), 8.57 (d, 1H), 7.23-7.37 (m, 5H), 4.31 (s, 2H), 4.05 (s, 3H).

Example 1

(2,3-Dihydro-4H-benzo[b][1,4]oxazin-4-yl)(5-(3-(trifluoromethoxy)phenyl)-pyridin-3-yl)methanone (Compound 1)

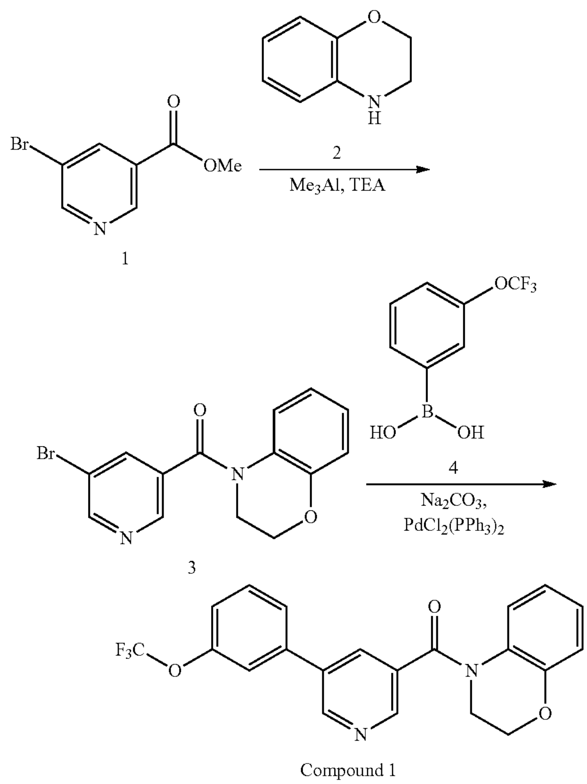

1

3

Compound 1 a) (5-Bromopyridin-3-yl)(2,3-dihydro-4H-benzo[b][1,4]oxazin-4-yl)methanone (3)

Methyl 5-bromonicotinate (8.0 g, 37.0 mmol) was treated with 4-dihydro-2H-benzo[b][1,4]oxazine (7.5 g, 56.0 mmol) in the presence of triethylamine (11.0 g, 15 mL, 0.11 mol), trimethylaluminum (28.0 ml, 2 M in toluene, 56.0 mmol) in 40 ml of toluene at 25° C. for 16 h. Purification by combi-flash chromatography afforded 9.5 g of the title compound. $^1$H-NMR (400 MHz, DMSO-$d_6$) δ: 8.80 (d, 1H), 8.68 (d, 1H), 8.20-8.26 (m, 1H), 7.20-7.45 (m, 1H), 7.04 (t, 1H), 6.92 (d, 1H), 6.70-6.80 (m, 1H), 4.31-4.40 (m, 2H), 3.82-3.90 (m, 2H). MS (ESI) m/z $[M+1]^+$: 318.99.

b) (2,3-Dihydro-4H-benzo[b][1,4]oxazin-4-yl)(5-(3-(trifluoromethoxy)phenyl)-pyridin-3-yl)methanone (Compound 1)

To a solution of methyl (5-bromopyridin-3-yl)(2,3-dihydro-4H-benzo[b][1,4]-oxazin-4-yl)methanone (200 mg, 0.627 mmol) in mixture of 2.5 ml of ethanol, 10 ml of toluene and 2.5 ml of water were added 3-(trifluoromethoxy)phenyl)boronic acid (142 mg, 0.689 mmol) and sodium carbonate (133 mg, 1.25 mmol) under inert atmosphere. Reaction mixture was degassed for 10 min followed by addition of bis(triphenyl-phosphine)palladium(II) dichloride. Degassing was continued for another 10 minutes. Resulting reaction mixture was stirred at 100° C. for 16 h. After completion of the reaction as indicated by TLC, the mixture was filtered through celite bed. Obtained filtrate was diluted with water (10 ml) and EtOAc (21 ml), and extracted with EtOAc (3×10 ml). The combined organic layer was washed with water and brine, dried over anhydrous sodium sulphate and concentrated under reduced pressure. The residue was purified by combi-flash chromatography using 5-40% EtOAc in heptane as an eluent to afford 0.08 g of the title compound. $^1$H NMR (400 MHz, DMSO-$d_6$) δ: 9.05 (d, 1H), 8.73 (s, 1H), 8.28 (s, 1H), 7.81 (d, 1H), 7.76 (s, 1H), 7.65 (t, 1H), 7.45 (dd, 1H), 7.10-7.30 (m, 1H), 7.03 (dt, 1H), 6.94 (dd, 1H), 6.70-6.80 (m, 1H), 4.32-4.40 (m, 2H), 3.86-3.95 (m, 2H). MS (ESI) m/z $[M+1]^+$: 401.13.

Example 2

(7-Fluoro-2,3-dihydro-4H-benzo[b][1,4]oxazin-4-yl)(5-(4-fluorophenyl)pyridin-3-yl)methanone (Compound 2)

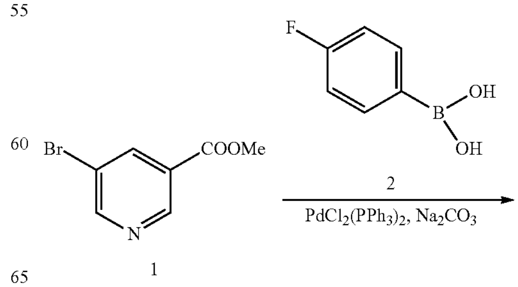

1

-continued

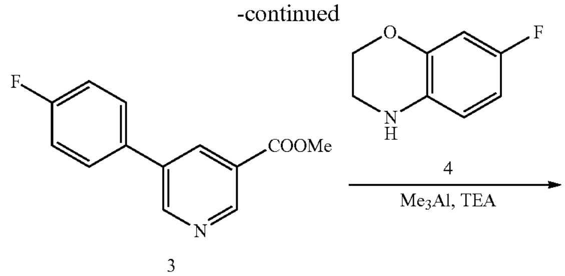

3

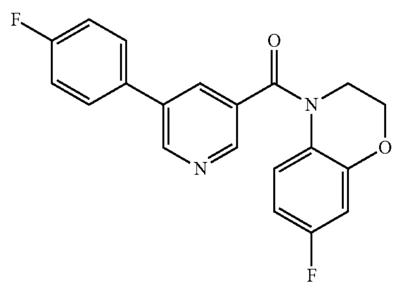

Compound 2 a) Methyl 5-(4-fluorophenyl)nicotinate (3)

Methyl 5-bromonicotinate (2.0 g, 9.3 mmol) was treated with (4-fluorophenyl)-boronic acid (1.4 g, 10.0 mmol) in the presence of sodium carbonate (2.0 g, 19.0 mmol) and bis(triphenylphosphine)palladium(II) dichloride (0.65 g, 0.93 mmol) in 40 ml of DME and 20 ml water at 90° C. for 4 h. Purification by combi-flash using 5-30% EtOAc in heptane as an eluent afforded 1.7 g of the title compound. $^1$H-NMR (400 MHz, DMSO-$d_6$): δ: 9.13 (s, 1H), 9.07 (s, 1H), 8.47 (d, 1H), 7.87 (t, 2H), 7.37 (t, 2H), 3.93 (s, 3H). MS (ESI) m/z $[M+1]^+$: 232.06.

b) (7-Fluoro-2,3-dihydro-4H-benzo[b][1,4]oxazin-4-yl)(5-(4-fluorophenyl)-pyridin-3-yl)methanone (Compound 2)

Methyl 5-(4-fluorophenyl)nicotinate (200 mg, 0.865 mmol) was treated with 7-fluoro-3,4-dihydro-2H-benzo[b][1,4]oxazine (199 mg, 1.30 mmol) in the presence of TEA (0.36 ml, 2.59 mmol) and trimethylaluminum (0.65 ml, 2.0 M in toluene, 1.30 mmol) in 8 ml toluene at 25° C. for 16 h. Purification by combi-flash chromatography using 5-25% EtOAc in heptane as eluent afforded 0.235 g of the title compound. $^1$H NMR (400 MHz, DMSO-$d_6$) δ: 8.99 (d, 1H), 8.69 (s, 1H), 8.22 (s, 1H), 7.00-7.90 (m, 5H), 6.84 (dd, 1H), 6.67 (m, 1H), 4.30-4.40 (m, 2H), 3.84-3.93 (m, 2H). MS (ESI) m/z $[M+1]^+$: 352.11.

Example 3

(2,3-Dihydro-4H-benzo[b][1,4]oxazin-4-yl)(4-methyl-5-phenylpyridin-3-yl)-methanone (Compound 3)

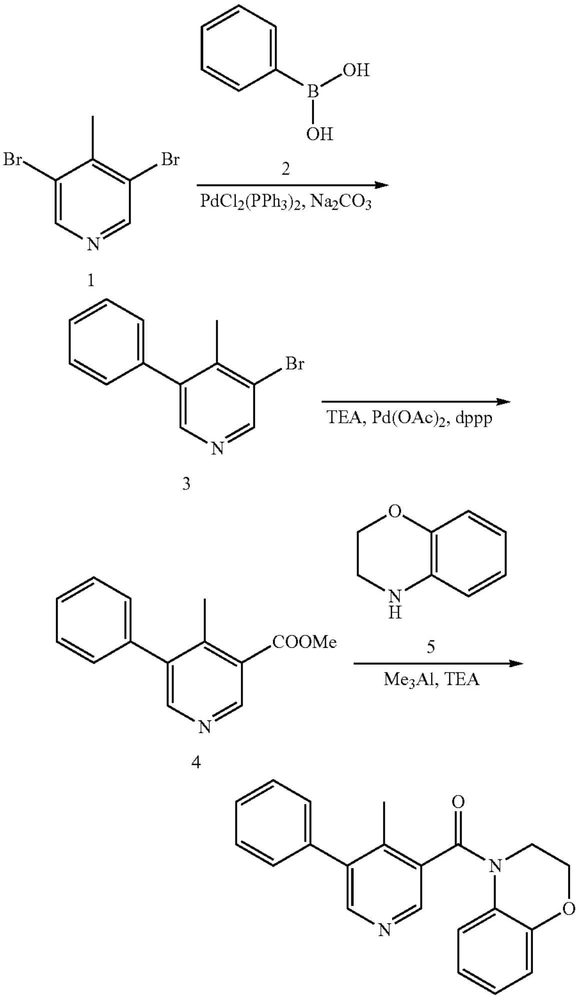

1

3

4

Compound 3 a) 3-Bromo-4-methyl-5-phenylpyridine (3)

3,5-Dibromo-4-methylpyridine (5.0 g, 20.0 mmol) was treated with (phenyl-boronic acid (2.7 g, 22.0 mmol) in the presence of sodium carbonate (4.2 g, 40.0 mmol) and bis(triphenylphosphine)palladium(II) dichloride (1.4 g, 2.0 mmol) in 60 ml of DME and 30 ml of water at 90° C. for 6 h. Purification by combi-flash using 5-30% EtOAc in heptane as an eluent afforded 3.1 g of the title compound. $^1$H-NMR (400 MHz, DMSO-$d_6$): δ: 8.69 (s, 1H), 8.35 (s, 1H), 7.43-7.54 (m, 3H), 7.38-7.44 (m, 2H), 2.30 (s, 3H). MS (ESI) m/z $[M+1]^+$: 248.01.

b) 4-Methyl-5-phenylnicotinate (4)

To a solution of 3-bromo-4-methyl-5-phenylpyridine (2.8 g, 11.0 mmol) in MeOH:DMSO (1:1) was added triethylamine (7.8 ml, 56.0 mmol). The reaction mixture was degassed with argon for 10 min followed by addition of palladium(II) acetate (0.51 g, 2.3 mmol) and 1,3-bis(diphenylphosphino)propane (0.93 g, 2.3 mmol and CO gas. The resulting reaction mixture was stirred at 100° C. for 16 h. After completion of the reaction as indicated by TLC, all volatile were evaporated under reduced pressure. Obtained residue was diluted with water (20 ml) and EtOAc (30 ml), and extracted with EtOAc (3×30 ml). The combined organic layer was washed with water and brine, dried over anhydrous sodium sulphate and concentrated under reduced pressure. The residue was purified by combi-flash chromatography using 5-40% EtOAc in heptane as an eluent to afford 2.3 g of the title compound. $^{1}$H-NMR (400 MHz, DMSO-$d_6$): δ: 8.87 (s, 1H), 8.52 (s, 1H), 7.41-7.53 (m, 3H), 7.36-7.41 (m, 2H), 3.89 (s, 3H), 2.39 (s, 3H). MS (ESI) m/z $[M+1]^+$: 228.03.

c) (2,3-Dihydro-4H-benzo[b][1,4]oxazin-4-yl)(4-methyl-5-phenylpyridin-3-yl)methanone (Compound 3)

4-Methyl-5-phenylnicotinate (500 mg, 2.20 mmol) was treated with 3,4-dihydro-2H-benzo[b][1,4]oxazine (446 mg, 3.30 mmol) in the presence of triethylamine (0.93 ml, 6.60 mmol) and trimethylaluminum (1.65 ml, 2.0 M in toluene, 3.30 mmol) in 12 ml of toluene at 100° C. for 16 h. Purification by combi-flash chromatography using 5-40% EtOAc in heptane as eluent afforded 0.05 g of the title compound. Rf(50% EtOAc/heptane)=0.2. $^{1}$H NMR (400 MHz, DMSO-$d_6$) δ: 8.48 (s, 1H), 8.40 (s, 1H), 7.26-7.54 (m, 6H), 7.06 (s, 1H), 6.92 (d, 1H), 6.75-6.84 (m, 1H), 4.31-4.40 (m, 2H), 3.31-3.40 (m, 2H), 2.16 (s, 1H). MS (ESI) m/z $[M+1]^+$: 330.97.

Example 4

(3,4-Dihydroquinolin-1(2H)-yl)(4-methyl-5-phenylpyridin-3-yl)methanone (Compound 4)

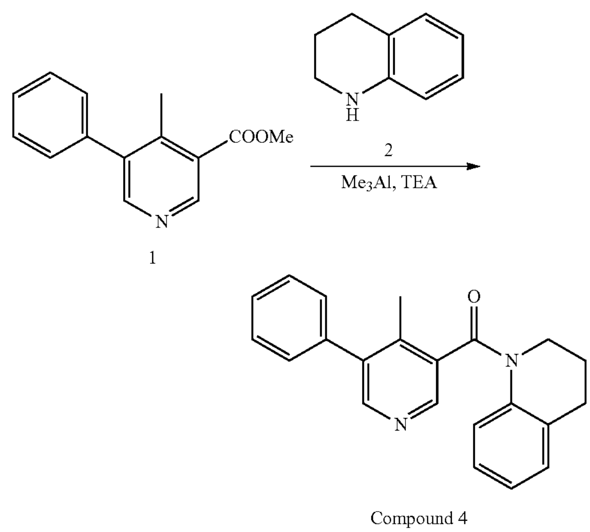

1

Compound 4

4-Methyl-5-phenylnicotinate (500 mg, 2.20 mmol) was treated with 1,2,3,4-tetrahydroquinoline (440 mg, 3.30 mmol) in the presence of triethylamine (0.93 ml, 6.60 mmol) and trimethylaluminum (1.65 ml, 2.0 M in toluene, 3.30 mmol) in 15 ml toluene at 100° C. for 16 h. Purification by combi-flash chromatography using 5-30% EtOAc in heptane as eluent afforded 0.15 g of the title compound. Rf(50% EtOAc/heptane)=0.2. $^{1}$H NMR (400 MHz, DMSO-$d_6$) δ: 8.35 (s, 2H), 7.40-7.55 (m, 3H), 7.25-7.35 (m, 2H), 7.18-7.22 (m, 1H), 6.98-7.07 (m, 2H), 3.74-3.80 (m, 2H), 2.84 (t, 2H), 2.09 (s, 3H), 1.94-2.03 (m, 2H). MS (ESI) m/z $[M+1]^+$: 329.15.

Example 5

(2,3-Dihydro-4H-benzo[b][1,4]oxazin-4-yl)(5-(4-fluorophenyl)-4-methylpyridin-3-yl)methanone (Compound 5)

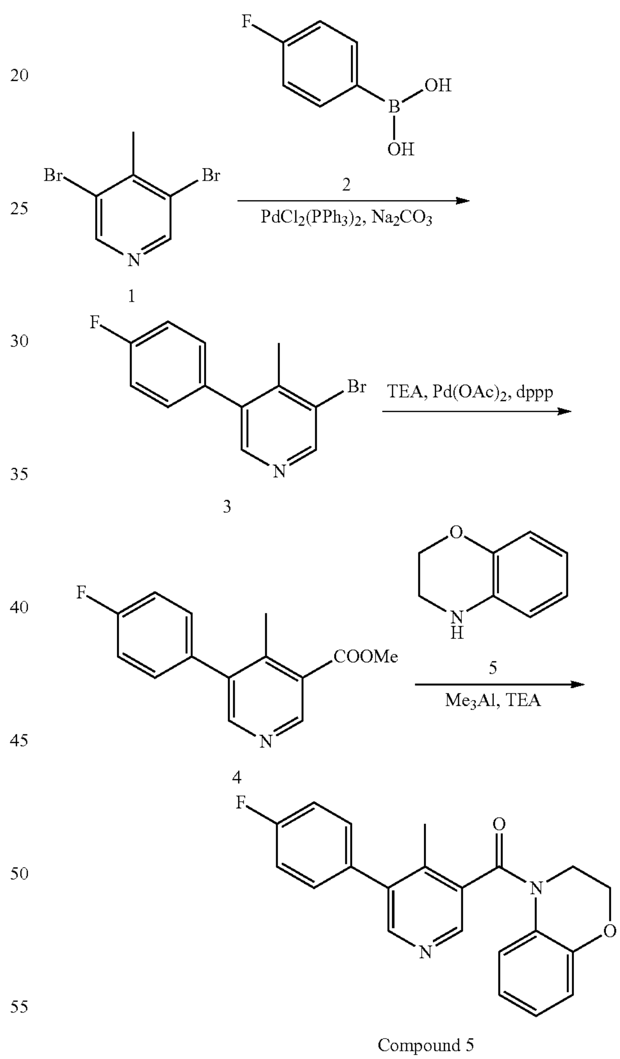

1

3

4

Compound 5 a) 3-Bromo-5-(4-fluorophenyl)-4-methylpyridine (3)

3,5-Dibromo-4-methylpyridine (5.0 g, 0.02 mol) was treated with (4-fluoro-phenyl)boronic acid (3.0 g, 0.02 mol), $Na_2CO_3$ (6.0 g, 0.06 mol) and $Pd(PPh_3)_2Cl_2$ (1.0 g, 2.0 mmol) in 60 ml of DME and 30 ml of water at 100° C. for 16 h. Purification by combi-flash chromatography using 5-40% ethyl acetate in heptane as an eluent afforded 4.2 g of the title compound. $^1$H-NMR (400 MHz, DMSO-$d_6$): δ: 8.65 (s, 1H), 8.31 (s, 1H), 7.23-7.30 (m, 2H), 7.10-7.20 (m, 2H), 2.33 (s, 3H). MS (ESI) m/z $[M+1]^+$; 265.90.

b) Methyl 5-(4-fluorophenyl)-4-methylnicotinate (4)

3-Bromo-5-(4-fluorophenyl)-4-methylpyridine (5.0 g, 0.02 mol) was treated with triethylamine (8.0 g, 11 ml, 79.0 mmol), palladium(II) acetate (0.71 g, 3.2 mmol), 1,3-bis (diphenylphosphino)propane (1.3 g, 3.2 mmol) and CO gas in 60 ml of DMSO and 60 ml of MeOH at 100° C. for 16 h. Purification by combi-flash chromatography using 10-40% ethyl acetate in heptane as an eluent afforded 3.2 g of the title compound. $^1$H-NMR (400 MHz, DMSO-$d_6$): δ: 8.87 (s, 1H), 8.52 (s, 1H), 7.41-7.50 (m, 2H), 7.30-7.37 (m, 2H), 3.89 (s, 3H), 2.38 (s, 3H). MS (ESI) m/z $[M+1]^+$: 343.10.

c) (2,3-Dihydro-4H-benzo[b][1,4]oxazin-4-yl)(5-(4-fluorophenyl)-4-methyl-pyridin-3-yl)methanone (Compound 5)

Methyl 5-(4-fluorophenyl)-4-methylnicotinate (400 mg, 1.63 mmol) was treated with 3,4-dihydro-2H-benzo[b][1,4] oxazine (331 mg, 2.45 mmol) in the presence of triethylamine (0.68 ml, 4.89 mmol) and trimethylaluminum (1.22 ml, 2 M in toluene, 2.45 mmol) in 10 ml of toluene at 95° C. for 18 h. Purification by combi-flash chromatography using 5-40% ethyl acetate in heptane as an eluent afforded 0.118 g of the title compound. $^1$H NMR (400 MHz, DMSO-$d_6$) δ: 8.18-8.57 (m, 2H), 7.41-7.55 (m, 2H), 7.34 (t, 2H), 7.00-7.10 (m, 1H), 6.93 (d, 2H), 6.30-6.60 (m, 1H), 4.20-4.50 (m, 2H), 3.54-3.80 (m, 2H), 2.16 (s, 3H). MS (ESI) m/z $[M+1]^+$: 349.12.

Example 6

(4-Amino-5-phenylpyridin-3-yl)(3,4-dihydroquinolin-1(2H)-yl)methanone (Compound 6)

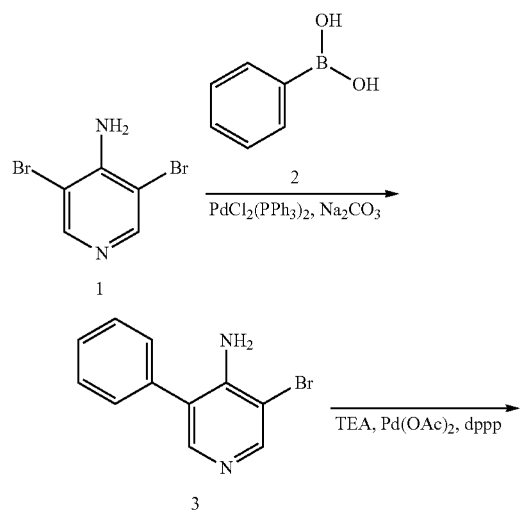

1

3

-continued

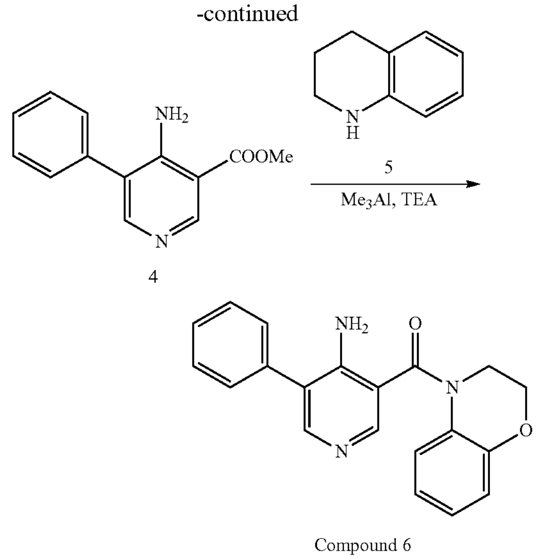

4

Compound 6 a) 3-Bromo-5-phenylpyridin-4-amine (3)

3,5-Dibromopyridin-4-amine (6.0 g, 24.0 mmol) was treated with phenylboronic acid (3.2 g, 26.0 mmol), $Na_2CO_3$ (5.0 g, 48.0 mmol) and $Pd(PPh_3)_2Cl_2$ (1.7 g, 2.4 mmol) in 12 ml of DME and 6 ml of water at 90° C. for 4 h. Purification by combi-flash chromatography using 5-40% ethyl acetate in heptane as an eluent afforded 3.6 g of the title compound. $^1$H-NMR (400 MHz, DMSO-$d_6$): δ: 8.29 (s, 1H), 7.91 (s, 1H), 7.47-7.55 (m, 2H), 7.38-7.47 (m, 3H), 5.73 (bs, 2H). MS (ESI) m/z $[M+1]^+$: 248.97.

b) Methyl 4-amino-5-phenylnicotinate (4)

3-Bromo-5-phenylpyridin-4-amine (2.8 g, 11.0 mmol) was treated with triethylamine (5.7 g, 7.8 ml, 56.0 mmol), palladium(II) acetate (1.0 g, 4.5 mmol), 1,3-bis(diphenylphosphino)propane (1.9 g, 4.5 mmol) and CO gas in 50 ml of MeOH and 50 ml of DMSO at 80° C. for 12 h. Purification by combi-flash chromatography using 10-40% ethyl acetate in heptane as an eluent afforded 1.6 g of the title compound. $^1$H-NMR (400 MHz, DMSO-$d_6$): δ 8.74 (s, 1H), 8.03 (s, 1H), 7.48-7.55 (m, 2H), 7.38-7.48 (m, 3H), 6.87 (bs, 2H), 3.85 (s, 3H). MS (ESI) m/z $[M+1]^+$: 229.19.

c) (4-Amino-5-phenylpyridin-3-yl)(3,4-dihydroquinolin-1(2H)-yl)methanone (Compound 6)

Methyl 4-amino-5-phenylnicotinate (500 mg, 2.19 mmol) was treated with 1,2,3,4-tetrahydroquinoline (438 mg, 3.29 mmol), triethylamine (0.92 ml, 6.57 mmol) trimethylaluminum (1.64 ml, 2.0 M in toluene, 3.29 mmol) in 20 ml of toluene at 100° C. for 16 h. Purification by combi-flash chromatography using 5-30% ethyl acetate in heptane as an eluent afforded 0.025 g of the title compound. (NMR/MS data in Table 2). $^1$H NMR (400 MHz, DMSO-$d_6$) δ: 7.90 (s, 1H), 7.79 (s, 1H), 7.51 (t, 2H), 7.37-7.47 (m, 3H), 7.20 (d, 1H), 6.92-7.06 (m, 3H), 5.83 (bs, 2H), 3.78 (t, 2H), 2.82 (t, 2H), 1.96 (q, 2H). MS (ESI) m/z $[M+1]^+$: 302.20.

Example 7

(2,3-Dihydro-4H-benzo[b][1,4]oxazin-4-yl)(5-(4-fluorophenyl)pyridazin-3-yl)-methanone (Compound 7)

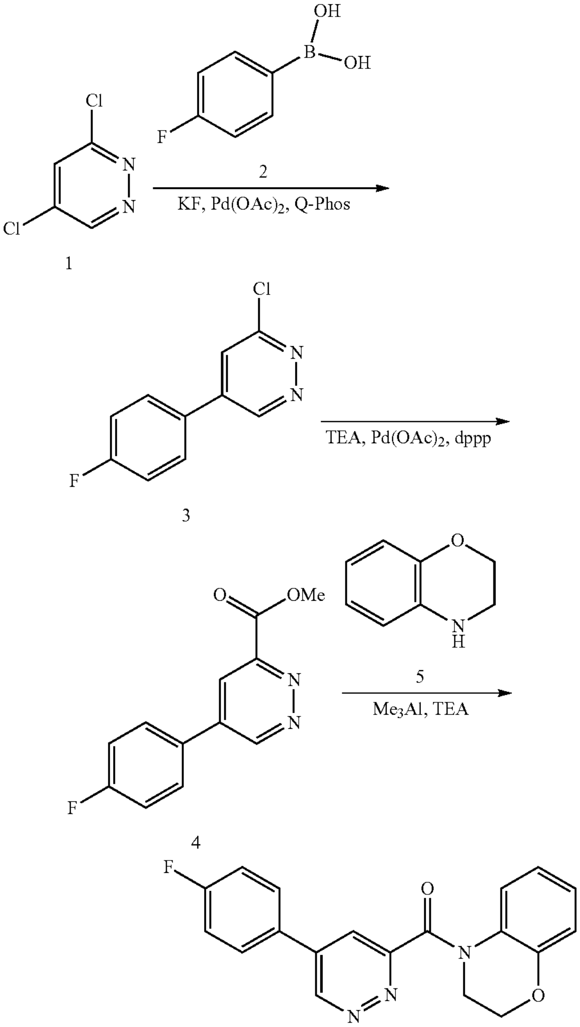

1

3

4

Compound 7 a) 3-Chloro-5-(4-fluorophenyl)pyridazine (3)

3,5-Dichloropyridazine (3.0 g, 20.1 mmol) was treated with (4-fluorophenyl)-boronic acid (3.10 g, 22.2 mmol), KF (2.93 g, 50.3 mmol), diacetoxypalladium (226 mg, 1.01 mmol) and Q-PHOS (716 mg, 1.01 mmol) in 40 ml of toluene and 10 ml of water at 80° C. for 16 h. Purification by combi-flash chromatography using 5-40% ethyl acetate in heptane as an eluent afforded 1.0 g of the title compound. Rf(70% EtOAc/heptane)=0.4. $^1$H-NMR (400 MHz, DMSO-$d_6$) δ: 9.68 (d, 1H), 8.29 (d, 1H), 8.09 (dt, 2H), 7.43 (dd, 2H). MS (ESI) m/z $[M+1]^+$: 209.02.

b) Methyl 5-(4-fluorophenyl)pyridazine-3-carboxylate (4)

3-Chloro-5-(4-fluorophenyl)pyridazine (850 mg, 4.07 mmol) was treated with triethylamine (1.14 ml, 8.15 mmol), $PdCl_2$(dppf) (298 mg, 0.407 mmol) and CO gas in 50 ml of MeOH at 100° C. for 16 h. Purification by combi-flash chromatography using 10-40% ethyl acetate in heptane as an eluent afforded 0.87 g of the title compound. $^1$H-NMR (400 MHz, DMSO-$d_6$): δ 9.86 (d, 1H), 8.45 (d, 1H), 8.11 (dd, 2H), 7.44 (dd, 2H), 3.99 (s, 3H). MS (ESI) m/z $[M+1]^+$: 233.02.

c) (2,3-Dihydro-4H-benzo[b][1,4]oxazin-4-yl)(5-(4-fluorophenyl)pyridazin-3-yl)methanone (Compound 7)

Methyl 5-(4-fluorophenyl)pyridazine-3-carboxylate (500 mg, 2.15 mmol) was treated with 3,4-dihydro-2H-benzo[b][1,4]oxazine (437 mg, 3.23 mmol), triethylamine (0.91 ml, 6.46 mmol) and trimethylaluminum (1.61 ml, 2.0 M in toluene, 3.23 mmol) in 15 ml toluene at 100° C. for 16 h. Purification by combi-flash chromatography using 5-40% ethyl acetate in heptane as an eluent afforded 0.142 g of the title compound. Rf (50% EtOAc/heptane)=0.2.

Example 8

(6-(Benzo[d]oxazol-6-yl)pyrazin-2-yl)(2,3-dihydro-4H-benzo[b][1,4]oxazin-4-yl)methanone (Compound 8)

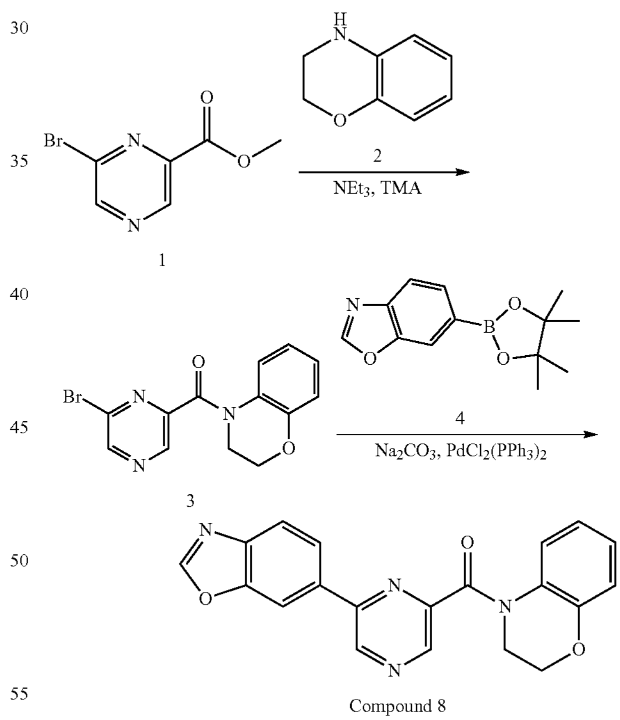

1

3

Compound 8 a) (6-Bromopyrazin-2-yl)(2,3-dihydro-4H-benzo[b][1,4]oxazin-4-yl)methanone (3)

Methyl 5-(4-fluorophenyl)pyridazine-3-carboxylate (20 mg, 0.086 mmol) was treated with 3,4-dihydro-2H-benzo[b][1,4]oxazine (18.2 mg, 0.129 mmol), triethylamine (36 μl, 0.258 mmol) and trimethylaluminum (65 μl, 2.0 M in toluene, 0.129 mmol) in 5 ml of toluene at 100° C. for 16 h. Purification by combi-flash chromatography using 20-60% ethyl acetate in heptane as an eluent afforded 0.025 g of the title compound. Rf(50% EtOAc/heptane)=0.2. Yield: 70%. $^1$H-NMR (400 MHz, DMSO-$d_6$): δ: 9.01 (s, 1H), 8.96 (s, 1H), 7.50-8.50 (m, 1H), 7.08 (t, 1H), 6.93 (d, 1H), 6.70-6.90 (m, 1H), 4.20-4.48 (m, 2H), 3.80-3.92 (m, 2H). MS (ESI) m/z $[M+1]^+$:320.05.

b) (6-(Benzo[d]oxazol-6-yl)pyrazin-2-yl)(2,3-dihydro-4H-benzo[b][1,4]oxazin-4-yl)methanone (Compound 8)

(6-Bromopyrazin-2-yl)(2,3-dihydro-4H-benzo[b][1,4]oxazin-4-yl)methanone (500 mg, 1.56 mmol) was treated with 6-(4,4,5,5-tetramethyl-1,3,2-dioxaborolan-2-yl)-benzo[d]oxazole (383 mg, 1.56 mmol), sodium carbonate (331 mg, 3.12 mmol) and $Pd(PPh_3)_2Cl_2$ (110 mg, 0.156 mmol) in 2.5 ml of ethanol, 10 ml of toluene and 2.5 ml of water at 90° C. for 16 h. Purification by combi-flash chromatography using 0-50% ethyl acetate in heptane as an eluent afforded 0.3 g of the title compound. $^1$H NMR (400 MHz, DMSO-$d_6$) δ: 9.41 (s, 1H), 8.92 (s, 1H), 8.77 (s, 1H), 8.36 (s, 1H), 8.10 (d, 1H), 7.90 (d, 1H), 7.41-7.51 (m, 1H), 7.06 (t, 1H), 6.96 (d, 1H), 6.78 (t, 1H), 4.39 (t, 2H), 4.05 (t, 2H). MS (ESI) m/z $[M+1]^+$: m/z 359.15.

Example 9

(2,3-Dihydro-4H-benzo[b][1,4]oxazin-4-yl)(6-(3-(trifluoromethoxy)phenyl)-pyrazin-2-yl)methanone (Compound 9)

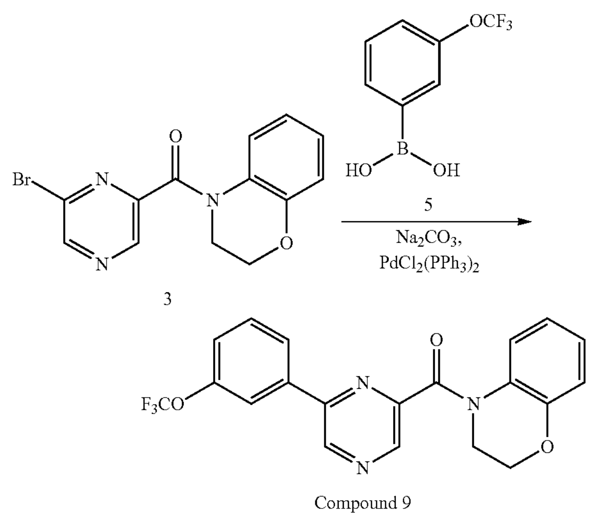

3

Compound 9

(6-Bromopyrazin-2-yl)(2,3-dihydro-4H-benzo[b][1,4]oxazin-4-yl)methanone (500 mg, 1.56 mmol) was treated with (3-(trifluoromethoxy)phenyl)boronic acid (354 mg, 1.72 mmol), sodium carbonate (331 mg, 3.12 mmol) and $Pd(PPh_3)_2Cl_2$ (110 mg, 0.156 mmol) in 0.63 ml of ethanol, 2.5 ml of toluene and 0.63 ml of water at 90° C. for 16 h. Purification by combi-flash chromatography using 0-35% ethyl acetate in heptane as an eluent afforded 0.4 g of the title compound. $^1$H NMR (400 MHz, DMSO-$d_6$) δ 9.37 (s, 1H), 8.96 (s, 1H), 8.07 (d, 1H), 7.89 (s, 1H), 7.65 (t, 1H), 7.48 (d, 1H), 7.35-7.46 (m, 1H), 7.05 (t, 1H), 6.94 (d, 1H), 6.77 (t, 1H), 4.38 (t, 2H), 4.03 (t, 2H). MS (ESI) m/z $[M+1]^+$: m/z 402.12.

Example 10

(2,3-Dihydro-4H-benzo[b][1,4]oxazin-4-yl)(5-phenylpyridin-3-yl)methanone (Compound 10)

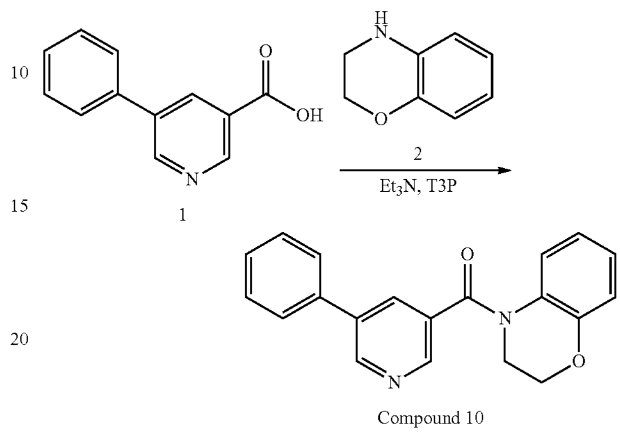

1

Compound 10

A solution of 50% propylphosphonic anhydride (T3P) in EtOAc (0.6 ml, 1.0 mmol) was added to a mixture of 5-phenylnicotinic acid (0.10 g, 1.50 mmol), 2,3-dihydro-1,4-benzoxazine (0.07 g, 0.50 mmol) and $Et_3N$ (0.41 ml, 4.02 mmol) in DMF (2 ml). The mixture was stirred over night at RT under $N_2$. The mixture was diluted with EtOAc (10 ml) and 5% $Na_2CO_3$ (5 ml) and extracted with EtOAc. The combined extracts were washed with brine, dried with $Na_2SO_4$ filtered and evaporated. The crude product was purified by column chromatography to afford the title compound. $^1$H NMR (Chloroform-d, 400 MHz) δ: 8.88 (d, 1H), 8.69 (d, 1H), 7.99 (t, 1H), 7.4-7.5 (m, 5H), 6.8-7.1 (m, 3H), 6.6-6.8 (m, 1H), 4.3-4.5 (m, 2H), 4.0-4.1 (m, 2H).

Example 11

(5-(4-Chlorophenyl)pyridin-3-yl)(2,3-dihydro-4H-benzo[b][1,4]oxazin-4-yl)-methanone (Compound 11)

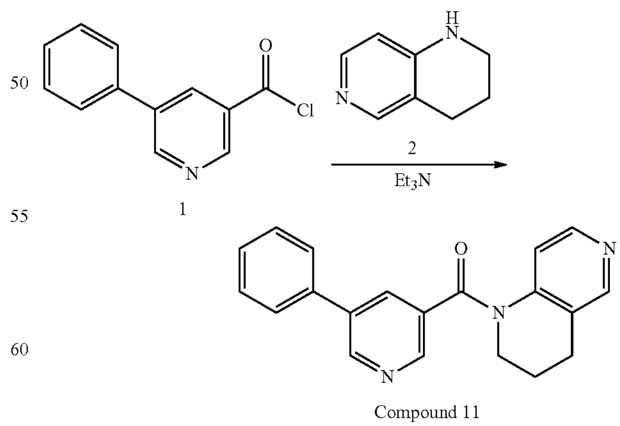

1

Compound 11

A mixture of 5-phenylnicotinoyl chloride (0.1 g, 0.46 mmol), 1,2,3,4-tetrahydro-1,6-naphthyridine (61.6 mg, 0.46 mmol) in DCM (5 ml) was cooled to 0° C. followed by addition of $Et_3N$ (0.2 ml, 1.38 mmol). The mixture was stirred at RT for 12 h. Water (10 ml) was added followed by extraction with DCM. The combined organic layer was washed with brine, dried with anhydrous $Na_2SO_4$ and concentrated in vacuo. The crude residue was purified by column chromatography to afford the title compound. $^1H$ NMR (DMSO-$d_6$, 600 MHz) δ: 8.99 (d, 1H), 8.63 (d, 1H), 8.39 (s, 1H), 8.17 (t, 1H), 8.13 (d, 1H), 7.72 (d, 2H), 7.51 (t, 2H), 7.4-7.5 (m, 1H), 7.20 (br d, 1H), 3.8-3.8 (m, 2H), 2.86 (t, 2H), 1.99 (quin, 2H). LC-MS: m/z 316.4 $(M+H)^+$.

The following compounds were prepared according to the procedures described above. The compound number, characterization data, starting materials, reaction conditions (Example number referred to) and purification method are indicated on the table.

Purification methods used:

a) Crystallization
b) Column chromatography
c) Precipitation in aqueous media
d) Semipreparative HPLC
e) Trituration
f) Salt formation

| No | Structure and starting material | Reaction conditions, purification method, $^1H$ NMR/LC-MS |
|---|---|---|
| 12 | 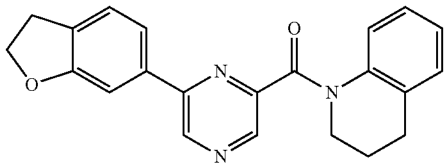 Starting materials: 6-(2,3-Dihydrobenzofuran-6-yl)pyrazine-2-carboxylic acid and 1,2,3,4-tetrahydroquinoline | Conditions: Ex. 10, purification b), $^1H$ NMR (Chloroform-d, 400 MHz) δ: 8.88 (br s, 1H), 8.68 (s, 1H), 7.45 (td, 2H), 7.22 (d, 1H), 7.04 (br t, 1H), 6.8-7.0 (m, 1H), 6.7-6.8 (m, 1H), 4.62 (t, 2H), 3.99 (br t, 2H), 3.22 (br t, 2H), 2.89 (t, 2H), 2.11 (quin, 2H), 2.00 (s, 1H). LC-MS: m/z 359.1 $(M + H)^+$. |
| 13 | 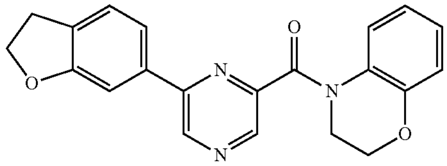 Starting materials: 6-(2,3-Dihydrobenzofuran-6-yl)pyrazine-2-carboxylic acid and 2,3-Dihydro-1,4-benzoxazine | Conditions: Ex. 10, purification b), $^1H$ NMR (400 MHz, Chloroform-d) δ: 3.30 (br s, 2H), 4.13 (br s, 2H), 4.43 (br s, 2H), 4.64 (t, 2H), 6.78-7.12 (m, 5H), 7.40-7.94 (m, 2H), 8.77-8.88 (m, 1H), 8.95-9.04 (m, 1H). LC-MS: m/z 361.1 $(M + H)^+$. |
| 14 | 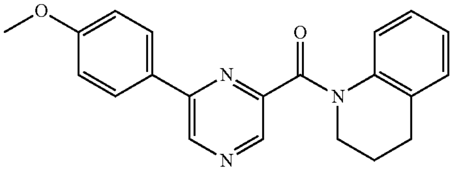 Starting materials: 6-(4-Methoxyphenyl)pyrazine-2-carboxylic acid and 1,2,3,4-Tetrahydroquinoline | Conditions: Ex. 10, purification b), $^1H$ NMR (400 MHz, Chloroform-d) δ: 2.12 (quin, 2H), 2.90 (t, 2H), 3.79-3.92 (m, 4H), 3.95-4.07 (m, 2H), 6.65-7.14 (m, 5H), 7.16-7.25 (m, 1H), 7.52 (br s, 1H), 7.59 (br s, 1H), 8.70 (s, 1H), 8.91 (br s, 1H). LC-MS: m/z 346.1 $(M + H)^+$. |
| 15 | 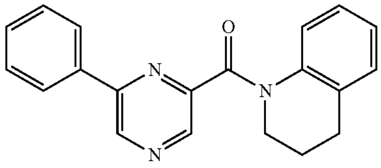 Starting materials: 6-Phenylpyrazine-2-carboxylic acid and 1,2,3,4-Tetrahydroquinoline | Conditions: Ex. 10, purification b), $^1H$ NMR (DMSO-$d_6$, 600 MHz) δ: 9.26 (br s, 1H), 8.79 (br s, 1H), 8.16 (s, 1H), 7.7-7.9 (m, 1H), 7.48 (br s, 3H), 7.27 (d, 1H), 7.0-7.1 (m, 1H), 6.8-7.0 (m, 1H), 3.86 (br s, 2H), 2.86 (t, 2H), 2.08 (s, 1H), 2.02 (quin, 2H). LC-MS: m/z 316.3 $(M + H)^+$. |
| 16 | 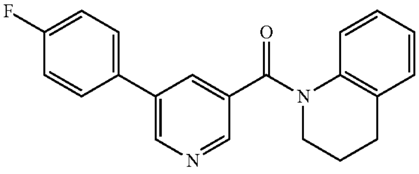 Starting materials: (Fluorophenyl)nicotinic acid and 1,2,3,4-Tetrahydroquinoline | Conditions: Ex. 10, purification b), $^1H$ NMR (DMSO-$d_6$, 600 MHz) δ: 8.88 (d, 1H), 8.45 (br s, 1H), 7.98 (br s, 1H), 7.70 (br dd, 2H), 7.33 (t, 2H), 7.25 (d, 1H), 7.05 (t, 1H), 6.9-7.0 (m, 1H), 6.86 (br s, 1H), 3.82 (t, 2H), 2.86 (t, 2H), 2.00 (quin, 2H). LC-MS: m/z 334.1 $(M + H)^+$. |

-continued

| No | Structure and starting material | Reaction conditions, purification method, $^1$H NMR/LC-MS |
|---|---|---|
| 17 | 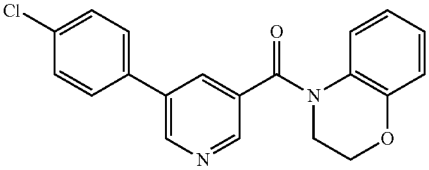 Starting materials: (5-Bromopyridin-3-yl)(2,3-dihydro-4H-benzo[b][1,4]oxazin-4-yl)methanone and 4-Chlorophenylboronic acid | Conditions: Ex. 10, purification b), $^1$H NMR (DMSO-$d_6$, 600 MHz) δ: 9.00 (d, 1H), 8.71 (s, 1H), 8.23 (br s, 1H), 7.78 (br d, 2H), 7.58 (d, 2H), 7.03 (t, 1H), 6.94 (dd, 1H), 6.76 (br s, 1H), 4.3-4.4 (m, 2H), 3.93 (br s, 2H). LC-MS: m/z 351.8 $(M + H)^+$. |
| 18 | 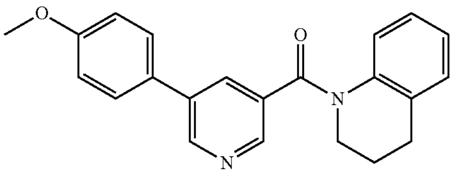 Starting materials: 5-(4-Methoxyphenyl)nicotinic acid and 1,2,3,4-Tetrahydroquinoline | Conditions: Ex. 10, purification b), $^1$H NMR (400 MHz, Chloroform-d) δ: 2.01-2.15 (m, 2H), 2.87 (t, 2H), 3.76-4.03 (m, 5H), 6.70 (br s, 1H), 6.88-7.08 (m, 4H), 7.21 (d, 1H), 7.37 (d, 2H), 7.81 (t, 1H), 8.44 (d, 1H), 8.75 (d, 1H). LC-MS: m/z 346.1 $(M + H)^+$. |
| 19 | 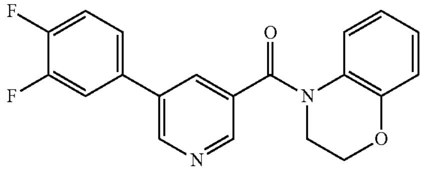 Starting materials: (5-Bromopyridin-3-yl)(2,3-dihydro-4H-benzo[b][1,4]oxazin-4-yl)methanone and 3,4-Difluorophenyl boronic acid | Conditions: Ex. 1, purification b), $^1$H NMR (600 MHz, DMSO-$d_6$) δ: 3.93 (br s, 2H), 4.37 (br s, 2H), 6.76 (br s, 1H), 6.94 (dd, 1H), 7.04 (t, 1H), 7.55-7.67 (m, 3H), 7.86-7.98 (m, 1H), 8.26 (br s, 1H), 8.71 (br s, 1H), 9.03 (d, 1H). LC-MS: m/z 354.1 $(M + H)^+$. |
| 20 | 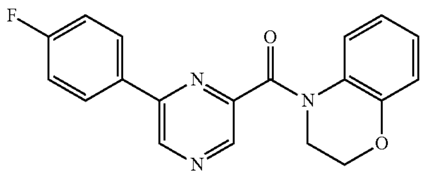 Starting materials: 6-(4-Fluorophenyl)pyrazine-2-carboxylic acid and 2,3-Dihydro-1,4-benzoxazine | Conditions: Ex. 10, purification b), $^1$H NMR (DMSO-$d_6$, 600 MHz) δ: 9.3-9.4 (m, 1H), 8.9-9.0 (m, 1H), 7.9-8.4 (m, 2H), 7.36 (br s, 2H), 7.0-7.1 (m, 1H), 6.9-7.0 (m, 2H), 4.35 (br s, 2H), 3.9-4.1 (m, 2H). LC-MS: m/z 336.3 $(M + H)^+$. |
| 21 | 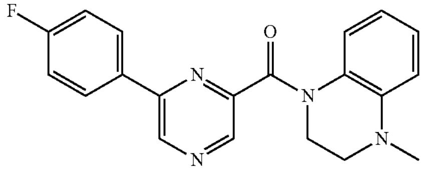 Starting materials: 6-(4-Fluorophenyl)pyrazine-2-carboxylic acid and 1,2,3,4-Tetrahydro-1-methylquinoxaline | Conditions: Ex. 10, purification b), $^1$H NMR (Chloroform-d, 400 MHz) δ: 8.91 (br s, 2H), 8.73 (br s, 1H), 7.59 (br s, 2H), 7.09 (br s, 3H), 7.01 (br d, 2H), 6.74 (d, 2H), 6.25 (br s, 2H), 4.14 (br s, 3H), 3.57 (br s, 3H), 3.04 (br s, 4H). LC-MS: m/z 349.4 $(M + H)^+$. |
| 22 | 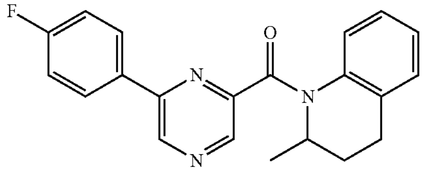 Starting materials: (6-Chloropyrazin-2-yl)(2-methyl-3,4-dihydroquinolin-1(2H)-yl)methanone and 4-Fluorobenzene boronic acid | Conditions: Ex. 1, purification b), $^1$H NMR (DMSO-$d_6$, 600 MHz) δ: 9.21 (br s, 1H), 8.72 (br s, 1H), 7.83 (br s, 2H), 7.2-7.4 (m, 3H), 7.04 (br t, 1H), 6.89 (br s, 1H), 4.70 (br s, 1H), 2.7-2.8 (m, 2H), 2.3-2.5 (m, 1H), 1.44 (br s, 1H), 1.23 (d, 3H). LC-MS: m/z 348.4 $(M + H)^+$. |

-continued

| No | Structure and starting material | Reaction conditions, purification method, $^1H$ NMR/LC-MS |
|---|---|---|
| 23 | 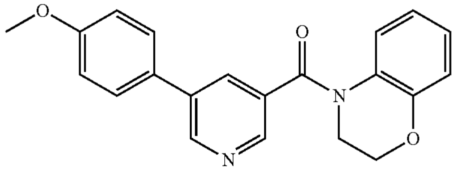 Starting materials: 5-(4-Methoxyphenyl)nicotinic acid and 2,3-Dihydro-1,4-benzoxazine | Conditions: Ex. 10, purification b), $^1H$ NMR (DMSO-$d_6$, 600 MHz) δ: 8.96 (d, 1H), 8.64 (s, 1H), 8.15 (br s, 1H), 7.69 (br d, 2H), 7.0-7.1 (m, 3H), 6.94 (dd, 1H), 6.7-6.8 (m, 1H), 4.38 (br s, 2H), 3.94 (br s, 2H), 3.82 (s, 3H), 0.93 (s, 1H). LC-MS: m/z 348.1 $(M + H)^+$. |
| 24 | 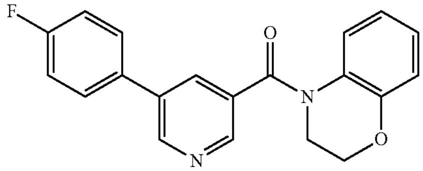 Starting materials: 5-(4-Fluorophenyl)nicotinic acid and 2,3-Dihydro-1,4-benzoxazine | Conditions: Ex. 10, purification b), $^1H$ NMR (DMSO-$d_6$, 600 MHz) δ: 8.91 (d, 1H), 8.62 (s, 1H), 8.13 (br s, 1H), 7.7-7.8 (m, 2H), 7.28 (t, 2H), 6.96 (t, 1H), 6.86 (dd, 1H), 6.69 (br s, 1H), 4.30 (br s, 2H), 3.86 (br s, 2H). LC-MS: m/z 336.1 $(M + H)^+$. |
| 25 | 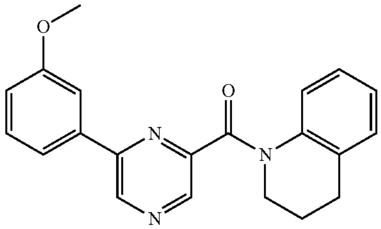 Starting materials: 6-(3-Methoxyphenyl)pyrazine-2-carboxylic acid and 1,2,3,4-Tetrahydroquinoline | Conditions: Ex. 10, purification b), $^1H$ NMR (600 MHz, DMSO-$d_6$) δ: 1.98-2.08 (m, 2H), 2.85 (t, 2H), 3.32 (br s, 4H), 3.77 (s, 3H), 3.86 (br s, 2H), 6.89 (br s, 1H), 7.03 (br d, 2H), 7.18-7.31 (m, 2H), 7.37 (br t, 2H), 7.47 (br s, 1H), 8.81 (s, 1H), 9.26 (br s, 1H). LC-MS: m/z 347.3 $(M + H)^+$. |
| 26 | 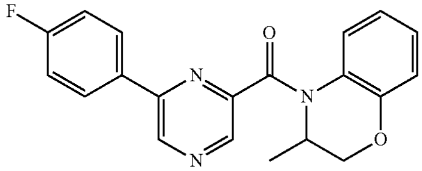 Starting materials: (6-Chloropyrazin-2-yl)(3-methyl-2,3-dihydro-4H-benzo[b][1,4]oxazin-4-yl)methanone and 4-Fluorobenzene boronic acid | Conditions: Ex. 1, purification b), $^1H$ NMR (DMSO-$d_6$, 600 MHz) δ: 9.38 (br s, 1H), 8.90 (s, 1H), 8.16 (br s, 2H), 7.39 (br s, 2H), 7.08 (br s, 1H), 6.97 (d, 1H), 6.7-6.9 (m, 1H), 4.26 (br s, 1H), 4.20 (br s, 1H), 1.3-1.4 (m, 3H). LC-MS: m/z 350.4 $(M + H)^+$. |
| 27 | 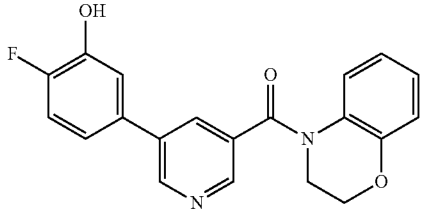 Starting materials: (5-Bromopyridin-3-yl)(2,3-dihydro-4H-benzo[b][1,4]oxazin-4-yl)methanone and 4-Fluoro-3-hydroxyphenylboronic acid | Conditions: Ex. 1, purification b), $^1H$ NMR (DMSO-$d_6$, 600 MHz) δ: 10.11 (br s, 1H), 8.89 (s, 1H), 8.67 (br s, 1H), 8.11 (br s, 1H), 7.2-7.3 (m, 2H), 7.13 (br s, 1H), 7.03 (t, 1H), 6.93 (dd, 1H), 6.75 (br s, 1H), 4.37 (br s, 2H), 3.93 (br s, 2H), 2.1-2.1 (m, 1H). LC-MS: m/z 351.1 $(M + H)^+$. |

-continued

| No | Structure and starting material | Reaction conditions, purification method, $^1H$ NMR/LC-MS |
|---|---|---|
| 28 | 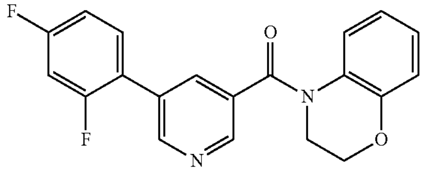 Starting materials: (5-Bromopyridin-3-yl)(2,3-dihydro-4H-benzo[b][1,4]oxazin-4-yl)methanone and 2,4-Difluorophenyl boronic acid | Conditions: Ex. 1, purification b), $^1H$ NMR (DMSO-$d_6$, 600 MHz) δ: 8.84 (s, 1H), 8.75 (s, 1H), 8.10 (br s, 1H), 7.6-7.7 (m, 1H), 7.45 (t, 1H), 7.26 (dt, 1H), 7.03 (t, 1H), 6.93 (dd, 1H), 6.76 (br s, 1H), 4.37 (br s, 2H), 3.93 (br s, 2H). LC-MS: m/z 354.1 $(M + H)^+$. |
| 29 | 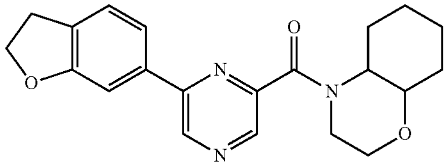 Starting materials: 6-(2,3-Dihydrobenzofuran-6-yl)pyrazine-2-carboxylic acid and Octahydro-2H-benzo[b][1,4]oxazine | Conditions: Ex. 10, purification b), $^1H$ NMR (Chloroform-d, 400 MHz) δ: 9.0-9.0 (m, 1H), 8.7-8.8 (m, 1H), 7.8-7.9 (m, 2H), 6.91 (d, 1H), 4.6-4.7 (m, 2H), 3.9-4.1 (m, 4H), 3.31 (t, 3H), 2.44 (br s, 1H), 1.9-2.1 (m, 2H), 1.7-1.9 (m, 2H), 1.5-1.6 (m, 1H), 1.3-1.5 (m, 3H). LC-MS: m/z 466.5 $(M + H)^+$. |
| 30 | 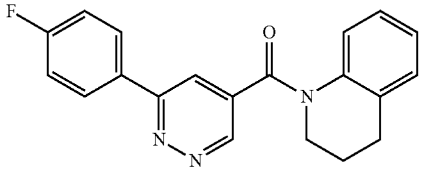 Starting materials: 6-(4-Fluorophenyl)pyridazine-4-carboxylic acid and 1,2,3,4-Tetrahydroquinoline | Conditions: Ex. 10, purification b), $^1H$ NMR (DMSO-$d_6$, 600 MHz) δ: 8.9-9.2 (m, 1H), 8.16 (br s, 2H), 7.40 (t, 3H), 7.26 (d, 2H), 7.07 (br t, 1H), 6.9-7.0 (m, 1H), 3.82 (br s, 2H), 2.88 (t, 2H), 2.01 (br s, 2H). LC-MS: m/z 334.1 $(M + H)^+$. |
| 31 | 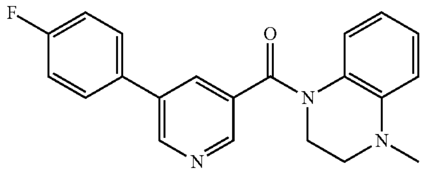 Starting materials: 5-(4-Fluorophenyl)nicotinic acid and 1,2,3,4-Tetrahydro-1-methylquinoxaline | Conditions: Ex. 10, purification b), $^1H$ NMR (Chloroform-d, 400 MHz) δ: 8.75 (d, 1H), 8.58 (d, 1H), 7.81 (t, 1H), 7.38 (dd, 2H), 7.0-7.2 (m, 3H), 6.6-6.8 (m, 1H), 6.2-6.6 (m, 2H), 4.09 (t, 2H), 3.54 (t, 2H), 3.03 (s, 3H). LC-MS: m/z 348.1 $(M + H)^+$. |
| 32 | 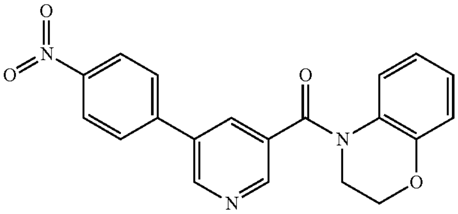 Starting materials: (5-Bromopyridin-3-yl)(2,3-dihydro-4H-benzo[b][1,4]oxazin-4-yl)methanone and 4-Nitrophenylboronic acid | Conditions: Ex. 1, purification b), $^1H$ NMR (DMSO-$d_6$, 600 MHz) δ: 9.11 (s, 1H), 8.78 (br s, 1H), 8.3-8.4 (m, 3H), 8.0-8.1 (m, 2H), 7.04 (t, 1H), 6.94 (dd, 1H), 6.6-6.8 (m, 1H), 4.37 (br s, 2H), 3.94 (br s, 2H), 3.2-3.3 (m, 1H), 2.5-2.5 (m, 1H). LC-MS: m/z 362.0 $(M + H)^+$. |
| 33 | 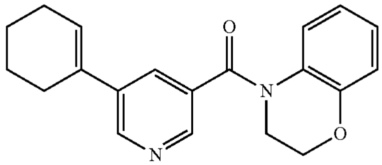 Starting materials: (5-Bromopyridin-3-yl)(2,3-dihydro-4H-benzo[b][1,4]oxazin-4-yl)methanone and Cyclohexen-1-ylboronic acid | Conditions: Ex. 1, purification b), $^1H$ NMR (Chloroform-d, 400 MHz) δ: 8.68 (d, 1H), 8.5-8.6 (m, 1H), 7.77 (t, 1H), 7.0-7.1 (m, 1H), 6.93 (dd, 1H), 6.6-6.8 (m, 1H), 6.15 (br s, 1H), 4.3-4.5 (m, 2H), 3.9-4.1 (m, 2H), 2.3-2.4 (m, 2H), 2.2-2.3 (m, 2H), 1.7-1.8 (m, 2H), 1.6-1.7 (m, 2H). LC-MS: m/z 321.1 $(M + H)^+$. |

-continued

| No | Structure and starting material | Reaction conditions, purification method, $^1$H NMR/LC-MS |
|---|---|---|
| 34 | 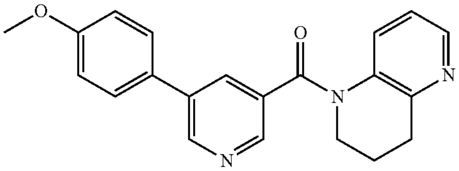 Starting materials: 5-(4-Methoxyphenyl)nicotinic acid and 1,2,3,4-Tetrahydro-[1,5]naphthyridine | Conditions: Ex. 10, purification b), $^1$H NMR (Chloroform-d, 400 MHz) δ: 8.8-8.9 (m, 1H), 8.5-8.6 (m, 1H), 8.31 (dd, 1H), 7.9-7.9 (m, 1H), 7.0-7.0 (m, 2H), 6.7-6.8 (m, 2H), 6.6-6.7 (m, 2H), 4.2-4.3 (m, 2H), 3.9-3.9 (m, 3H), 3.4-3.4 (m, 2H), 3.11 (t, 2H). LC-MS: m/z 346.5 $(M + H)^+$. |
| 35 | 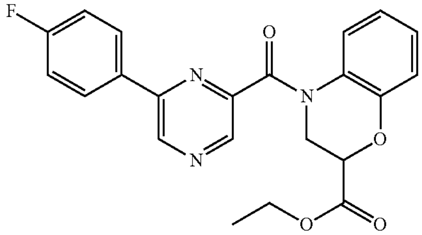 Starting materials: Ethyl 4-(6-chloropyrazine-2-carbonyl)-3,4-dihydro-2H-benzo[b][1,4]oxazine-2-carboxylate and 4-Fluorobenzeneboronic acid | Conditions: Ex. 1, purification b), $^1$H NMR ($DMSO-d_6$, 600 MHz) δ: 9.33 (br s, 1H), 8.18 (br s, 1H), 7.87 (br s, 1H), 7.29 (br s, 3H), 7.00 (br d, 3H), 5.25 (br s, 1H), 3.98 (br s, 4H), 0.95 (br t, 5H). LC-MS: m/z 408.1 $(M + H)^+$. |
| 36 | 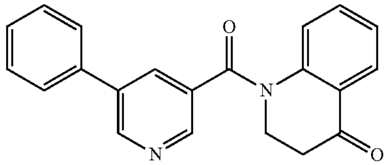 Starting materials: 5-Phenylnicotinic acid and 2,3-Dihydro-1H-quinolin-4-one | Conditions: Ex. 10, purification b), $^1$H NMR ($DMSO-d_6$, 600 MHz) δ: 8.98 (d, 1H), 8.71 (d, 1H), 8.20 (s, 1H), 7.92 (dd, 1H), 7.67 (d, 2H), 7.4-7.6 (m, 5H), 7.26 (t, 1H), 7.15 (br s, 1H), 4.27 (t, 2H), 3.4-3.5 (m, 1H), 2.96 (t, 2H). LC-MS: m/z 329.4 $(M + H)^+$. |
| 37 | 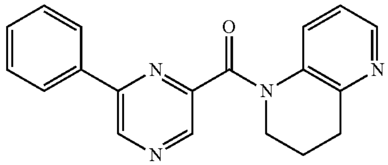 Starting materials: 6-Phenylpyrazine-2-carboxylic acid and 1,2,3,4-Tetrahydro-[1,5]naphthyridine | Conditions: Ex. 10, purification b), $^1$H NMR (400 MHz, Chloroform-d) δ: 2.19 (quin, 2H), 3.14 (t, 2H), 4.00 (br t, 2H), 6.87-7.15 (m, 1H), 7.47 (br s, 3H), 7.79 (br s, 2H), 8.32 (br s, 1H), 8.93 (s, 1H), 9.08 (s, 1H). LC-MS: m/z 317.4 $(M + H)^+$. |
| 38 | 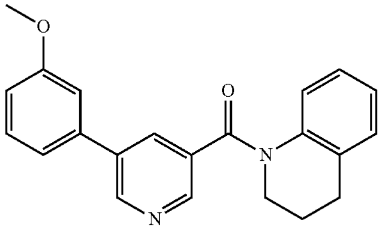 Starting materials: 5-(3-Methoxyphenyl)nicotinic acid and 1,2,3,4-Tetrahydroquinoline | Conditions: Ex. 10, purification b), $^1$H NMR (400 MHz, Chloroform-d) δ: 2.10 (quin, 2H), 2.87 (t, 2H), 3.83 (s, 3H), 3.97 (t, 2H), 6.68 (br s, 1H), 6.86-7.08 (m, 5H), 7.21 (d, 1H), 7.35 (t, 1H), 7.81 (t, 1H), 8.53 (d, 1H), 8.78 (d, 1H). LC-MS: m/z 346.1 $(M + H)^+$. |
| 39 | 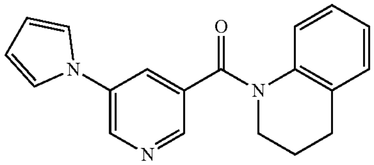 Starting materials: 5-(1H-Pyrrol-1-yl)nicotinic acid and 1,2,3,4-Tetrahydroquinoline | Conditions: Ex. 10, purification b), $^1$H NMR ($DMSO-d_6$, 600 MHz) δ: 8.90 (d, 1H), 8.28 (br s, 1H), 7.98 (br s, 1H), 7.41 (br s, 2H), 7.24 (d, 1H), 7.04 (t, 1H), 6.93 (br t, 2H), 6.31 (t, 2H), 3.80 (t, 2H), 2.85 (t, 2H), 2.07 (s, 1H), 1.99 (quin, 2H). LC-MS: m/z 303.1 $(M + H)^+$. |

-continued

| No | Structure and starting material | Reaction conditions, purification method, $^1$H NMR/LC-MS |
|---|---|---|
| 40 | 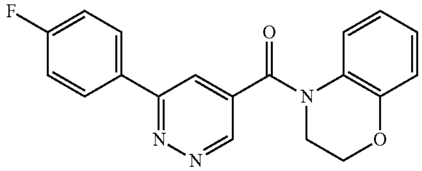 Starting materials: 6-(4-Fluorophenyl)pyridazine-4-carboxylic acid and 2,3-Dihydro-1,4-benzoxazine | Conditions: Ex. 10, purification b), $^1$H NMR (DMSO-$d_6$, 600 MHz) δ: 9.2-9.4 (m, 1H), 8.1-8.5 (m, 3H), 7.3-7.5 (m, 3H), 7.0-7.1 (m, 1H), 6.9-7.0 (m, 2H), 4.2-4.5 (m, 2H), 3.8-4.0 (m, 2H). LC-MS: m/z 336.0 $(M + H)^+$. |
| 41 | 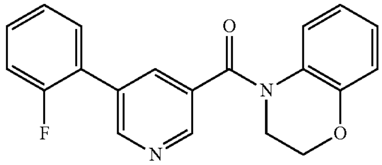 Starting materials: (5-Bromopyridin-3-yl)(2,3-dihydro-4H-benzo[b][1,4]oxazin-4-yl)methanone and 2-Fluorophenylboronic acid | Conditions: Ex. 1, purification b), $^1$H NMR (DMSO-$d_6$, 600 MHz) δ: 8.86 (s, 1H), 8.75 (s, 1H), 8.11 (br s, 1H), 7.59 (br t, 1H), 7.5-7.6 (m, 1H), 7.3-7.4 (m, 3H), 7.05 (s, 1H), 6.93 (dd, 1H), 6.7-6.8 (m, 1H), 4.37 (br s, 2H), 3.93 (br s, 2H). LC-MS: m/z 335.4 $(M + H)^+$. |
| 42 | 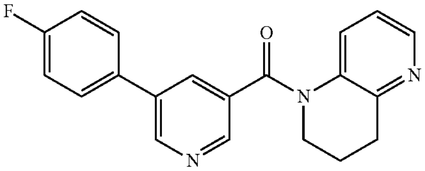 Starting materials: 5-(4-Fluorophenyl)nicotinic acid and 1,2,3,4-Tetrahydro-[1,5]naphthyridine | Conditions: Ex. 10, purification b), $^1$H NMR (DMSO-$d_6$, 600 MHz) δ: 8.95 (d, 1H), 8.58 (br s, 1H), 8.23 (dd, 1H), 8.12 (br s, 1H), 7.77 (dd, 2H), 7.5-7.7 (m, 1H), 7.3-7.4 (m, 2H), 7.06 (br s, 1H), 3.81 (t, 2H), 2.99 (t, 2H), 2.05 (quin, 2H). LC-MS: m/z 334.4 $(M + H)^+$. |
| 43 | 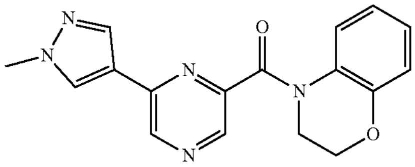 Starting materials: (6-Chloropyrazin-2-yl)(2,3-dihydro-4H-benzo[b][1,4]oxazin-4-yl)methanone and 1-Methyl-4-(4,4,5,5-tetramethyl-1,3,2-dioxaborolan-2-yl)-1H-pyrazole | Conditions: Ex. 1, purification b), $^1$H NMR (DMSO-$d_6$, 600 MHz) δ: 9.07 (br s, 1H), 8.68 (br s, 1H), 8.43 (br s, 1H), 8.0-8.2 (m, 1H), 7.06 (br s, 1H), 6.95 (d, 2H), 4.33 (br s, 2H), 3.96 (br s, 2H), 3.90 (s, 4H). LC-MS: m/z 322.3 $(M + H)^+$. |
| 44 | 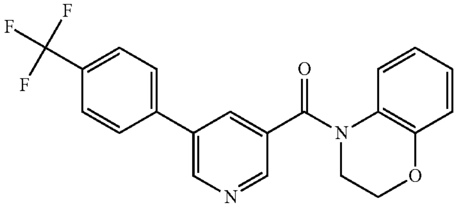 Starting materials: (5-Bromopyridin-3-yl)(2,3-dihydro-4H-benzo[b][1,4]oxazin-4-yl)methanone and 4-(Trifluoromethyl)phenylboronic acid | Conditions: Ex. 1, purification b), $^1$H NMR (DMSO-$d_6$, 600 MHz) δ: 9.0-9.1 (m, 1H), 8.76 (br s, 1H), 8.31 (br s, 1H), 7.98 (br d, 2H), 7.87 (d, 2H), 7.04 (t, 1H), 6.9-7.0 (m, 1H), 6.7-6.8 (m, 1H), 4.37 (br s, 2H), 3.94 (br s, 2H). LC-MS: m/z 385.0 $(M + H)^+$. |
| 45 | 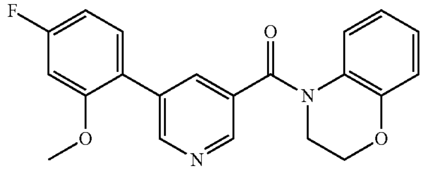 Starting materials: (5-Bromopyridin-3-yl)(2,3-dihydro-4H-benzo[b][1,4]oxazin-4-yl)methanone and 4-Fluoro-2-methoxyphenylboronic acid | Conditions: Ex. 1, purification b), $^1$H NMR (DMSO-$d_6$, 600 MHz) δ: 8.75 (d, 1H), 8.67 (s, 1H), 7.99 (br s, 1H), 7.38 (br t, 1H), 7.08 (dd, 1H), 7.04 (t, 1H), 6.9-7.0 (m, 2H), 6.77 (br s, 1H), 4.36 (br s, 2H), 3.9-4.0 (m, 2H), 3.78 (s, 3H). LC-MS: m/z 365.4 $(M + H)^+$. |

-continued

| No | Structure and starting material | Reaction conditions, purification method, $^{1}H$ NMR/LC-MS |
|---|---|---|
| 46 | 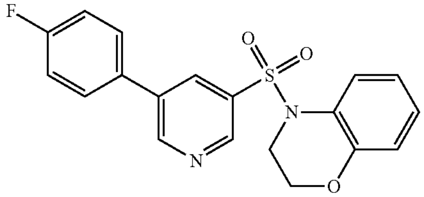 Starting materials: 4-((5-Bromopyridin-3-yl)sulfonyl)-3,4-dihydro-2H-benzo[b][1,4]oxazine and 4-Fluorobenzene boronic acid | Conditions: Ex. 1, purification b), $^{1}H$ NMR (DMSO-$d_6$, 600 MHz) δ: 9.14 (d, 1H), 8.70 (d, 1H), 8.07 (t, 1H), 7.7-7.7 (m, 3H), 7.3-7.4 (m, 2H), 7.2-7.3 (m, 1H), 7.1-7.2 (m, 2H), 3.9-3.9 (m, 2H), 2.41 (t, 2H), 1.65 (quin, 2H). LC-MS: m/z 370.3 $(M + H)^+$. |
| 47 | 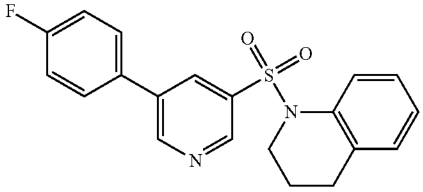 Starting materials: 1-((5-Bromopyridin-3-yl)sulfonyl)-1,2,3,4-tetrahydroquinoline and 4-Fluorobenzene boronic acid | Conditions: Ex. 1, purification b), $^{1}H$ NMR (DMSO-$d_6$, 600 MHz) δ: 9.14 (d, 1H), 8.70 (d, 1H), 8.07 (t, 1H), 7.7-7.7 (m, 3H), 7.36 (t, 2H), 7.2-7.3 (m, 1H), 7.1-7.2 (m, 2H), 3.9-3.9 (m, 2H), 2.41 (t, 2H), 1.65 (quin, 2H). LC-MS: m/z 369.0 $(M + H)^+$. |
| 48 | 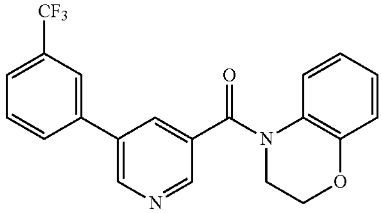 Starting materials: (5-Bromopyridin-3-yl)(2,3-dihydro-4H-benzo[b][1,4]oxazin-4-yl)methanone and 3-(Trifluoromethyl)phenyl boronic acid | Conditions: Ex. 1, purification b), $^{1}H$ NMR (DMSO-$d_6$, 600 MHz) δ: 9.08 (s, 1H), 8.75 (br s, 1H), 8.33 (br s, 1H), 8.07 (br d, 2H), 7.82 (d, 1H), 7.7-7.8 (m, 1H), 7.04 (t, 1H), 6.94 (dd, 1H), 6.7-6.8 (m, 2H), 4.37 (br s, 2H), 3.94 (br s, 2H). LC-MS: m/z 385.4 $(M + H)^+$. |
| 49 | 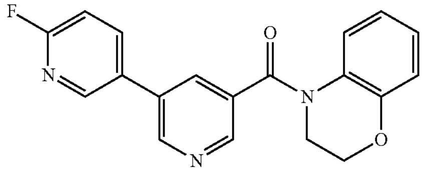 Starting materials: (5-Bromopyridin-3-yl)(2,3-dihydro-4H-benzo[b][1,4]oxazin-4-yl)methanone and 2-Fluoro-5-(4,4,5,5-tetramethyl-1,3,2-dioxaborolan-2-yl)pyridine | Conditions: Ex. 1, purification b), $^{1}H$ NMR (Chloroform-d, 400 MHz) δ: 8.8-8.9 (m, 1H), 8.7-8.8 (m, 1H), 8.32 (br s, 1H), 7.95 (s, 1H), 7.6-7.7 (m, 2H), 6.9-7.2 (m, 3H), 6.68 (br s, 1H), 4.46 (br t, 2H), 4.0-4.2 (m, 2H). LC-MS: m/z 336.0 $(M + H)^+$. |
| 50 | 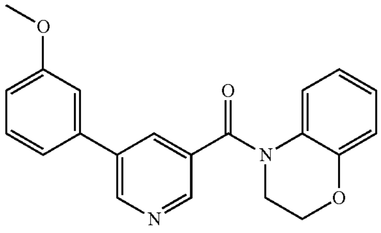 Starting materials: 5-(3-Methoxyphenyl)nicotinic acid and 2,3-Dihydro-1,4-benzoxazin | Conditions: Ex. 10, purification b), $^{1}H$ NMR (DMSO-$d_6$, 600 MHz) δ: 9.0-9.0 (m, 1H), 8.70 (s, 1H), 8.19 (br s, 1H), 7.42 (t, 1H), 7.2-7.3 (m, 2H), 6.9-7.1 (m, 4H), 6.6-6.8 (m, 1H), 4.38 (br s, 2H), 3.94 (br s, 2H), 3.83 (s, 3H). LC-MS: m/z 347.4 $(M + H)^+$. |

-continued

| No | Structure and starting material | Reaction conditions, purification method, $^1$H NMR/LC-MS |
|---|---|---|
| 51 | 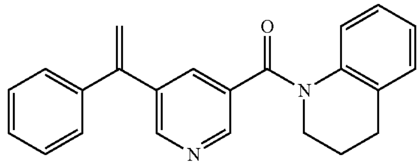 Starting materials: 5-(1-Phenylvinyl)nicotinic acid and 1,2,3,4-Tetrahydroquinoline | Conditions: Ex. 10, purification b), $^1$H NMR (Chloroform-d, 400 MHz) δ: 8.55 (dd, 2H), 7.52 (t, 1H), 7.0-7.4 (m, 7H), 6.9-7.0 (m, 1H), 6.64 (br s, 1H), 5.53 (d, 1H), 5.3-5.4 (m, 1H), 3.92 (t, 2H), 2.80 (t, 2H), 2.0-2.1 (m, 2H). LC-MS: m/z 342.1 $(M + H)^+$. |
| 52 | 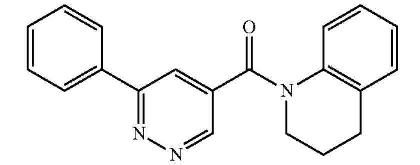 Starting materials: 6-Phenylpyridazine-4-carboxylic acid and 1,2,3,4-Tetrahydroquinoline | Conditions: Ex. 10, purification b), $^1$H NMR (DMSO-$d_6$, 600 MHz) δ: 8.0-8.2 (m, 5H), 7.5-7.6 (m, 6H), 7.27 (d, 2H), 7.08 (br t, 2H), 6.8-7.0 (m, 2H), 3.83 (br s, 4H), 2.89 (t, 4H), 2.08 (s, 1H), 2.02 (br s, 4H). LC-MS: m/z 316.3 $(M + H)^+$. |
| 53 | 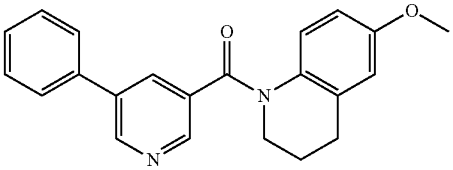 Starting materials: 5-Phenylnicotinic acid and 1,2,3,4-Tetrahydro-6-methoxyquinoline | Conditions: Ex. 10, purification b), $^1$H NMR (Chloroform-d, 400 MHz) δ: 8.75 (d, 1H), 8.58 (d, 1H), 7.81 (t, 1H), 7.3-7.4 (m, 2H), 7.0-7.2 (m, 3H), 6.73 (d, 1H), 6.48 (br s, 1H), 6.3-6.4 (m, 1H), 4.09 (t, 2H), 3.54 (t, 2H), 3.03 (s, 3H). LC-MS: m/z 345.1 $(M + H)^+$. |
| 54 | 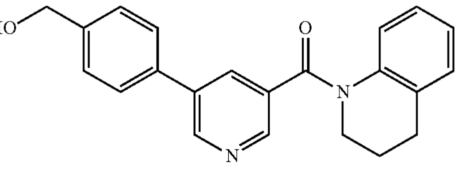 Starting materials: (5-Bromopyridin-3-yl)(3,4-dihydroquinolin-1(2H)-yl)methanone and 4-(Hydroxymethyl)benzeneboronic acid | Conditions: Ex. 1, purification b), $^1$H NMR (DMSO-$d_6$, 600 MHz) δ: 8.87 (d, 1H), 8.44 (br s, 1H), 7.95 (br s, 1H), 7.5-7.6 (m, 2H), 7.42 (d, 2H), 7.25 (d, 1H), 7.04 (t, 1H), 6.93 (br t, 2H), 4.54 (s, 2H), 3.82 (t, 2H), 2.85 (t, 2H), 2.00 (quin, 2H). LC-MS: m/z 345.1 $(M + H)^+$. |
| 55 | 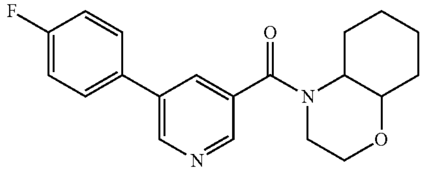 Starting materials: 5-(4-Fluorophenyl)nicotinic acid and Octahydro-2H-benzo[b][1,4]oxazine | Conditions: Ex. 10, purification b), $^1$H NMR (DMSO-$d_6$, 600 MHz) δ: 8.96 (d, 1H), 8.61 (d, 1H), 8.10 (t, 1H), 7.85 (t, 2H), 7.36 (t, 2H), 3.7-3.8 (m, 3H), 3.66 (dt, 1H), 3.5-3.5 (m, 1H), 3.3-3.4 (m, 1H), 2.3-2.4 (m, 1H), 1.9-1.9 (m, 1H), 1.6-1.7 (m, 2H), 1.4-1.5 (m, 1H), 1.2-1.4 (m, 3H). |
| 56 | 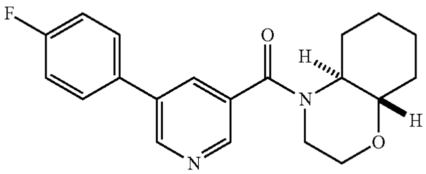 Starting materials: (5-(4-Fluorophenyl)pyridin-3-yl)(octahydro-4H-benzo[b][1,4]oxazin-4-yl)methanone | Conditions: purification d), $^1$H NMR (600 MHz, DMSO-$d_6$) δ: 1.11 (t, 1 H), 1.17-1.36 (m, 5H), 1.43-1.50 (m, 1H), 1.62-1.73 (m, 2H), 1.85-1.92 (m, 1H), 2.33-2.38 (m, 1H), 3.34-3.40 (m, 1H), 3.43-3.56 (m, 2H), 3.62-3.69 (m, 1H), 3.71-3.84 (m, 4H), 7.35 (t, 2H), 7.85 (t, 2H), 8.09 (t, 1H), 8.60 (d, 1H), 8.96 (d, 1H). |

-continued

| No | Structure and starting material | Reaction conditions, purification method, $^1H$ NMR/LC-MS |
|---|---|---|
| 57 | 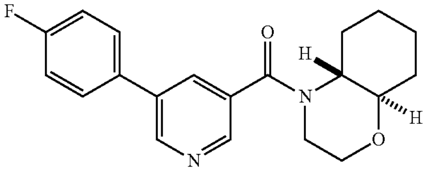 Starting materials: (5-(4-Fluorophenyl)pyridin-3-yl)(octahydro-4H-benzo[b][1,4]oxazin-4-yl)methanone | Conditions: purification d), $^1H$ NMR (600 MHz, DMSO-$d_6$) δ: 1.21-1.36 (m, 3H), 1.42-1.51 (m, 1H), 1.63-1.72 (m, 2H), 1.86-1.92 (m, 1H), 2.33-2.38 (m, 1H), 3.34-3.40 (m, 1H), 3.45-3.53 (m, 1H), 3.66 (td, 1H), 3.72-3.84 (m, 3H), 7.35 (t, 2H), 7.85 (t, 2H), 8.09 (t, 1H), 8.60 (d, 1H), 8.96 (d, 1H). |
| 58 | 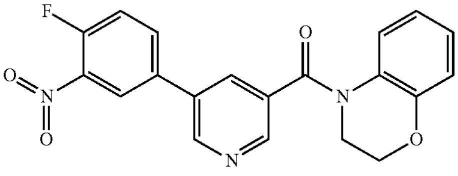 Starting materials: (5-Bromopyridin-3-yl)(2,3-dihydro-4H-benzo[b][1,4]oxazin-4-yl)methanone and 4-Fluoro-3-nitrophenylboronic acid | Conditions: Ex. 1, purification b), $^1H$ NMR (DMSO-$d_6$, 600 MHz) δ: 9.08 (s, 1H), 8.75 (br s, 1H), 8.50 (br d, 1H), 8.35 (br s, 1H), 8.2-8.3 (m, 1H), 7.76 (dd, 1H), 7.04 (br t, 1H), 6.9-7.0 (m, 1H), 6.77 (br s, 2H), 4.37 (br s, 2H), 3.93 (br s, 2H). LC-MS: m/z 380.0 $(M + H)^+$. |
| 59 | 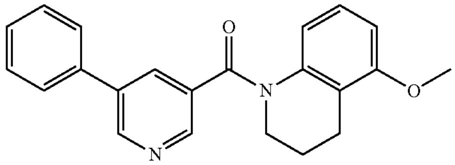 Starting materials: 5-Phenylnicotinic acid and 5-Methoxy-1,2,3,4-tetrahydroquinoline | Conditions: Ex. 10, purification b), $^1H$ NMR (Chloroform-d, 400 MHz) δ: 8.80 (d, 1H), 8.5-8.5 (m, 1H), 7.92 (t, 1H), 7.4-7.5 (m, 6H), 6.88 (t, 1H), 6.6-6.6 (m, 1H), 3.9-4.0 (m, 2H), 3.85 (s, 3H), 2.83 (t, 2H), 2.0-2.1 (m, 2H). LC-MS: m/z 345.1 $(M + H)^+$. |
| 60 | 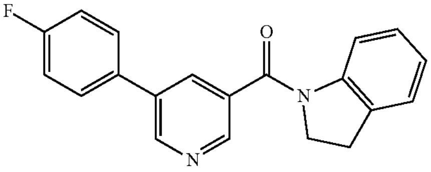 Starting materials: 5-(4-Fluorophenyl)nicotinic acid and indoline | Conditions: Ex. 10, purification b), $^1H$ NMR (DMSO-$d_6$, 600 MHz) δ: 9.02 (s, 1H), 8.78 (br s, 1H), 8.32 (br s, 1H), 8.14 (br s, 1H), 7.87 (br dd, 2H), 7.37 (t, 2H), 7.30 (d, 1H), 7.24 (br s, 1H), 7.08 (br s, 1H), 4.09 (br t, 2H), 3.11 (t, 2H). LC-MS: m/z 320.1 $(M + H)^+$. |
| 61 | 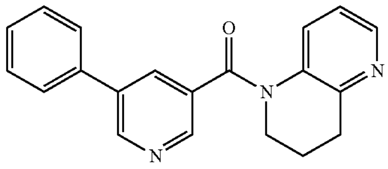 Starting materials: 5-Phenylnicotinic acid and 1,2,3,4-Tetrahydro-[1,5]-naphthyridine | Conditions: Ex. 10, purification b), $^1H$ NMR (DMSO-$d_6$, 600 MHz) δ: 8.96 (d, 1H), 8.59 (s, 1H), 8.24 (br s, 1H), 8.13 (br d, 1H), 7.70 (br d, 2H), 7.51 (t, 2H), 7.4-7.5 (m, 1H), 7.08 (br s, 1H), 3.82 (t, 2H), 2.99 (t, 2H), 2.05 (quin, 2H), 1.5-1.6 (m, 1H), 0.9-1.0 (m, 1H). LC-MS: m/z 316.1 $(M + H)^+$. |
| 62 | 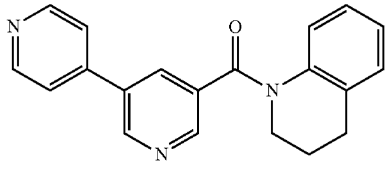 Starting materials: [3,4'-Bipyridine]-5-carboxylic acid and 1,2,3,4-Tetrahydroquinoline | Conditions: Ex. 10, purification b), $^1H$ NMR (DMSO-$d_6$, 600 MHz) δ: 9.01 (d, 1H), 8.67 (d, 2H), 8.5-8.6 (m, 1H), 8.15 (br s, 1H), 7.70 (br d, 2H), 7.1-7.3 (m, 1H), 7.04 (t, 1H), 6.92 (br t, 1H), 6.86 (br s, 1H), 3.82 (t, 2H), 2.86 (t, 2H), 2.0-2.0 (m, 2H). LC-MS: m/z 316.1 $(M + H)^+$. |

-continued

| No | Structure and starting material | Reaction conditions, purification method, $^1$H NMR/LC-MS |
|---|---|---|
| 63 | 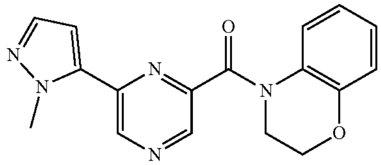 Starting materials: (6-Chloropyrazin-2-yl)(2,3-dihydro-4H-benzo[b][1,4]oxazin-4-yl)methanone and 1-Methyl-5-(4,4,5,5-tetramethyl[1,3,2]dioxaborolan-2-yl)-1H-pyrazole | Conditions: Ex. 1, purification b), $^1$H NMR (Chloroform-d, 400 MHz) δ: 8.94 (s, 2H), 7.4-7.7 (m, 2H), 6.9-7.1 (m, 2H), 6.5-6.8 (m, 2H), 4.4-4.6 (m, 2H), 4.14 (br s, 2H), 3.3-3.8 (m, 3H). LC-MS: m/z 322.0 (M + H)$^+$. |
| 64 | 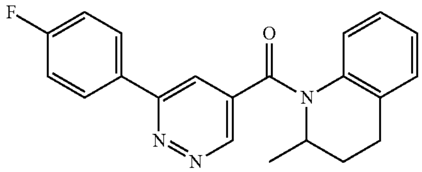 Starting materials: 6-(4-Fluorophenyl)pyridazine-4-carbonyl chloride and 2-Methyl-1,2,3,4-tetrahydroquinoline | Conditions: Ex. 11, purification b), $^1$H NMR (Chloroform-d, 400 MHz) δ: 8.73 (br s, 1H), 7.9-8.0 (m, 2H), 7.73 (d, 1H), 7.1-7.3 (m, 4H), 6.93 (br t, 1H), 6.52 (br s, 1H), 4.88 (br s, 1H), 2.7-2.9 (m, 2H), 2.5-2.7 (m, 2H), 1.2-1.6 (m, 4H). LC-MS: m/z 348.1 (M + H)$^+$. |
| 65 | 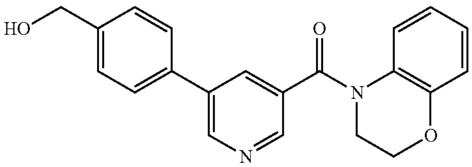 Starting materials: (5-Bromopyridin-3-yl)(2,3-dihydro-4H-benzo[b][1,4]oxazin-4-yl)methanone and 4-(Hydroxymethyl)benzene boronic acid | Conditions: Ex. 1, purification b), $^1$H NMR (DMSO-d$_6$, 600 MHz) δ: 8.99 (d, 1H), 8.68 (s, 1H), 8.19 (br s, 1H), 7.69 (br d, 2H), 7.44 (d, 3H), 7.03 (t, 1H), 6.94 (dd, 1H), 6.6-6.8 (m, 1H), 5.27 (t, 1H), 4.56 (d, 2H), 4.37 (br s, 2H), 3.94 (br s, 2H). LC-MS: m/z 347.1 (M + H)$^+$. |
| 66 | 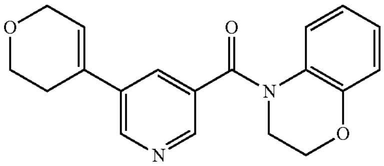 Starting materials: (5-Bromopyridin-3-yl)(2,3-dihydro-4H-benzo[b][1,4]oxazin-4-yl)methanone and 3,6-Dihydro-2H-pyran-4-boronic acid pinacol ester | Conditions: Ex. 1, purification b), $^1$H NMR (DMSO-d$_6$, 600 MHz) δ: 8.78 (d, 1H), 8.58 (br s, 1H), 7.97 (br s, 1H), 7.0-7.1 (m, 1H), 6.93 (dd, 1H), 6.7-6.8 (m, 1H), 6.44 (br s, 1H), 5.6-5.8 (m, 1H), 4.35 (br s, 2H), 4.23 (q, 2H), 3.89 (br s, 2H), 3.82 (t, 2H), 2.45 (br s, 2H). LC-MS: m/z 324.4 (M + H)$^+$. |
| 67 | 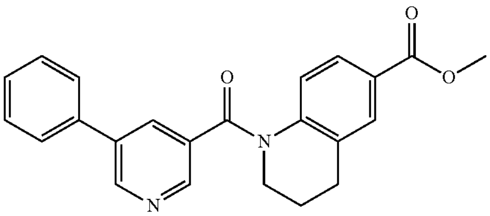 Starting materials: 5-Phenylnicotinic acid and Methyl-1,2,3,4-tetrahydroquinoline-6-carboxylate | Conditions: Ex. 10, purification b), $^1$H NMR (DMSO-d$_6$, 600 MHz) δ: 8.93 (d, 1H), 8.50 (d, 1H), 8.08 (t, 1H), 7.84 (d, 1H), 7.67 (d, 2H), 7.4-7.5 (m, 4H), 7.11 (br d, 1H), 3.8-3.8 (m, 5H), 2.93 (t, 2H), 2.00 (quin, 2H). LC-MS: m/z 373.1 (M + H)$^+$. |
| 68 | 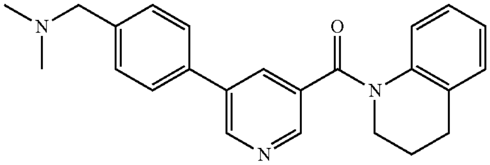 Starting materials: (5-Bromopyridin-3-yl)(3,4-dihydroquinolin-1(2H)-yl)methanone and (4-[(Dimethylamino)methyl]phenyl)boronic acid | Conditions: Ex. 1, purification b), $^1$H NMR (DMSO-d$_6$, 600 MHz) δ: 8.88 (d, 1H), 8.44 (br s, 1H), 7.96 (br s, 1H), 7.5-7.6 (m, 2H), 7.39 (d, 2H), 7.25 (d, 1H), 7.04 (t, 1H), 6.93 (br t, 2H), 3.82 (t, 2H), 3.42 (s, 2H), 2.85 (t, 2H), 2.15 (s, 6H), 2.00 (quin, 2H). LC-MS: m/z 372.2 (M + H)$^+$. |

-continued

| No | Structure and starting material | Reaction conditions, purification method, $^1$H NMR/LC-MS |
|---|---|---|
| 69 | 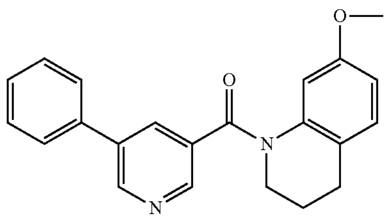 Starting materials: 5-Phenylnicotinic acid and 7-Methoxy-1,2,3,4-tetrahydroquinoline | Conditions: Ex. 10, purification b), $^1$H NMR (Chloroform-d, 400 MHz) δ: 8.91 (br s, 2H), 8.73 (br s, 1H), 7.59 (br s, 2H), 7.09 (br s, 3H), 7.01 (br d, 2H), 6.74 (d, 2H), 6.25 (br s, 2H), 4.14 (br s, 3H), 3.57 (br s, 3H), 3.04 (br s, 4H). LC-MS: m/z 345.1 (M + H)$^+$. |
| 70 | 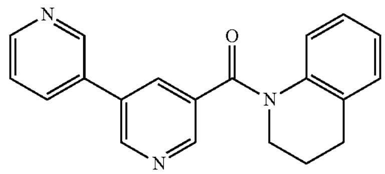 Starting materials: [3,3′-Bipyridine]-5-carboxylic acid and 1,2,3,4-Tetrahydroquinoline | Conditions: Ex. 10, purification b), $^1$H NMR (Chloroform-d, 400 MHz) δ: 8.79 (d, 1H), 8.6-8.7 (m, 2H), 8.58 (d, 1H), 7.82 (t, 1H), 7.75 (d, 1H), 7.3-7.4 (m, 1H), 7.0-7.3 (m, 3H), 6.92 (t, 1H), 6.65 (br s, 1H), 3.99 (t, 2H), 3.7-3.9 (m, 1H), 2.8-2.9 (m, 2H), 2.72 (br t, 1H), 2.23 (s, 1H), 2.11 (quin, 2H), 1.9-2.0 (m, 1H). LC-MS: m/z 317.0 (M + H)$^+$. |
| 71 | 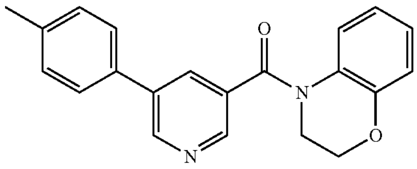 Starting materials: (5-Bromopyridin-3-yl)(2,3-dihydro-4H-benzo[b][1,4]oxazin-4-yl)methanone and 4-Methylbenzene boronic acid | Conditions: Ex. 1, purification b), $^1$H NMR (DMSO-$d_6$, 600 MHz) δ: 8.97 (d, 1H), 8.67 (s, 1H), 8.17 (br s, 1H), 7.63 (br d, 2H), 7.32 (d, 2H), 7.03 (t, 1H), 6.94 (dd, 1H), 6.75 (br s, 1H), 4.37 (br s, 2H), 3.93 (br s, 2H), 2.36 (s, 3H). LC-MS: m/z 331.4 (M + H)$^+$. |
| 72 | 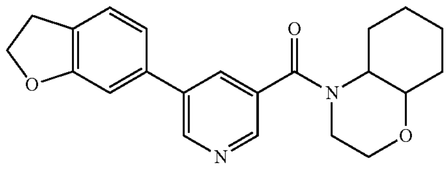 Starting materials: 5-(2,3-Dihydrobenzofuran-6-yl)nicotinic acid and octahydro-2H-benzo[b][1,4]oxazine | Conditions: Ex. 10, purification b) $^1$H NMR (400 MHz, Chloroform-d) δ: 1.29-1.58 (m, 4H), 1.75-1.86 (m, 2H), 1.91-2.10 (m, 1H), 2.47-2.57 (m, 1H), 3.29 (t, 2H), 3.45-3.71 (m, 4H), 3.73-3.95 (m, 4H), 4.64 (t, 2H), 6.89 (d, 1H), 7.31-7.57 (m, 2H), 7.91 (t, 1H), 8.60 (d, 1H), 8.83 (d, 1H). |

Example 12

(2,3-Dihydro-4H-benzo[b][1,4]oxazin-4-yl)(5-(1-methyl-1H-pyrazol-4-yl)-pyridin-3-yl)methanone (Compound 73)

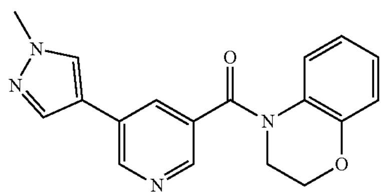 [SMILES: Cn1cc(-c2cncc(C(=O)N3CCOc4ccccc43)c2)cn1]

To a mixture of 1-methyl-4-(4,4,5,5-tetramethyl-1,3,2-dioxaborolan-2-yl)-1H-pyrazole (0.091 g, 0.438 mmol), (5-bromopyridin-3-yl)(2,3-dihydro-4H-benzo[b][1,4]-oxazin-4-yl)methanone (0.112 g, 0.35 mmol) and cesium carbonate (0.319 g, 0.98 mmol) in degassed DME-water (2.5:1, 3.5 ml) under nitrogen atmosphere was added tetrakis (triphenylphosphine)palladium (0.040 g, 0.035 mmol). The mixture was stirred at 90° C. until the reaction was completed. Cooled reaction mixture was diluted with EtOAc and filtered through a short plug of Celite. The filtrate was washed with water and brine, dried and evaporated. Crude was purified by reverse phase flash chromatography to afford 0.083 g of the title compound. $^1$H NMR (400 MHz, $CDCl_3$): δ 8.78 (d, 1H), 8.51 (d, 1H), 7.88 (t, 1H), 7.74 (d, 1H), 7.65 (s, 1H), 7.00-7.06 (m, 1H), 6.94 (dd, 1H), 6.64-6.74 (m, 1H), 6.60-6.70 (m, 1H), 4.37-4.48 (m, 2H), 4.03-4.11 (m, 2H), 3.97 (s, 3H). LC-MS: m/z 321.8 (M+H).

Example 13

(2,3-Dihydro-4H-benzo[b][1,4]oxazin-4-yl)(5-(pyrrolidin-1-yl)pyridin-3-yl)-methanone (Compound 74)

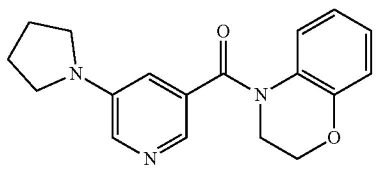 [SMILES: O=C(c1cncc(N2CCCC2)c1)N1CCOc2ccccc21]

A mixture of pyrrolidine (0.067 ml, 0.80 mmol), (5-bromopyridin-3-yl)(2,3-di-hydro-4H-benzo[b][1,4]oxazin-4-yl)methanone (0.128 g, 0.40 mmol), sodium tert-butoxide (0.050 g, 0.52 mmol), tris(dibenzylideneacetone)dipalladium (0.018 g, 0.020 mmol) and rac-2,2'-bis(diphenylphosphino)-1,1'-binaphthyl (0.025 g, 0.10 mmol) in dry toluene (1.5 ml) under nitrogen atmosphere was stirred at 100° C. until the reaction was completed. Cooled mixture was diluted with EtOAc and filtered through a short plug of Celite. The filtrate was evaporated. Crude product was purified by reverse phase flash chromatography to afford 0.046 g of the title compound. $^1$H NMR (400 MHz, $CDCl_3$): δ 8.01 (d, 1H), 7.93 (d, 1H), 7.00-7.17 (br, 1H), 6.97-7.04 (m, 1H), 6.94 (dd, 1H), 6.91 (dd, 1H), 6.66-6.77 (m, 1H), 4.33-4.42 (m, 2H), 3.98-4.07 (m, 2H), 3.24-3.35 (m, 4H), 1.99-2.09 (m, 4H). LC-MS: m/z 310.7 (M+H).

Example 14

2,3-Dihydro-4H-benzo[b][1,4]oxazin-4-yl)(5-(6,6-dimethyl-3-azabicyclo[3.1.0]-hexan-3-yl)pyridin-3-yl)methanone (Compound 75)

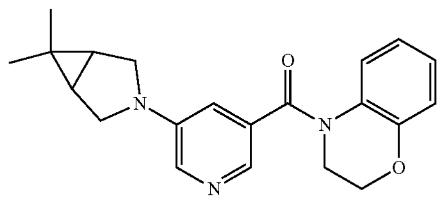 [SMILES: CC1(C)C2CN(c3cncc(C(=O)N4CCOc5ccccc54)c3)CC21]

The compound was prepared according to the procedure of Example 13 starting from 6,6-dimethyl-3-azabicyclo [3.1.0]hexane (0.047 g, 0.42 mmol) and (5-bromopyri-din-3-yl)(2,3-dihydro-4H-benzo[b][1,4]oxazin-4-yl)methanone (0.112 g, 0.35 mmol). Yield 0.028 g. $^1$H NMR (400 MHz, $CDCl_3$): δ 7.95 (d, 1H), 7.92 (d, 1H), 6.58-7.20 (m, 5H), 4.30-4.44 (m, 2H), 3.95-4.08 (m, 2H), 3.37-3.47 (m, 2H), 3.21 (d, 2H), 1.49-1.56 (m, 2H), 1.08 (s, 3H), 0.84 (s, 3H). LC-MS: m/z 350.9 (M+H).

Example 15

(2,3-dihydro-4H-benzo[b][1,4]oxazin-4-yl)(6-(pyrrolidin-1-yl)pyrazin-2-yl)-methanone (Compound 76)

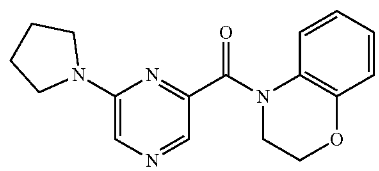 [SMILES: O=C(c1cncc(N2CCCC2)n1)N1CCOc2ccccc21]

A mixture of (6-chloropyrazin-2-yl)(2,3-dihydro-4H-benzo[b][1,4]oxazin-4-yl)-methanone (0.096 g, 0.35 mmol) and pyrrolidine (0.146 ml, 1.75 mmol) in dry DMSO (1.0 ml) was stirred at 90° C. until the reaction was completed. Cooled mixture was diluted with EtOAc, washed with water and brine, dried and evaporated. Crude product was purified by reverse phase flash chromatography to afford the pure compound. $^1$H NMR (400 MHz, $CDCl_3$): δ 8.09 (br s, 1H), 7.89 (s, 1H), 6.96-7.07 (m, 1H), 6.97-6.96 (m, 1H), 6.3-6.87 (m, 2H), 4.24-4.49 (m, 2H), 3.90-4.14 (m, 2H), 3.15-3.63 (m, 4H), 1.85-2.12 (m, 4H). LC-MS: m/z 311.8 (M+H).

The following compounds were prepared according to the procedure of Example 15. The compound number, characterization data, deviating reaction conditions and starting materials are indicated on the table.

| No | Structure and starting material | Reaction conditions, $^1$H NMR/LC-MS |
|---|---|---|
| 77 | 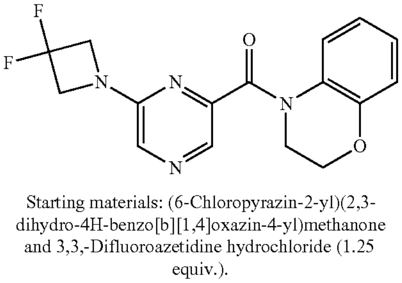 [SMILES: O=C(c1cncc(N2CC(F)(F)C2)n1)N1CCOc2ccccc21] Starting materials: (6-Chloropyrazin-2-yl)(2,3-dihydro-4H-benzo[b][1,4]oxazin-4-yl)methanone and 3,3,-Difluoroazetidine hydrochloride (1.25 equiv.). | Conditions: DIPEA (2.5 equiv.). $^1$H NMR (400 MHz, $CDCl_3$): δ 8.33 (s, 1H), 7.92 (s, 1H), 6.97-7.13 (m, 1H), 6.87-6.97 (m, 1H), 6.0-6.87 (m, 2H), 4.14-4.58 (m, 6H), 3.88-4.14 (m, 2H). LC-MS: m/z 333.6 (M + H). |

-continued

| No | Structure and starting material | Reaction conditions, $^1$H NMR/LC-MS |
|---|---|---|
| 78 | 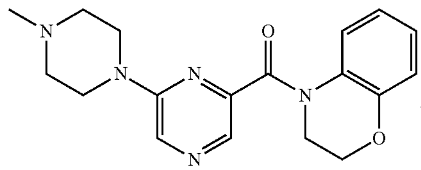 Starting materials: (6-Chloropyrazin-2-yl)(2,3-dihydro-4H-benzo[b][1,4]oxazin-4-yl)methanone and 1-Methylpiperazine (2.0 equiv.). | $^1$H NMR (400 MHz, $CDCl_3$): δ 8.22 (s, 1H), 8.16 (s, 1H), 6.94-7.10 (m, 1H), 6.85-6.94 (m, 1H), 6.02-6.85 (m, 2H), 4.24-4.54 (m, 2H), 3.90-4.18 (m, 2H), 3.15-3.76 (m, 4H), 2.35-2.61 (m, 4H), 2.32 (s, 3H). LC-MS: m/z 340.4 (M + H). |

Example 16

1-(3,4-Dihydroquinolin-1(2H)-yl)-2-(5-(4-fluorophenyl)pyridin-3-yl)ethan-1-one (Compound 79)

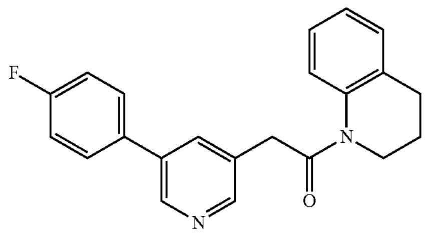 [SMILES: O=C(Cc1cncc(-c2ccc(F)cc2)c1)N1CCCc2ccccc21]

To a mixture of 2-(5-bromopyridin-3-yl)-1-(3,4-dihydroquinolin-1(2H)-yl)ethan-1-one (0.116 g, 0.35 mmol), 4-fluorobenzeneboronic acid (0.059 g, 0.42 mmol) and sodium carbonate (0.104 g, 0.98 mmol) in degassed DME-water (6:1, 1.75 ml) under nitrogen atmosphere was added tetrakis(triphenylphophine)palladium (0.030 g, 0.026 mmol). The mixture was stirred at 90° C. until reaction was completed. Cooled mixture was diluted with EtOAc and filtered through a short plug of Celite. Filtrate was washed with water and brine, dried and evaporated. Crude was purified by reverse phase flash chromatography to afford the pure compound. $^1$H NMR (400 MHz, $CDCl_3$): δ 8.66 (d, 1H), 8.28 (br s, 1H), 7.75 (br s, 1H), 7.47-7.56 (m, 2H), 7.01-7.27 (m, 6H), 3.92 (s, 2H), 3.82 (t, 2H), 2.52-2.71 (m, 2H), 1.93 (quint, 2H). LC-MS: m/z 347.9 (M+H).

The following compounds were prepared according to the procedure of Example 16. The compound number, characterization data and starting materials are indicated on the table.

| No | Structure and starting material | $^1$H NMR/LC-MS |
|---|---|---|
| 80 | 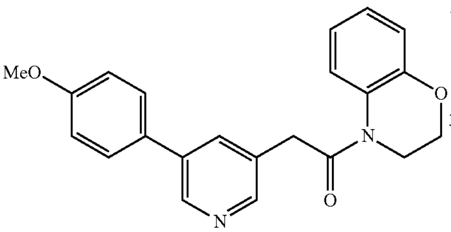 Starting material: 2-(5-Bromopyridin-3-yl)-1-(2,3-dihydro-4H-benzo[b][1,4]oxazin-4-yl)ethan-1-one | $^1$H NMR (400 MHz, $CDCl_3$): δ 8.71 (s, 1H), 8.36 (s, 1H), 7.77 (s, 1H), 7.44-7.57 (m, 2H), 7.06-7.25 (m, 2H), 6.97-7.04 (m, 2H), 6.86-6.97 (m, 2H), 4.19-4.34 (m, 2H), 3.91-4.10 (m, 4H), 3.85 (s, 3H). LC-MS: m/z 361.8 (M + H). |
| 81 | 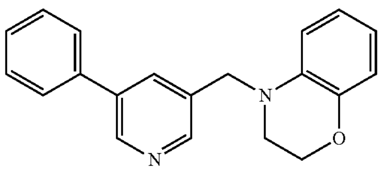 Starting material: 4-((5-Bromopyridin-3-yl)methyl)-3,4-dihydro-2H-benzo[b][1,4]oxazine | $^1$H NMR (400 MHz, $CDCl_3$): δ 8.76 (d, 1H), 8.55 (d, 1H), 7.79-7.83 (m, 1H), 7.52-7.57 (m, 2H), 7.43-7.50 (m, 2H), 7.37-7.43 (m, 1H), 6.77-6.86 (m, 2H), 6.65-6.72 (m, 2H), 4.51 (s, 2H), 4.27-4.33 (m, 2H), 3.37-3.42 (m, 2H). LC-MS: m/z 303.8 (M + H). |

Example 17

(3,4-Dihydroquinolin-1(2H)-yl)(5-(4-methyl-1H-imidazol-1-yl)pyridin-3-yl)-methanone (Compound 82)

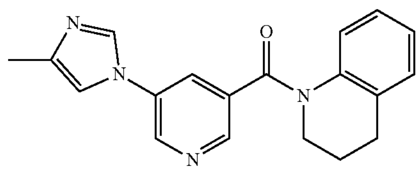 [SMILES: Cc1cn(-c2cncc(C(=O)N3CCCc4ccccc43)c2)cn1]

A mixture of ethyl 5-(4-methyl-1H-imidazol-1-yl)nicotinate (0.080 g, 0.346 mmol), 1,2,3,4-tetrahydroquinoline (0.043 ml, 0.346 mmol) and bis(trimethylaluminum)-1,4-diazabicyclo[2.2.2]octane adduct (0.071 g, 0.277 mmol) in dry toluene (0.5 ml) was stirred at 120° C. until the reaction was completed. Cooled mixture was quenched with aqueous 2 M HCl and then extracted with DCM. Organic phase was dried and evaporated. Crude was purified by reverse phase flash chromatography to afford the pure compound. $^1$H NMR (600 MHz, $d_6$-DMSO): δ 8.91 (d, 1H9, 8.35 (s, 1H), 8.19 (s, 1H), 8.06 (s, 1H), 7.50 (s, 1H), 7.24 (d, 1H), 7.04 (t, 1H), 6.65-7.00 (m, 2H), 3.80 (t, 2H), 2.85 (t, 2H), 2.16 (s, 3H), 1.99 (quint, 2H). LC-MS: m/z 319.7 (M+H).

The following compounds were prepared according to the procedure of Example 17. The compound number, characterization data and starting materials are indicated on the table.

| No | Structure and starting material | $^1$H NMR/LC-MS |
|---|---|---|
| 83 | 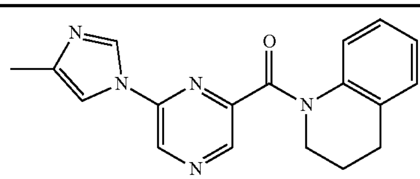 Starting material: Methyl 6-(4-methyl-1H-imidazol-1-yl)pyrazine-2-carboxylate | $^1$H NMR (400 MHz, $CDCl_3$): δ 8.80 (s, 1H), 8.63 (s, 1H), 7.47-7.77 (m, 1H), 7.21-7.27 (m, 1H), 7.06 (t, 1H), 6.74-7.04 (m, 2H), 6.17-6.55 (m, 1H), 3.87-4.08 (m, 2H), 2.88 (t, 2H), 2.25 (s, 3H), 2.12 (quint, 2H). LC-MS: m/z 320.7 (M + H). |
| 84 | 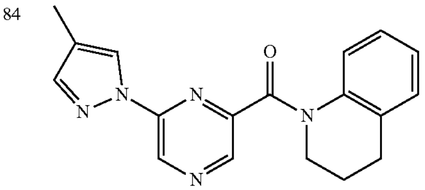 Starting material: Methyl 6-(4-methyl-1H-pyrazol-1-yl)pyrazine-2-carboxylate | $^1$H NMR (400 MHz, $CDCl_3$): δ 9.21 (s, 1H), 8.62 (s, 1H), 7.46-7.78 (m, 2H), 7.18-7.26 (m, 1H), 6.77-7.12 (m, 2H), 6.08-6.68 (m, 1H), 3.88-4.09 (m, 2H), 3.89 (t, 2H), 2.05-2.19 (m, 5H). LC-MS: m/z 320.7 (M + H). |
| 85 | 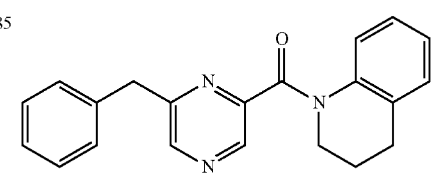 Starting material: Methyl 6-benzylpyrazine-2-carboxylate | $^1$H NMR (400 MHz, $CDCl_3$): δ 8.57 (br s, 1H), 8.38 (s, 1H), 7.13-7.32 (m, 4H), 6.94-7.13 (m, 3H), 6.03-6.94 (m, 2H), 4.03 (s, 2H), 3.76-4.03 (m, 2H9, 2.85 (t, 2H), 1.96-2.17 (m, 2H). |

Example 18

1-(2,3-Dihydro-4H-benzo[b][1,4]oxazin-4-yl)-2-(5-(4-fluorophenyl)pyridin-3-yl)ethan-1-one (Compound 86)

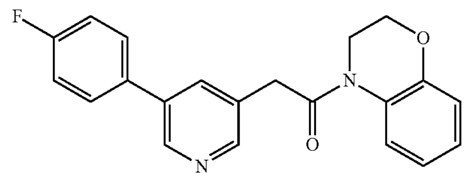 [SMILES: O=C(Cc1cncc(-c2ccc(F)cc2)c1)N1CCOc2ccccc21]

a) 2-(5-(4-Fluorophenyl)pyridin-3-yl)acetic acid

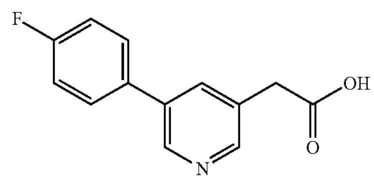 [SMILES: O=C(O)Cc1cncc(-c2ccc(F)cc2)c1]

To a mixture of 5-bromo-3-pyridineacetic acid (0.216 g, 1 mmol), 4-fluorobenzeneboronic acid (0.175 g, 1.25 mmol), cesium carbonate (0.912 g, 2.80 mmol) in degassed DME-water (3:1, 8 ml) under nitrogen atmosphere was added tetrakis(tri-phenylphosphine)palladium (0.116 g, 0.10 mmol). The mixture was stirred at 90° C. until reaction was completed. Cooled mixture was diluted with EtOAc and filtered through a short plug of Celite. Phases were separated and pH of the aqueous phase was adjusted to 6 with aqueous 2 M NaOH solution. Aqueous phase was extracted with EtOAc. Organic phase was dried and evaporated to afford 0.10 g of the title compound. $^1$H NMR (400 MHz, $d_6$-DMSO): δ 12.56 (s, 1H), 8.77 (d, 1H), 8.46 (d, 1H), 7.97 (t, 1H), 7.74-7.81 (m, 2H), 7.31-7.40 (m, 2H), 3.73 (s, 2H).

b) 1-(2,3-Dihydro-4H-benzo[b][1,4]oxazin-4-yl)-2-(5-(4-fluorophenyl)pyridin-3-yl)ethan-1-one (Compound 85)

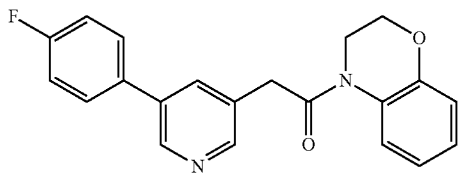 [SMILES: O=C(Cc1cncc(-c2ccc(F)cc2)c1)N1CCOc2ccccc21]

The compound was prepared according to the procedure of Intermediate 19 starting from 2-(5-(4-fluorophenyl)pyridin-3-yl)acetic acid (0.090 g, 0.35 mmol) and 3,4-dihydro-2H-benzo[b][1,4]oxazine (0.052 g, 0.385 mmol). Crude product was purified by reverse phase flash chromatography. Yield: 0.039 g. $^1$H NMR (400 MHz, $CDCl_3$): δ 8.70 d (1H), 8.40 (br s, 1H), 7.78 (br s, 1H), 7.48-7.58 (m, 2H), 7.00-7.24 (m, 4H), 6.87-6.99 (m, 2H), 4.21-4.34 (m, 2H), 3.89-4.11 (m, 4H). LC-MS: m/z 349.9 (M+H).

Example 19

(3,4-Dihydroquinolin-1(2H)-yl)(6-(3,5-dimethyl-1H-pyrazol-1-yl)pyrazin-2-yl)-methanone (Compound 87)

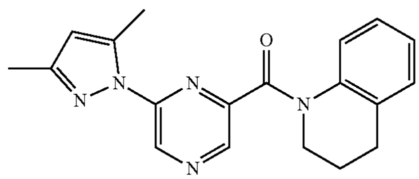 [SMILES: Cc1cc(C)n(-c2cncc(C(=O)N3CCCc4ccccc43)n2)n1]

a) (6-Bromopyrazin-2-yl)(3,4-dihydroquinolin-1(2H)-yl)methanone

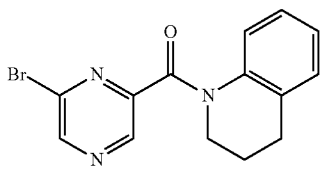

The compound was prepared according to the procedure of Example 17 starting from methyl 6-bromopyrazine-2-carboxylate (0.217 g, 1.00 mmol) and 1,2,3,4-tetrahydroquinoline (0.126 ml, 1.00 mmol). Crude product was purified by flash chromatography to afford 0.080 g of the title compound. $^1$H NMR (400 MHz, $CDCl_3$): δ 8.30-8.88 (m, 2H), 7.15-7.22 (m, 1H), 7.07 (t, 1H), 6.77-7.07 (br, 1H), 6.0-6.75 (br, 1H), 3.76-4.12 (m, 2H), 2.87 (t, 2H), 2.09 (quint., 2H).

b) (3,4-Dihydroquinolin-1(2H)-yl)(6-(3,5-dimethyl-1H-pyrazol-1-yl)pyrazin-2-yl)methanone (Compound 86)

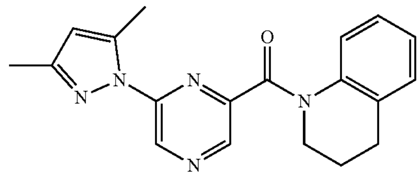 [SMILES: Cc1cc(C)n(-c2cncc(C(=O)N3CCCc4ccccc43)n2)n1]

The compound was prepared according to the procedure of Intermediate 22 starting from (6-bromopyrazin-2-yl)(3,4-dihydroquinolin-1(2H)-yl)methanone (0.080 g, 0.251 mmol) and 3,5-dimethylpyrazole (0.024 g, 0.251 mmol). Crude product was purified by reverse phase flash chromatography to afford 0.012 g of the title compound. $^1$H NMR (400 MHz, $CDCl_3$): δ 9.26 (s, 1H), 8.72 (d, 1H), 7.12-7.18 (m, 1H), 6.99 (t, 1H), 6.76-6.93 (m, 1H), 6.19-6.6 (m, 1H), 5.90 (s, 1H), 3.97 (t, 2H), 2.84 (t, 2H), 2.26 (s, 3H), 2.10 (quint, 2H), 1.98 (br s, 3H). LC-MS: m/z 334.7 (M+H).

Example 20

(3,4-Dihydroquinolin-1(2H)-yl)(5-(4-methyl-1H-pyrazol-1-yl)pyridin-3-yl)-methanone (Compound 88)

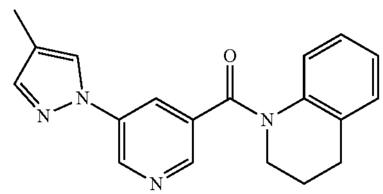 [SMILES: Cc1cnn(-c2cncc(C(=O)N3CCCc4ccccc43)c2)c1]

A mixture of (5-bromopyridin-3-yl)(3,4-dihydroquinolin-1(2H)-yl)-methanone (0.111 g, 0.35 mmol), 4-methylpyrazole (0.035 ml, 0.438 mmol), potassium phosphate (0.097 g, 0.455 mmol), copper iodide (0.013 g, 0.070 mmol) and N,N'-di-methylenediamine (0.015 ml, 0.140 mmol) in dry toluene (1.0 ml) was stirred at 110° C. until reaction was completed. Cooled mixture was diluted with EtOAc and filtered through a short plug of Celite. Filtrate was washed with aqueous $NH_4Cl$—$NH_3$ solution (4:1) and water and brine, dried and evaporated. Crude product was purified by reverse phase flash chromatography to afford 0.016 g of the title compound. $^1$H NMR (400 MHz, $CDCl_3$): δ 8.94 (d, 1H), 8.27 (s, 1H), 8.06 (dd, 1H), 7.63-7.67 (m, 1H), 7.56 (s, 1H), 7.17-7.23 (m, 1H), 7.05 (td, 1H), 6.87-6.94 (m, 1H), 6.60-6.80 (m, 1H), 3.95 (t, 2H), 3.86 (t, 2H), 2.16 (s, 3H), 2.09 (quint, 2H). LC-MS: m/z 319.7 (M+H).

Example 21

1-((5-(4-Fluorophenyl)pyridin-3-yl)methyl)-1,2,3,4-tetrahydroquinoline (Compound 89)

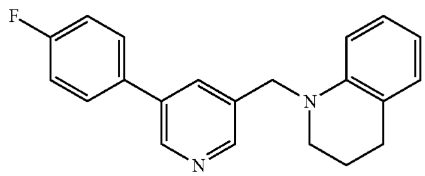 [SMILES: Fc1ccc(-c2cncc(CN3CCCc4ccccc43)c2)cc1]

To a mixture of 1,2,3,4-tetrahydroquinoline (0.050 ml, 0.40 mmol) in 1,2-dichloroethane (1.0 ml) and acetic acid (0.25 ml) was added 5-(4-fluorophenyl)nicotin-aldehyde (0.089 g, 0.44 mmol) dissolved in 1,2-dichloroethane (1.0 ml). The mixture was stirred at RT for 6 h. Sodium triacetoxy borohydride (0.1287 g, 0.88 mmol) was added and the mixture was stirred overnight at RT. The mixture was diluted with DCM and basified with saturated aqueous $NaHCO_3$ solution. Phases were separated and aqueous phase was extracted with DCM. Combined organic phases were dried and evaporated. Crude product was purified by reverse phase flash chromatography to afford the pure compound. $^1$H NMR (400 MHz, $CDCl_3$): δ 8.69 (d, 1H), 8.51-8.54 (m, 1H), 7.70-7.73 (m, 1H), 7.46-7.53 (m, 2H), 7.10-7.18 (m, 2H), 6.97-7.03 (m, 2H), 6.62 (td, 1H), 6.51-6.55 (m, 1H), 4.54 (s, 2H), 3.36-3.42 (m, 2H), 2.83 (t, 2H), 2.00-2.08 (m, 2H). LC-MS: m/z 319.8 (M+H).

The following compounds were prepared according to the procedure of Example 21. The compound number, characterization data and starting materials are indicated on the table.

| No | Structure and starting material | $^1$H NMR/LC-MS |
|---|---|---|
| 90 | 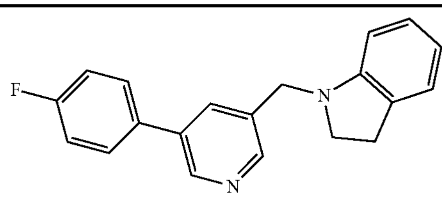 Starting material: 5-(4-Fluorophenyl)-nicotinaldehyde and indoline | $^1$H NMR (400 MHz, $CDCl_3$): δ 8.73 (d, 1H), 8.59 (d, 1H), 7.84-7.88 (m, 1H), 7.51-7.58 (m, 2H), 7.05-7.20 (m, 4H), 6.72 (td, 1H), 6.55 (d, 1H), 4.31 (s, 2H), 3.34 (t, 2H), 3.00 (t, 2H). LC-MS: m/z 305.7 (M + H). |
| 91 | 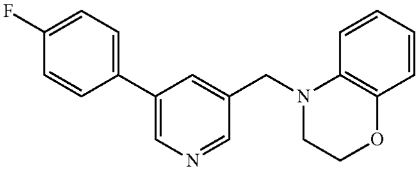 Starting material: 5-(4-Fluorophenyl)-nicotinaldehyde and 3,4-Dihydro-2H-benzo[b][1,4]oxazine | $^1$H NMR (400 MHz, $CDCl_3$): δ 8.72 (d, 1H), 8.55 (d, 1H), 7.73-7.78 (m, 1H), 7.47-7.55 (m, 2H9, 7.12-7.19 (m, 2H), 6.77-6.87 (m, 2H), 6.64-6.72 (m, 2H), 4.51 (s, 2H), 4.28-4.33 (m, 2H), 3.37-3.43 (m, 2H). LC-MS: m/z 321.8 (M + H). |

Abbreviations

DCM—Dichloromethane
DIPEA—N,N-diisopropylethylamine
DME—Dimethoxyethane
DMF—N,N-Dimethylformamide
DMSO—Dimethylsulfoxide dppp—1,3-Bis(diphenylphosphino)propane
HPLC—High-performance liquid chromatography
LC-MS—Liquid chromatography-mass spectrometry
$PdCl_2$(dppf)—[1,1'-Bis(diphenylphosphino)ferrocene]dichloropalladium(II)
$Pd(OAc)_2$—Palladium(II) acetate
$Pd_2(dba)_3$—Tris(dibenzylideneacetone)dipalladium
$PdCl_2(PPh_3)_2$—Bis(triphenylphosphine)palladium(II) dichloride
Q-PHOS—1,2,3,4,5-Pentaphenyl-1'-(di-tert-butylphosphino)ferrocene
RT—Room temperature
STB—Sodium tert-butoxide
STAB—Sodium triacetoxy borohydride
TEA—Triethylamine
$T_3P$—Propylphosphonic anhydride
THF—Tetrahydrofuran
TLC—Thin layer chromatography
TMA—Trimethylamine EXPERIMENTS Experiment 1. CYP11A1 Inhibition The ability of the test compounds to inhibit pregnenolone biosynthesis was measured by enzyme-linked immunosorbent assay (ELISA) detecting pregnenolone (Abnova Pregnenolone ELISA Kit, KA1912). Human adrenocortical carcinoma cell line NCI-H295R that has been shown to express all the key steroidogenic enzymes was used as a enzyme source. To determine the half maximal inhibitory concentration ($IC_{50}$) of the test compounds on CYP11A1 inhibition, the cells were treated for 24 hours with increasing concentrations of the test compound. The final DMSO concentration was 0.4%. Medium samples were diluted 1:6 and pregnenolone amounts determined with ELISA. Manufacturer's recommended protocols were used and pregnenolone (Sigma-Aldrich, P9129) standards were prepared in cell culture medium. Absorbance (A450) was measured with Envision plate reader (PerkinElmer). All the test compounds were studied at 10 concentrations in duplicates.

The compounds of the invention were screened in the above mentioned assay and the $IC_{50}$ values of the compounds are set forth in Table 1 below wherein "A" refers to an $IC_{50}$ value of less than 50 nM, "B" refers to $IC_{50}$ value in range of 51 to 200 nM and "C" refers to $IC_{50}$ value in range of 201 nM to 2500 nM.
TABLE 1
| Group | Compound No. |
|---|---|
| A | 2, 5, 8, 10, 12, 13, 14, 15, 16, 18, 19, 20, 21, 22, 23, 24, 25, 26, 27, 28, 29, 30, 31, 32, 33, 34, 35, 36, 37, 38, 39, 40, 41, 83, 84 and 88. |
| B | 3, 4, 9, 11, 42, 43, 44, 45, 46, 47, 48, 49, 50, 51, 52, 53, 54, 55, 56, 87, 89 and 90. |
| C | 1, 6, 7, 57, 58, 59, 60, 61, 62, 63, 64, 65, 66, 67, 68, 69, 70, 71, 72, 73, 74, 75, 76, 77, 78, 79, 80, 81, 82, 85, 86 and 91. |
The invention claimed is:
1. A compound of formula (I) or a pharmaceutically acceptable salt thereof
(I)
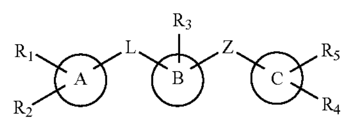
wherein:
B is
(1) (2) (3)
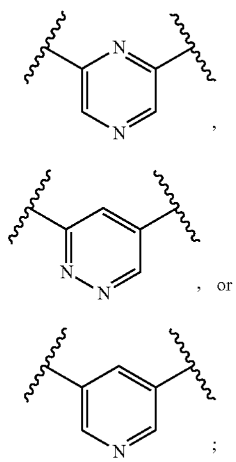
, , or ;
wherein B is selected such that:
i) when B is
(1) (2)
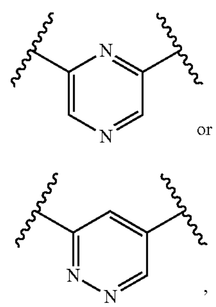
or ,
then
A is;
(1″)
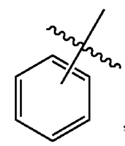
,
(2″)
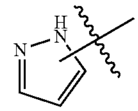
,
(2a)
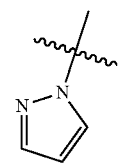
,
(2b)
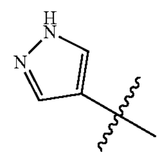
,
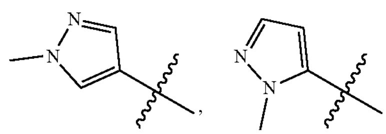
, ,
(3″)
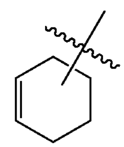
,
(3a)
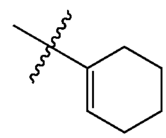
,
(4″)
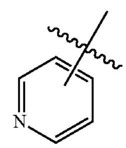
,
(4a)
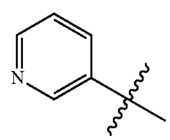
,
(4b)
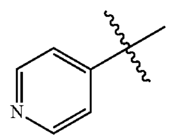
, -continued
(5″)
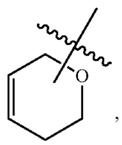
,
(6″)
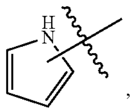
,
(6a)
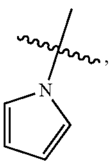
,
(7″)
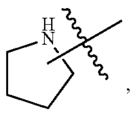
,
(8″)
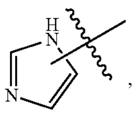
,
(8a)
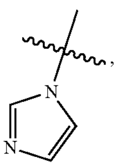
,
(9″)
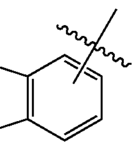
,
(9a)
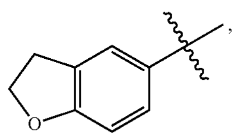
,
(9b)
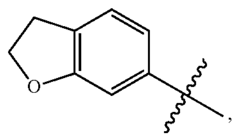
,
(10″)
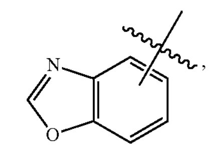
,
(10a)
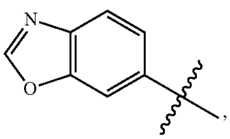
,
-continued
(11″)
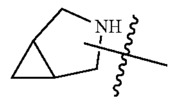
,
(11a)
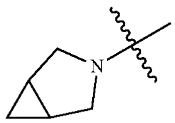
,
(12″)
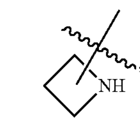
,
(12a)
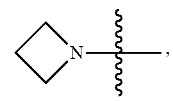
,
(13″)
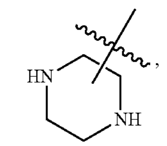
,
(13a)
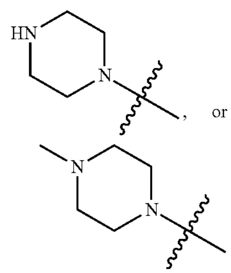
, or ;
C is:
(1′)
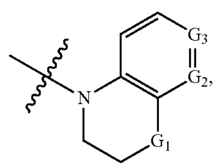
,
(2′)
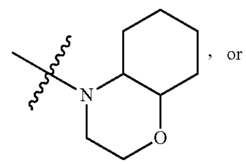
, or
(3′)
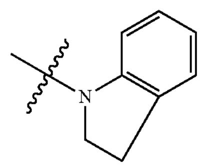
;
$G_1$ is $CH_2$, NH or O;
$G_2$ and $G_3$ are, independently, CH or N;

Z is —C(O)—, —$SO_2$—, —$C_{1-3}$ alkyl- or —$CH_2$—C(O)—;

L is a bond, —$C_{1-7}$ alkyl- or —$C_{1-7}$ alkenyl-;

$R_1$ is hydrogen, $C_{1-7}$ alkyl, $C_{1-7}$ alkoxy, halogen, hydroxy, nitro, halogen $C_{1-7}$ alkyl, hydroxy $C_{1-7}$ alkyl, —O-halogen $C_{1-7}$ alkyl or —X—$NR_6R_7$;

$R_2$ is hydrogen, hydroxy, $C_{1-7}$ alkyl or halogen;

$R_3$ is hydrogen, $C_{1-7}$ alkyl or amino;

$R_4$ is hydrogen, $C_{1-7}$ alkyl, $C_{1-7}$ alkoxy, halogen, hydroxy, hydroxy $C_{1-7}$ alkyl, halogen $C_{1-7}$ alkyl or —C(O)—O—$C_{1-7}$ alkyl;

$R_5$ is hydrogen, halogen, $C_{1-7}$ alkoxy or $C_{1-7}$ alkyl;

X is a bond or $C_{1-7}$ alkyl; and $R_6$ and $R_7$ are, independently, hydrogen or $C_{1-7}$ alkyl; and ii) when B is (3)

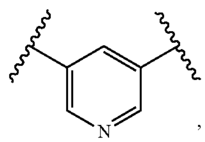, then

A is (1″)

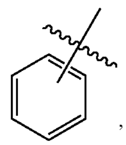, (2″)

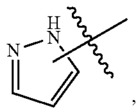, (2a)

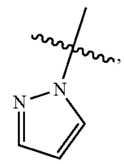, (3″)

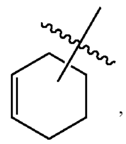, (4″)

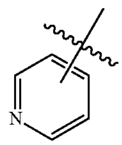, (5″)

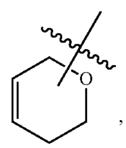,

-continued (6″)

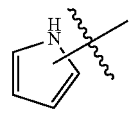, (6a)

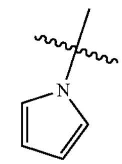, (7″)

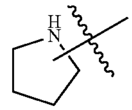, (7a)

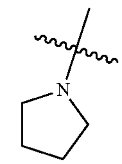, (8″)

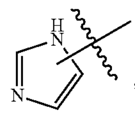, (8a)

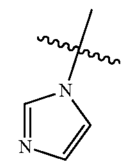, (9″)

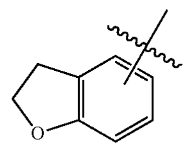, (10″)

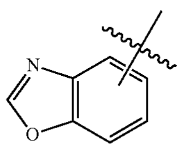, (11a)

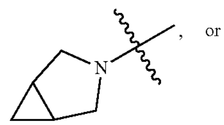, or (11″)

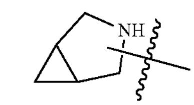;

provided that when C is ring (3'), then A is not ring (2") or ring (7");

C is (1')

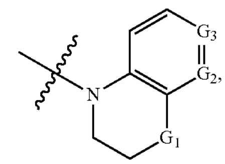

(2')

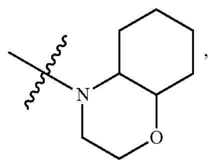

(3')

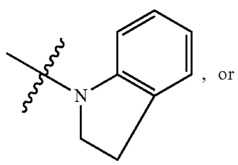

, or (4')

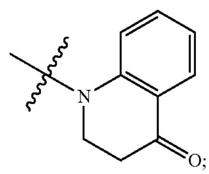

$G_1$ is $CH_2$, NH or O;

$G_2$ and $G_3$ are, independently, CH or N;

Z is —C(O)—, —$SO_2$—, —$C_{1-3}$ alkyl- or —$CH_2$—C(O)—;

L is a bond, —$C_{1-7}$ alkyl- or —$C_{1-7}$ alkenyl-;

$R_1$ is hydrogen, $C_{1-7}$ alkyl, $C_{1-7}$ alkoxy, halogen, hydroxy, halogen $C_{1-7}$ alkyl, hydroxy $C_{1-7}$ alkyl, —O-halogen $C_{1-7}$ alkyl, or —X—$NR_6R_7$, $R_2$ is hydrogen, hydroxy, $C_{1-7}$ alkyl or halogen;

$R_3$ is hydrogen, $C_{1-7}$ alkyl, or amino;

$R_4$ is hydrogen, $C_{1-7}$ alkyl, $C_{1-7}$ alkoxy, halogen, hydroxy $C_{1-7}$ alkyl, halogen $C_{1-7}$ alkyl or —C(O)—O—$C_{1-7}$ alkyl;

$R_5$ is hydrogen, halogen, $C_{1-7}$ alkoxy, or $C_{1-7}$ alkyl;

X is a bond or $C_{1-7}$ alkyl; and $R_6$ and $R_7$ are, independently, hydrogen, or $C_{1-7}$ alkyl;

with the proviso that the compound of formula (I) is not:

(3,4-Dihydro-3-methoxy-1(2H)-quinolinyl)(6-phenyl-4-pyridazinyl)methanone;

(6-Fluoro-3,4-dihydro-4-methyl-1(2H)-quinoxalinyl)(5-phenyl-3-pyridinyl)methanone;

(3,4-Dihydro-1(2H)-quinolinyl)(5-phenyl-3-pyridinyl)methanone;

(5-(2,3-Dihydro-5-benzofuranyl)-3-pyridinyl)(3,4-dihydro-1(2H)-quinolinyl)methanone;

(5-(2,3-Dihydro-5-benzofuranyl)-3-pyridinyl)(7-fluoro-2,3-dihydro-4H-1,4-benzoxazin-4-yl)methanone;

(6,8-Difluoro-3,4-dihydro-1(2H)-quinolinyl)(5-(4-(dimethylamino)phenyl)-3-pyridinyl)methanone;

(3,4-Dihydro-1(2H)-quinolinyl)(5-(1-pyrrolidinyl)-3-pyridinyl)methanone;

(5-(2,3-Dihydro-5-benzofuranyl)-3-pyridinyl)(octahydro-4H-1,4-benzoxazin-4-yl)methanone;

(5-(4-Methoxyphenyl)-3-pyridinyl)(octahydro-4H-1,4-benzoxazin-4-yl)methanone or (2,3-Dihydro-1H-indol-1-yl)(5-phenyl-3-pyridinyl)methanone.

2. The compound according to claim 1, wherein B is (1)

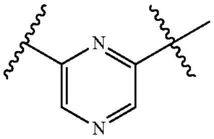

or (3)

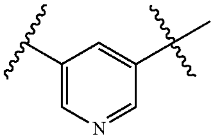

3. The compound according to claim 1, wherein Z is —C(O)—.

4. The compound according to claim 1, wherein L is a bond.

5. The compound according to claim 1, wherein C is (1')

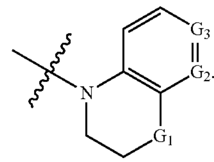

6. The compound according to claim 5, wherein $G_1$ is $CH_2$ or O.

7. The compound according to claim 1, wherein $G_2$ is N and $G_3$ is CH.

8. The compound according to claim 1, wherein $G_2$ is CH and $G_3$ is N.

9. The compound according to claim 1, wherein $R_1$ is hydrogen, $C_{1-7}$ alkyl, $C_{1-7}$ alkoxy, halogen, hydroxy $C_{1-7}$ alkyl, or halogen $C_{1-7}$ alkyl.

10. The compound according to claim 1, wherein $R_2$ is hydrogen, hydroxy, $C_{1-7}$ alkyl, or halogen.

11. The compound according to claim 1, wherein $R_3$ is hydrogen.

12. The compound according to claim 1, wherein $R_4$ is hydrogen, $C_{1-7}$ alkyl, halogen, or —C(O)—O—$C_{1-7}$ alkyl.

13. The compound according to claim 1, wherein $R_5$ is hydrogen.

14. The compound according to claim 1, wherein when B is (3)

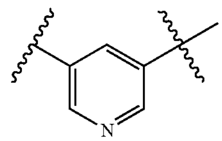

then A is:
(1″)
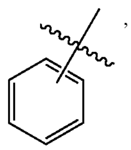
,
(2a)
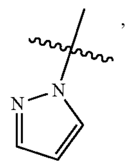
,
(2b)
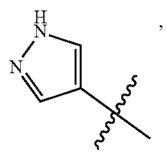
,
(3a)
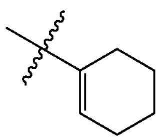
,
(4a)
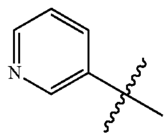
,
(4b)
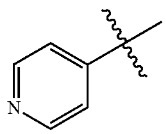
,
(5″)
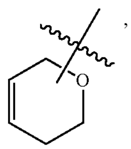
,
(6a)
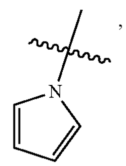
,
(7a)
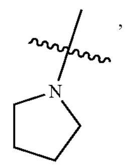
,
-continued
(8a)
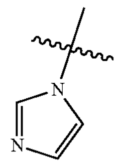
,
(9a)
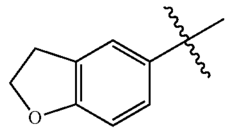
,
(9b)
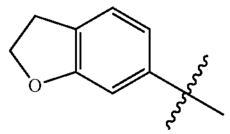
,
(10a)
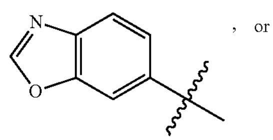
, or
(11a)
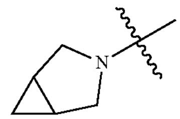
.
15. The compound according to claim 1 wherein when B is
(1)
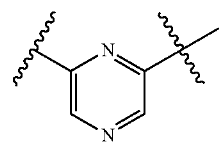
or
(2)
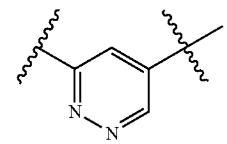
,
A is:
(1″)
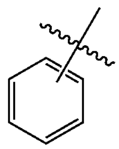
,
(2a)
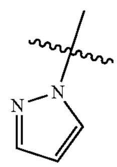
, -continued (2b)

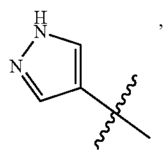

, (3a)

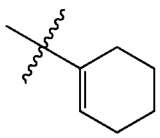

, (4a)

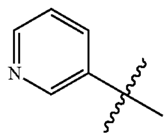

, (4b)

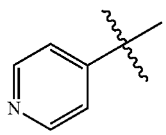

, (5″)

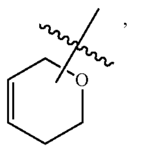

, (6a)

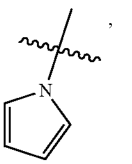

, (8a)

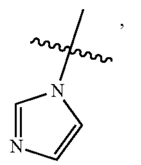

, (9a)

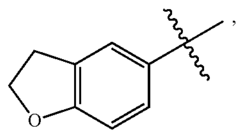

, (9b)

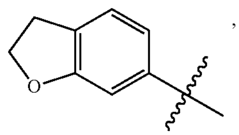

, (10a)

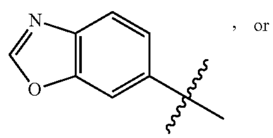

, or

-continued (11a)

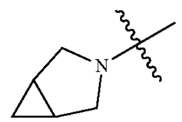

.

(12a)

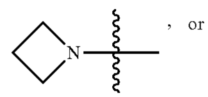

, or (13a)

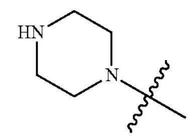

.

16. The compound according to claim 1, wherein the compound is represented by formula (IA) or a pharmaceutically acceptable salt thereof, (IA)

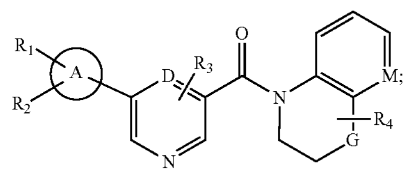

wherein:

D is N or CH;

G is $CH_2$, NH or O;

M is CH or N;

$R_1$ is hydrogen, $C_{1-7}$ alkyl, $C_{1-7}$ alkoxy, or halogen;

$R_2$ is hydrogen or halogen;

$R_3$ is hydrogen or $C_{1-7}$ alkyl;

$R_4$ is hydrogen, $C_{1-7}$ alkyl, halogen, or —C(O)—O—$C_{1-7}$ alkyl;

A is (1″)

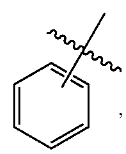

, (2a)

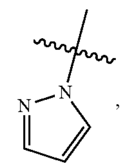

, (2b)

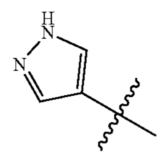

-continued (3a)

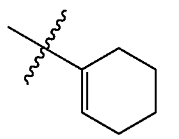

, (6a)

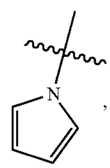

, (8a)

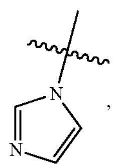

, (9b)

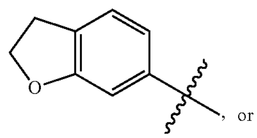

, or (10a)

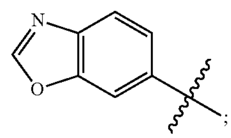

;

with the proviso that compound of formula (I) is not:

(3,4-Dihydro-1(2H)-quinolinyl)(5-phenyl-3-pyridinyl) methanone;

(5-(2,3-Dihydro-5-benzofuranyl)-3-pyridinyl)(3,4-dihydro-1(2H)-quinolinyl)methanone or (5-(2,3-Dihydro-5-benzofuranyl)-3-pyridinyl)(7-fluoro-2,3-dihydro-4H-1,4-benzoxazin-4-yl)methanone.

17. The compound according to claim 16, wherein A is (1″)

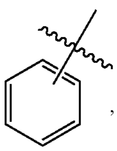

, (2a)

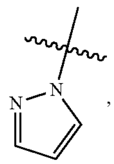

, (3a)

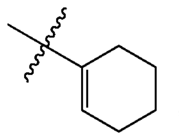

,

-continued (9b)

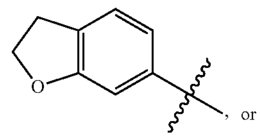

, or (10a)

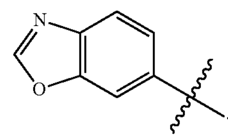

.

18. The compound according to claim 1, wherein the compound is:

(2,3-Dihydro-4H-benzo[b][1,4]oxazin-4-yl)(5-(3-(trifluoromethoxy)phenyl)pyridin-3-yl)methanone;

(7-Fluoro-2,3-dihydro-4H-benzo[b][1,4]oxazin-4-yl)(5-(4-fluorophenyl)pyridin-3-yl)methanone;

(2,3-Dihydro-4H-benzo[b][1,4]oxazin-4-yl)(4-methyl-5-phenylpyridin-3-yl)methanone;

(3,4-Dihydroquinolin-1(2H)-yl)(4-methyl-5-phenylpyridin-3-yl)methanone;

(2,3-Dihydro-4H-benzo[b][1,4]oxazin-4-yl)(5-(4-fluorophenyl)-4-methylpyridin-3-yl)methanone;

(4-Amino-5-phenylpyridin-3-yl)(3,4-dihydroquinolin-1(2H)-yl)methanone;

(2,3-Dihydro-4H-benzo[b][1,4]oxazin-4-yl)(5-(4-fluorophenyl)pyridazin-3-yl)-methanone;

(6-(Benzo[d]oxazol-6-yl)pyrazin-2-yl)(2,3-dihydro-4H-benzo[b][1,4]oxazin-4-yl)methanone;

(2,3-Dihydro-4H-benzo[b][1,4]oxazin-4-yl)(6-(3-(trifluoromethoxy)phenyl)pyrazin-2-yl)methanone;

(2,3-Dihydro-4H-benzo[b][1,4]oxazin-4-yl)(5-phenylpyridin-3-yl)methanone;

(5-(4-Chlorophenyl)pyridin-3-yl)(2,3-dihydro-4H-benzo[b][1,4]oxazin-4-yl)methanone;

(6-(2,3-Dihydrobenzofuran-6-yl)pyrazin-2-yl)(3,4-dihydroquinolin-1(2H)-yl)methanone;

(2,3-Dihydro-4H-benzo[b][1,4]oxazin-4-yl)(6-(2,3-dihydrobenzofuran-6-yl)pyrazin-2-yl)methanone;

(3,4-Dihydroquinolin-1(2H)-yl)(6-(4-methoxyphenyl)pyrazin-2-yl)methanone;

(3,4-Dihydroquinolin-1(2H)-yl)(6-phenylpyrazin-2-yl)methanone;

(3,4-Dihydroquinolin-1(2H)-yl)(5-(4-fluorophenyl)pyridin-3-yl)methanone;

(5-(4-Chlorophenyl)pyridin-3-yl)(2,3-dihydro-4H-benzo[b][1,4]oxazin-4-yl)methanone;

(3,4-Dihydroquinolin-1(2H)-yl)(5-(4-methoxyphenyl)pyridin-3-yl)methanone;

(5-(3,4-Difluorophenyl)pyridin-3-yl)(2,3-dihydro-4H-benzo[b][1,4]oxazin-4-yl)-methanone;

(2,3-Dihydro-4H-benzo[b][1,4]oxazin-4-yl)(6-(4-fluorophenyl)pyrazin-2-yl)methanone;

(6-(4-Fluorophenyl)pyrazin-2-yl)(4-methyl-3,4-dihydroquinoxalin-1(2H)-yl)methanone;

(6-(4-Fluorophenyl)pyrazin-2-yl)(2-methyl-3,4-dihydroquinolin-1(2H)-yl)methanone;

(2,3-Dihydro-4H-benzo[b][1,4]oxazin-4-yl)(5-(4-methoxyphenyl)pyridin-3-yl)-methanone;

(2,3-Dihydro-4H-benzo[b][1,4]oxazin-4-yl)(5-(4-fluorophenyl)pyridin-3-yl)methanone;

(3,4-Dihydroquinolin-1(2H)-yl)(6-(3-methoxyphenyl)pyrazin-2-yl)methanone;

(6-(4-Fluorophenyl)pyrazin-2-yl)(3-methyl-2,3-dihydro-4H-benzo[b][1,4]oxazin-4-yl)methanone;
(2,3-Dihydro-4H-benzo[b][1,4]oxazin-4-yl)(5-(4-fluoro-3-hydroxyphenyl)pyridin-3-yl)methanone;
(5-(2,4-Difluorophenyl)pyridin-3-yl)(2,3-dihydro-4H-benzo[b][1,4]oxazin-4-yl)-methanone;
(6-(2,3-Dihydrobenzofuran-6-yl)pyrazin-2-yl)(octahydro-4H-benzo[b][1,4]oxazin-4-yl)-methanone;
(3,4-Dihydroquinolin-1(2H)-yl)(6-(4-fluorophenyl)pyridazin-4-yl)methanone;
(5-(4-Fluorophenyl)pyridin-3-yl)(4-methyl-3,4-dihydroquinoxalin-1(2H)-yl)methanone;
(2,3-Dihydro-4H-benzo[b][1,4]oxazin-4-yl)(5-(4-nitrophenyl)pyridin-3-yl)methanone;
(5-(Cyclohex-1-en-1-yl)pyridin-3-yl)(2,3-dihydro-4H-benzo[b][1,4]oxazin-4-yl)methanone;
(3,4-Dihydro-1,5-naphthyridin-1(2H)-yl)(5-(4-methoxyphenyl)pyridin-3-yl)methanone;
Ethyl 4-(6-(4-fluorophenyl)pyrazine-2-carbonyl)-3,4-dihydro-2H-benzo[b][1,4]oxazine-2-carboxylate;
1-(5-Phenylnicotinoyl)-2,3-dihydroquinolin-4(1H)-one;
(3,4-Dihydro-1,5-naphthyridin-1(2H)-yl)(6-phenylpyrazin-2-yl)methanone;
(3,4-Dihydroquinolin-1(2H)-yl)(5-(3-methoxyphenyl)pyridin-3-yl)methanone;
(5-(1H-Pyrrol-1-yl)pyridin-3-yl)(3,4-dihydroquinolin-1(2H)-yl)methanone;
(2,3-Dihydro-4H-benzo[b][1,4]oxazin-4-yl)(6-(4-fluorophenyl)pyridazin-4-yl)-methanone;
(2,3-Dihydro-4H-benzo[b][1,4]oxazin-4-yl)(5-(2-fluorophenyl)pyridin-3-yl)methanone;
(3,4-Dihydro-1,5-naphthyridin-1(2H)-yl)(5-(4-fluorophenyl)pyridin-3-yl)methanone;
(2,3-Dihydro-4H-benzo[b][1,4]oxazin-4-yl)(6-(1-methyl-1H-pyrazol-4-yl)pyrazin-2-yl)methanone;
(2,3-Dihydro-4H-benzo[b][1,4]oxazin-4-yl)(5-(4-(trifluoromethyl)phenyl)pyridin-3-yl)methanone;
(2,3-Dihydro-4H-benzo[b][1,4]oxazin-4-yl)(5-(4-fluoro-2-methoxyphenyl)pyridin-3-yl)methanone;
4-((5-(4-Fluorophenyl)pyridin-3-yl)sulfonyl)-3,4-dihydro-2H-benzo[b][1,4]oxazine;
1-((5-(4-Fluorophenyl)pyridin-3-yl)sulfonyl)-1,2,3,4-tetrahydroquinoline;
(2,3-Dihydro-4H-benzo[b][1,4]oxazin-4-yl)(5-(3-(trifluoromethyl)phenyl)pyridin-3-yl)methanone;
(2,3-Dihydro-4H-benzo[b][1,4]oxazin-4-yl)(6'-fluoro-[3,3'-bipyridin]-5-yl)methanone;
(2,3-Dihydro-4H-benzo[b][1,4]oxazin-4-yl)(5-(3-methoxyphenyl)pyridin-3-yl)-methanone;
(3,4-Dihydroquinolin-1(2H)-yl)(5-(1-phenylvinyl)pyridin-3-yl)methanone;
(3,4-Dihydroquinolin-1(2H)-yl)(6-phenylpyridazin-4-yl)methanone;
(6-Methoxy-3,4-dihydroquinolin-1(2H)-yl)(5-phenylpyridin-3-yl)methanone;
(3,4-Dihydroquinolin-1(2H)-yl)(5-(4-(hydroxymethyl)phenyl)pyridin-3-yl)methanone;
(5-(4-Fluorophenyl)pyridin-3-yl)(octahydro-4H-benzo[b][1,4]oxazin-4-yl)methanone;
(5-(4-Fluorophenyl)pyridin-3-yl)((4aS,8aS)-octahydro-4H-benzo[b][1,4]oxazin-4-yl)methanone;
(5-(4-Fluorophenyl)pyridin-3-yl)((4aR,8aR)-octahydro-4H-benzo[b][1,4]oxazin-4-yl)methanone;
(2,3-Dihydro-4H-benzo[b][1,4]oxazin-4-yl)(5-(4-fluoro-3-nitrophenyl)pyridin-3-yl)methanone;
(5-Methoxy-3,4-dihydroquinolin-1(2H)-yl)(5-phenylpyridin-3-yl)methanone;
(5-(4-Fluorophenyl)pyridin-3-yl)(indolin-1-yl)methanone;
(3,4-Dihydro-1,5-naphthyridin-1(2H)-yl)(5-phenylpyridin-3-yl)methanone;
[3,4'-Bipyridin]-5-yl(3,4-dihydroquinolin-1(2H)-yl)methanone;
(2,3-Dihydro-4H-benzo[b][1,4]oxazin-4-yl)(6-(1-methyl-1H-pyrazol-5-yl)pyrazin-2-yl)methanone;
(6-(4-Fluorophenyl)pyridazin-4-yl)(2-methyl-3,4-dihydroquinolin-1(2H)-yl)methanone;
(2,3-Dihydro-4H-benzo[b][1,4]oxazin-4-yl)(5-(4-(hydroxymethyl)phenyl)pyridin-3-yl)methanone;
(5-(3,6-Dihydro-2H-pyran-4-yl)pyridin-3-yl)(2,3-dihydro-4H-benzo[b][1,4]oxazin-4-yl)methanone;
Methyl 1-(5-phenylnicotinoyl)-1,2,3,4-tetrahydroquinoline-6-carboxylate;
(3,4-Dihydroquinolin-1(2H)-yl)(5-(4-((dimethylamino)methyl)phenyl)pyridin-3-yl)methanone;
(7-Methoxy-3,4-dihydroquinolin-1(2H)-yl)(5-phenylpyridin-3-yl)methanone;
[3,3'-Bipyridin]-5-yl(3,4-dihydroquinolin-1(2H)-yl)methanone;
(2,3-Dihydro-4H-benzo[b][1,4]oxazin-4-yl)(5-(p-tolyl)pyridin-3-yl)methanone;
(5-(2,3-Dihydrobenzofuran-6-yl)pyridin-3-yl)(octahydro-4H-benzo[b][1,4]oxazin-4-yl)-methanone;
(2,3-Dihydro-4H-benzo[b][1,4]oxazin-4-yl)(5-(1-methyl-1H-pyrazol-4-yl)pyridin-3-yl)methanone;
(2,3-Dihydro-4H-benzo[b][1,4]oxazin-4-yl)(5-(pyrrolidin-1-yl)pyridin-3-yl)methanone;
2,3-Dihydro-4H-benzo[b][1,4]oxazin-4-yl)(5-(6,6-dimethyl-3-azabicyclo[3.1.0]hexan-3-yl)pyridin-3-yl)methanone;
(6-(3,3-Difluoroazetidin-1-yl)pyrazin-2-yl)(2,3-dihydro-4H-benzo[b][1,4]oxazin-4-yl)methanone;
(2,3-Dihydro-4H-benzo[b][1,4]oxazin-4-yl)(6-(4-methylpiperazin-1-yl)pyrazin-2-yl)methanone;
1-(3,4-Dihydroquinolin-1(2H)-yl)-2-(5-(4-fluorophenyl)pyridin-3-yl)ethan-1-one;
1-(2,3-Dihydro-4H-benzo[b][1,4]oxazin-4-yl)-2-(5-(4-methoxyphenyl)pyridin-3-yl)ethan-1-one;
4-((5-Phenylpyridin-3-yl)methyl)-3,4-dihydro-2H-benzo[b][1,4]oxazine;
(3,4-Dihydroquinolin-1(2H)-yl)(5-(4-methyl-1H-imidazol-1-yl)pyridin-3-yl)methanone;
(3,4-Dihydroquinolin-1(2H)-yl)(6-(4-methyl-1H-imidazol-1-yl)pyrazin-2-yl)methanone;
(3,4-Dihydroquinolin-1(2H)-yl)(6-(4-methyl-1H-pyrazol-1-yl)pyrazin-2-yl)methanone;
(6-Benzylpyrazin-2-yl)(3,4-dihydroquinolin-1(2H)-yl)methanone;
1-(2,3-Dihydro-4H-benzo[b][1,4]oxazin-4-yl)-2-(5-(4-fluorophenyl)pyridin-3-yl)ethan-1-one;
(3,4-Dihydroquinolin-1(2H)-yl)(6-(3,5-dimethyl-1H-pyrazol-1-yl)pyrazin-2-yl)-methanone;
(3,4-Dihydroquinolin-1(2H)-yl)(5-(4-methyl-1H-pyrazol-1-yl)pyridin-3-yl)methanone;
1-((5-(4-Fluorophenyl)pyridin-3-yl)methyl)-1,2,3,4-tetrahydroquinoline;
1-((5-(4-Fluorophenyl)pyridin-3-yl)methyl)indoline; or
or a tautomer or pharmaceutically acceptable salts thereof.

19. A method for the treatment of a steroid receptor dependent condition or disease comprising administering to a subject in need thereof a therapeutically effective amount of a compound of formula (I) or a pharmaceutically acceptable salt thereof (I)

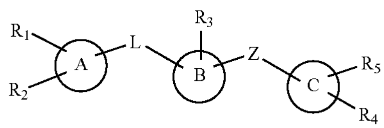

wherein

A is a 3-10 membered carbocyclyl or a 4-12 membered heterocyclyl containing 1-4 heteroatoms selected from O, N, and S;

B is (1)

(2)

(3)

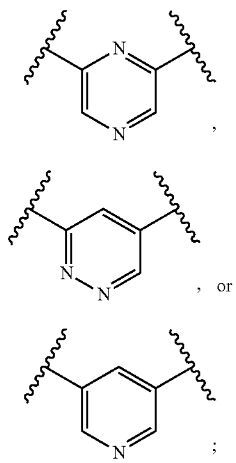

, , or ;

C is (1')

(2')

(3')

(4')

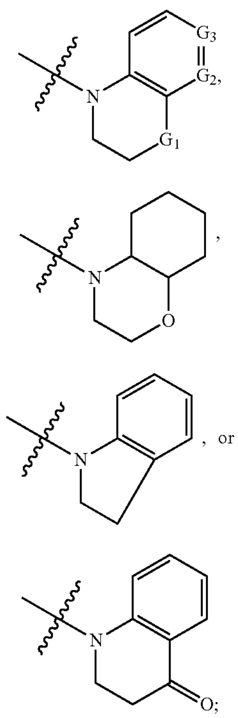

, , , or ;

$G_1$ is $CH_2$, NH, or O;

$G_2$ and $G_3$ are, independently, CH or N;

Z is —C(O)—, —$SO_2$—, —$C_{1-3}$ alkyl-, or —$CH_2$—C(O)—;

L is a bond, —$C_{1-7}$ alkyl-, or —$C_{1-7}$ alkenyl-;

$R_1$ is hydrogen, $C_{1-7}$ alkyl, $C_{1-7}$ alkoxy, halogen, hydroxy, nitro, halogen $C_{1-7}$ alkyl, hydroxy $C_{1-7}$ alkyl, —O-halogen $C_{1-7}$ alkyl, or —X—$NR_6R_7$;

$R_2$ is hydrogen, hydroxy, $C_{1-7}$ alkyl, or halogen;

$R_3$ is hydrogen, $C_{1-7}$ alkyl, or amino;

$R_4$ is hydrogen, $C_{1-7}$ alkyl, $C_{1-7}$ alkoxy, halogen, hydroxy, hydroxy $C_{1-7}$ alkyl, halogen $C_{1-7}$ alkyl, or —C(O)—O—$C_{1-7}$ alkyl;

$R_5$ is hydrogen, halogen, $C_{1-7}$ alkoxy, or $C_{1-7}$ alkyl;

X is a bond or $C_{1-7}$ alkyl; and $R_6$ and $R_7$ are, independently, hydrogen or $C_{1-7}$ alkyl.

20. The method according to claim 19, wherein the steroid receptor dependent condition or disease is cancer.

21. The method according to claim 20, wherein the steroid receptor dependent condition or disease is prostate cancer or breast cancer.

22. The method according to claim 19, wherein the method comprises administering a therapeutically effective amount of a compound of formula (I) in addition to a glucocorticoid and/or a mineralocorticoid and, optionally, one or more anti-cancer agents.

23. The method according to claim 19, wherein the method comprises administering a therapeutically effective amount of a compound of formula (I) in addition to one or more anti-cancer agents selected from the group consisting of:

non-steroidal androgen receptor antagonists;

steroidogenesis inhibitors;

chemotherapeutic agents;

antiestrogens;

epigenetic modulators;

mTOR inhibitors;

AKT inhibitors;

radiopharmaceuticals;

GnRH/LHRH analogues;

PI3K inhibitors; and

CDK4/6 inhibitors wherein the compound of formula (I) and the one or more anti-cancer agents are administered simultaneous, separate or sequentially.

24. A pharmaceutical composition comprising a compound according to claim 1 together with a pharmaceutically acceptable carrier.

25. A pharmaceutical combination comprising a compound according to claim 1 and at least one additional active ingredient selected from the list consisting of:

glucocorticoids;

mineralocorticoids;

non-steroidal androgen receptor antagonists;

steroidogenesis inhibitors;

chemotherapeutic agents;

antiestrogens;

epigenetic modulators;

mTOR inhibitors;

AKT inhibitors;

radiopharmaceuticals;

GnRH/LHRH analogues;

PI3K inhibitors; and

CDK4/6 inhibitors; and wherein the pharmaceutical combination is administered simultaneously, separately, or sequentially.

26. Compound (2,3-Dihydro-4H-benzo[b][1,4]oxazin-4-yl)(6-(pyrrolidin-1-yl)pyrazin-2-yl)methanone, or a tautomer or a pharmaceutically acceptable salt thereof.
27. A compound of formula (I) or a pharmaceutically acceptable salt thereof
(I)
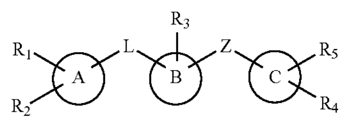
wherein:
B is
(1)
(2)
(3)
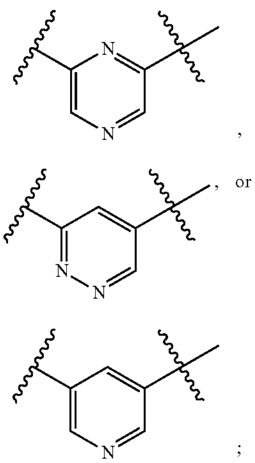
, , or ;
such that
i) when B is
(1)
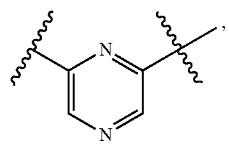
,
then
A is:
(1″)
(2″)
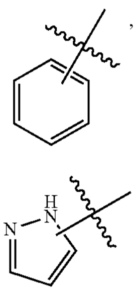
, ,
-continued
(3″)
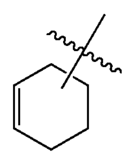
,
(4″)
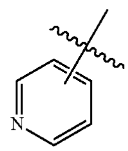
,
(5″)
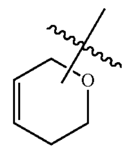
,
(6″)
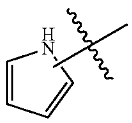
,
(8″)
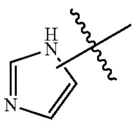
,
(9″)
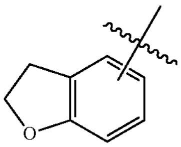
,
(10″)
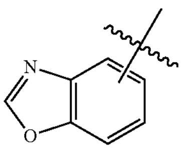
,
(11″)
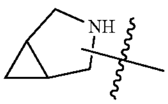
,
(12″)
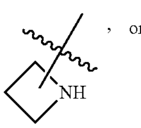
, or
(13″)
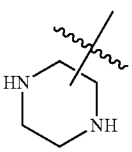
;

C is:

(1′)

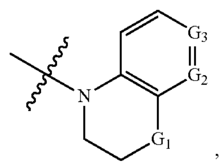

, (2′)

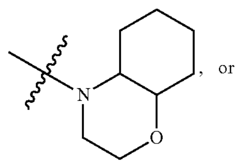

, or (3′)

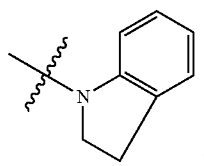

;

$G_1$ is $CH_2$, NH or O;

$G_2$ and $G_3$ are, independently, CH or N;

Z is —C(O)—, —$SO_2$—, —$C_{1-3}$ alkyl- or —$CH_2$—C(O)—;

L is a bond, —$C_{1-7}$ alkyl- or —$C_{1-7}$ alkenyl-;

$R_1$ is hydrogen, $C_{1-7}$ alkyl, $C_{1-7}$ alkoxy, halogen, hydroxy, nitro, halogen $C_{1-7}$ alkyl, hydroxy $C_{1-7}$ alkyl, —O-halogen $C_{1-7}$ alkyl or —X—$NR_6R_7$;

$R_2$ is hydrogen, hydroxy, $C_{1-7}$ alkyl or halogen;

$R_3$ is hydrogen, $C_{1-7}$ alkyl or amino;

$R_4$ is hydrogen, $C_{1-7}$ alkyl, $C_{1-7}$ alkoxy, halogen, hydroxy, hydroxy $C_{1-7}$ alkyl, halogen $C_{1-7}$ alkyl or —C(O)—O—$C_{1-7}$ alkyl;

$R_5$ is hydrogen, halogen, $C_{1-7}$ alkoxy or $C_{1-7}$ alkyl;

X is a bond or $C_{1-7}$ alkyl; and $R_6$ and $R_7$ are, independently, hydrogen or $C_{1-7}$ alkyl;

ii) when B is (2)

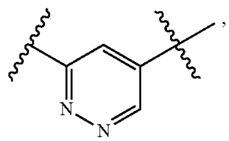

, then

A is a 3-10 membered carbocyclyl or a 4-12 membered heterocyclyl containing 1-4 heteroatoms selected from O, N, and S;

C is:

(1′)

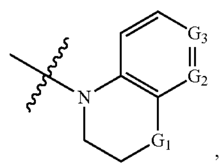

,

-continued (2′)

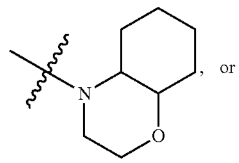

, or (3′)

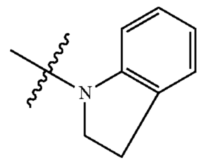

;

$G_1$ is $CH_2$, NH or O;

$G_2$ and $G_3$ are, independently, CH or N;

Z is —C(O)—, —$SO_2$—, —$C_{1-3}$ alkyl- or —$CH_2$—C(O)—;

L is a bond, —$C_{1-7}$ alkyl- or —$C_{1-7}$ alkenyl-;

$R_1$ is hydrogen, $C_{1-7}$ alkyl, $C_{1-7}$ alkoxy, halogen, hydroxy, nitro, halogen $C_{1-7}$ alkyl, hydroxy $C_{1-7}$ alkyl, —O-halogen $C_{1-7}$ alkyl or —X—$NR_6R_7$;

$R_2$ is hydrogen, hydroxy, $C_{1-7}$ alkyl or halogen;

$R_3$ is hydrogen, $C_{1-7}$ alkyl or amino;

$R_4$ is hydrogen, $C_{1-7}$ alkyl, $C_{1-7}$ alkoxy, halogen, hydroxy, hydroxy $C_{1-7}$ alkyl, halogen $C_{1-7}$ alkyl or —C(O)—O—$C_{1-7}$ alkyl;

$R_5$ is hydrogen, halogen, $C_{1-7}$ alkoxy or $C_{1-7}$ alkyl;

X is a bond or $C_{1-7}$ alkyl; and $R_6$ and $R_7$ are, independently, hydrogen or $C_{1-7}$ alkyl;

and iii) when B is (3)

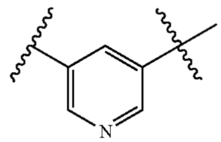

, then

A is (1″)

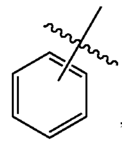

, (2″)

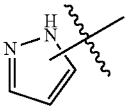

, (3″)

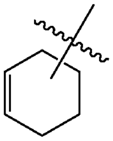

,

-continued (4")

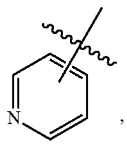

, (5")

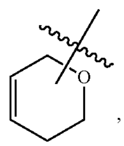

, (6")

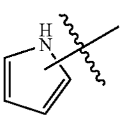

, (7")

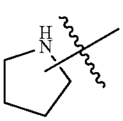

, (8")

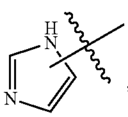

, (9")

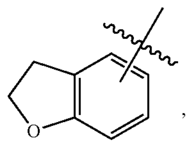

, (10")

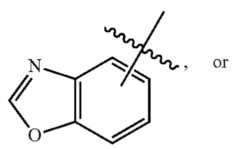

, or (11")

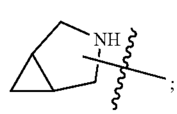

;

provided that when C is ring (3'), then A is not ring (2") or ring (7");

C is (1')

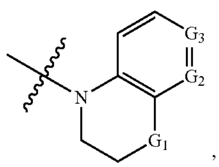

,

-continued (2')

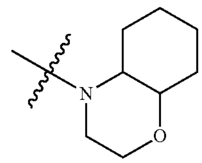

, (3')

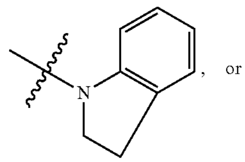

, or (4')

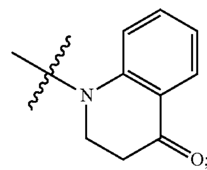

$G_1$ is $CH_2$, NH or O;

$G_2$ and $G_3$ are, independently, CH or N;

Z is —C(O)—, —$SO_2$—, —$C_{1-3}$ alkyl- or —$CH_2$—C(O)—;

L is a bond, —$C_{1-7}$ alkyl- or —$C_{1-7}$ alkenyl-;

$R_1$ is hydrogen, $C_{1-7}$ alkyl, $C_{1-7}$ alkoxy, halogen, hydroxy, halogen $C_{1-7}$ alkyl, hydroxy $C_{1-7}$ alkyl, —O-halogen $C_{1-7}$ alkyl, or —X—$NR_6R_7$, $R_2$ is hydrogen, hydroxy, $C_{1-7}$ alkyl or halogen;

$R_3$ is hydrogen, $C_{1-7}$ alkyl, or amino;

$R_4$ is hydrogen, $C_{1-7}$ alkyl, $C_{1-7}$ alkoxy, halogen, hydroxy $C_{1-7}$ alkyl, halogen $C_{1-7}$ alkyl or —C(O)—O—$C_{1-7}$ alkyl;

$R_5$ is hydrogen, halogen, $C_{1-7}$ alkoxy, or $C_{1-7}$ alkyl;

X is a bond or $C_{1-7}$ alkyl; and $R_6$ and $R_7$ are, independently, hydrogen, or $C_{1-7}$ alkyl;

with the proviso that the compound of formula (I) is not:

(3,4-Dihydro-3-methoxy-1(2H)-quinolinyl)(6-phenyl-4-pyridazinyl)methanone;

(6-Fluoro-3,4-dihydro-4-methyl-1(2H)-quinoxalinyl)(5-phenyl-3-pyridinyl)methanone;

(3,4-Dihydro-1(2H)-quinolinyl)(5-phenyl-3-pyridinyl)methanone;

(5-(2,3-Dihydro-5-benzofuranyl)-3-pyridinyl)(3,4-dihydro-1(2H)-quinolinyl)methanone;

(5-(2,3-Dihydro-5-benzofuranyl)-3-pyridinyl)(7-fluoro-2,3-dihydro-4H-1,4-benzoxazin-4-yl)methanone;

(6,8-Difluoro-3,4-dihydro-1(2H)-quinolinyl)(5-(4-(dimethylamino)phenyl)-3-pyridinyl)methanone;

(3,4-Dihydro-1(2H)-quinolinyl)(5-(1-pyrrolidinyl)-3-pyridinyl)methanone;

(5-(2,3-Dihydro-5-benzofuranyl)-3-pyridinyl)(octahydro-4H-1,4-benzoxazin-4-yl)methanone;

(5-(4-Methoxyphenyl)-3-pyridinyl)(octahydro-4H-1,4-benzoxazin-4-yl)methanone or (2,3-Dihydro-1H-indol-1-yl)(5-phenyl-3-pyridinyl)methanone.

* * * * *